(12) United States Patent
Badik et al.

(10) Patent No.: US 11,715,340 B1
(45) Date of Patent: Aug. 1, 2023

(54) SMART STORAGE AND VENDING SYSTEM

(71) Applicant: KURE. LLC, Newark, DE (US)

(72) Inventors: Yale Badik, Madison, CT (US);
Deanna Felker, West Hills, CA (US)

(73) Assignee: KURE LLC, Madison, CT (US)

( * ) Notice: Subject to any disclaimer, the term of this patent is extended or adjusted under 35 U.S.C. 154(b) by 0 days.

(21) Appl. No.: 17/990,997

(22) Filed: Nov. 21, 2022

Related U.S. Application Data

(63) Continuation of application No. 17/739,756, filed on May 9, 2022, now Pat. No. 11,521,444.

(51) Int. Cl.
*G07C 9/00* (2020.01)
*G16H 20/13* (2018.01)
*H04L 9/40* (2022.01)

(52) U.S. Cl.
CPC ..... *G07C 9/00563* (2013.01); *G07C 9/00571* (2013.01); *G07C 9/00912* (2013.01); *G16H 20/13* (2018.01); *H04L 63/083* (2013.01); *H04L 63/0861* (2013.01)

(58) Field of Classification Search
None
See application file for complete search history.

(56) References Cited

U.S. PATENT DOCUMENTS

| | | | |
|---|---|---|---|
| 8,082,452 | B2 | 12/2011 | Jajodia |
| 8,566,269 | B2 | 10/2013 | Jajodia et al. |
| 9,203,861 | B2 | 12/2015 | Albanese et al. |
| 9,436,822 | B2 | 9/2016 | Ghosh et al. |
| 9,846,588 | B2 | 12/2017 | Ghosh et al. |
| 10,709,643 | B2 | 7/2020 | Hsu |
| 10,956,184 | B2 | 4/2021 | Ghosh et al. |
| 11,100,741 | B2 | 8/2021 | Rahilly et al. |
| 11,521,444 | B1* | 12/2022 | Badik ................ G07C 9/00563 |
| 2010/0054481 | A1 | 3/2010 | Jajodia et al. |
| 2010/0058456 | A1 | 3/2010 | Jajodia et al. |
| 2016/0022542 | A1 | 1/2016 | Lehmann et al. |
| 2021/0249112 | A1 | 8/2021 | Mercolino et al. |
| 2021/0343404 | A1 | 11/2021 | Hunt et al. |
| 2021/0398635 | A1 | 12/2021 | Alanazi |

* cited by examiner

*Primary Examiner* — K. Wong
(74) *Attorney, Agent, or Firm* — Dave Law Group LLC; Raj S. Dave

(57) ABSTRACT

Embodiments relate to a system comprising a drug storage comprising a container to hold a drug; a communication module; and a cyber security module. The system is operable to log record of access to the drug and maintain a ledger of the record of access to the drug using a blockchain technology. The access to the drug is secured by the cyber security module.

20 Claims, 20 Drawing Sheets

SMART STORAGE AND VENDING SYSTEM

CROSS-REFERENCE TO RELATED APPLICATIONS

This Application is a Continuation-In-Part of U.S. patent application Ser. No. 17/739,756, filed on May 9, 2022; the contents of which is incorporated herein in its entirety by reference.

FIELD OF THE INVENTION

This invention relates to smart storage. The invention more particularly relates to a tamper proof smart storage system and a vending system and a method thereof.

BACKGROUND

In this section the prior art relevant to the field is cited.

"A device includes a reservoir for holding an article that has thereon and a dispenser for dispensing the articles from the reservoir. A deactivation mechanism may deactivate medicament held within the reservoir." [Source: Integrated device and system for drug dispensing; published as US20210249112A1 on Aug. 12, 2021]

"The invention relates to a portable drug dispenser system that includes a chamber for holding a plurality of separately contained medication canisters, a dispensing mechanism for dispensing one or more of the plurality of medication products from the medication canisters and includes a processor to determine the time of each activation of the dispensing mechanism and to transmit the medication to a locked dispensing station which is only openable by either a password or biometric means. The dispenser also includes a connection to a smart device to provide the user information and alarms." [Source: Medication compliance device; published as US20210398635A1 on Dec. 23, 2021]

"Secure medication storage is described herein. A smart latch includes an actuator, a communication interface, a display, and a processor. The actuator is configured to open and close a latch to secure a door of the enclosure. The processor can be configured to receive a user credentials for accessing the enclosure, validate the user credentials for accessing the enclosure, trigger the actuator to open the latch, thereby allowing the door to be opened, and trigger the actuator to close the latch after detecting that the door is closed, thereby securing the door." [Source: Secure inventory access and control mechanism; published as U.S. Ser. No. 11/100,741B2 on Aug. 24, 2021]

"Described herein is an integrated health management system, and method that includes a pre-packaged tablet delivery apparatus configured to deliver pre-packaged tablets to a user. The delivery apparatus comprising an alignment guide, a processor modulated differential drive used for the directional control of the pre-packaged tablets, a sensor for sensing a location and an orientation of the pre-packaged tablet, a cutter mechanism, and cutter mechanism control logic. The sensed location and orientation of the pre-packaged tablet is used to modulate the differential drive. The cutter mechanism control logic is configured to monitor the sensed pre-packaged tablet location and orientation, then initiate a cutting sequence responsive to at least one of the predetermined configurations within the processor and the dynamic configuration responsive to determining an optimal sensed location and orientation. The control logic generates and logs a message into the distributed database responsive to the cutting sequence." [Source: Health management system; published as US20210343404A1 on Nov. 4, 2021]

"A self-medication management system and method comprising at least a plurality of receptacles, a scanner, a display screen, and a processor to acquire medication information from a medication container, determine whether the medication information exists in a first database, if the medication information does not exist in the first database, associate the medication information with a location information comprising a receptacle and store the medication information and the location information in the first database, indicate the location information, and confirm placement of the medication container in the associated receptacle, notify a user to administer the medication held in the medication container, and request the user to scan the medication container of the notified medication, detect retrieval of an incorrect medication container from the plurality of receptacles, and issue a warning of the detection, and provide instructions for administering the medication." [Source: Home medication manager; published as US20160022542A1 on Jan. 21, 2021]

There is a need for smart storage that ensures the safety of the access to the drug. There is a need to keep the record of access to the drug safe from hackers and thereby avoiding potential misuse of the drug.

SUMMARY

The following presents a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

An embodiment relates to a system comprising a drug vending system; wherein the drug vending system comprises a drug storage system comprising a drug storage to hold a drug container comprising a drug; a processor; a memory; wherein the processor is communicatively coupled with the memory; a communication module; and a cyber security module; and wherein the processor is operable to: log a record of access to the drug container, and maintain a ledger of the record of access to the drug container using a blockchain technology; and wherein the drug vending system is secured through the cyber security module.

In an embodiment of the system, the system comprises a user interface to interact with a user.

In an embodiment of the system, the user interface comprises: an interactive display, wherein the interactive display comprises at least one of an LED display, an LCD display, and a kiosk that comprises at least one of a web application and a mobile application.

In an embodiment of the system, the system is in communication with a server through the communication module.

In an embodiment of the system, the server comprises a database.

In an embodiment of the system, the server comprises at least one of a local server, a remote server, and a cloud server.

In an embodiment of the system, the system receives a prescription through the user interface.

In an embodiment of the system, the prescription comprises a unique code comprising at least one of a barcode, a Universal Product Code indicia, a Quick Response code, a high-capacity color barcode, and a near-field communication code.

In an embodiment of the system, the unique code comprises a blockchain code.

In an embodiment of the system, the user interface comprises a scanner to scan the prescription.

In an embodiment of the system, the prescription is received from a digital medium and as a blockchain token.

In an embodiment of the system, the system receives an identification of the user through the user interface.

In an embodiment of the system, the identification of the user comprises at least one of a biometric identity of the user and a unique identity.

In an embodiment of the system, the biometric identity comprises at least one of a fingerprint, an eyeblink, a retina scan, an iris scan, an eye scan, and a facial image scan.

In an embodiment of the system, the unique identity comprises at least one of an alphanumeric password, a unique identification number, an RFID tag, a password, a barcode, and a Quick response QR code.

In an embodiment of the system, the user interface further comprises a biometric scanner to scan the biometric identity of the user.

In an embodiment of the system, the user interface further comprises a keypad; a touchpad; a scanner; and an RFID reader.

In an embodiment of the system, the scanner comprises at least one of a Universal Product Code indicia scanner, a Quick Response code scanner, a high-capacity color barcode scanner, and a near-field communication scanner.

In an embodiment of the system, the processor is operable to interact with the server to authenticate the user by matching credentials of the unique identity with a record of the user stored in the database.

In an embodiment of the system, the drug vending system is locked for further access if the credentials of the unique identity do not match with the record of the user in the database.

In an embodiment of the system, the processor is operable to interact with the server to authenticate the user by matching credentials of the biometric identity with a record of the user stored in the database.

In an embodiment of the system, the drug vending system is locked for further access if the credentials of the biometric identity do not match with the record of the user in the database.

In an embodiment of the system, the system is installed at least one of a pharmacy and a drug store.

In an embodiment of the system, the system is installed at a box store.

In an embodiment of the system, the system provides an access to the system to refill the prescription into the drug storage.

In an embodiment of the system, the system checks and authenticates dispensing of the drug with an inventory of the drug according to the prescription received; and dispenses the drug container from the drug vending system.

In an embodiment of the system, the drug container comprises an indicator tag comprising at least one of a Universal Product Code indicia, a Quick Response code, a high-capacity color barcode, and a near-field communication tag on the drug container.

In an embodiment of the system, the indicator tag is scanned by the system while dispensing the drug into the drug container through the drug vending system.

In an embodiment of the system, the indicator tag is utilized to identify the drug container.

In an embodiment of the system, the indicator tag comprises a detail of the drug comprising a batch number, an inventory count of the drug dispensed into the drug container, a name of the drug, an expiry date, and a disease that the drug is being used to treat.

In an embodiment of the system, the detail of the drug is sent to the server on each access to the drug container from the drug storage in order to track the access to the drug container.

In an embodiment of the system, the system is a Drug Enforcement Administration compliant system.

In an embodiment of the system, the record of access to the drug container is encrypted by the system.

In an embodiment of the system, the record of access is viewable on a dashboard.

In an embodiment of the system, the record of access is accessible to an authorized third-party official for unbiased monitoring.

In an embodiment of the system, the record of access comprises: a name of drug, a time, a date, a day, a month, a year, a quantity of the drug accessed, name of the user receiving the drug container, and a quantity of drug remaining in the drug container.

In an embodiment of the system, the cyber security module further comprises an information security management module providing isolation between the system and the server.

In an embodiment of the system, the information security management module is operable to receive data from at least one of an input interface, the drug storage, and the database; exchange a security key at a start of the communication between the communication module and the server; receive the security key from the server; authenticate an identity of the server by verifying the security key; analyze the security key for potential cyber security threats; negotiate an encryption key between the communication module and the server; encrypt the data; and transmit the encrypted data to the server in case no cyber security threat is detected.

In an embodiment of the system, the information security management module is operable to exchange a security key at a start of the communication between the communication module and the server; receive the security key from the server; authenticate an identity of the server by verifying the security key; analyze the security key for potential cyber security threats; negotiate an encryption key between the system and the server; receive encrypted data; decrypt the encrypted data; perform an integrity check of the decrypted data; and transmit the decrypted data to at least one of an output interface, the drug storage, and the database through the communication module in case no cyber security threat is detected.

In an embodiment of the system, the information security management module is configured to raise an alarm if the cyber security threat is detected.

In an embodiment of the system, the information security management module is configured to discard the encrypted data received if the integrity check of the encrypted data fails.

In an embodiment of the system, the information security management module is configured to check the integrity of the encrypted data by checking accuracy, consistency, and any possible data loss during the communication through the communication module.

In an embodiment of the system, the information security management module is configured to perform asynchronous authentication and validation of the communication between the communication module and the server.

In an embodiment of the system, a perimeter network provides an extra layer of protection.

In an embodiment of the system, the perimeter network protects the system from the cyber security threat by using a plurality of firewalls.

An embodiment relates to a method comprising steps of receiving an identification of a user through a drug vending system; authenticating the user through the drug vending system; receiving a prescription through the drug vending system; dispensing a drug container through the drug vending system to the user; communicating through a communication module; logging a record of access to the drug container; and maintaining a ledger of the record of access to the drug container using blockchain technology; and wherein the drug vending system is secured through a cyber security module.

In an embodiment of the method, the method further comprises receiving the prescription through a user interface of the drug vending system.

In an embodiment of the method, the prescription comprises a unique code comprising at least one of a barcode, a Universal Product Code indicia, a Quick Response code, a high-capacity color barcode, and a near-field communication code.

In an embodiment of the method, the unique code comprises a blockchain code.

In an embodiment of the method, the prescription is received from a digital medium and as a blockchain token.

In an embodiment of the method, the method further comprises receiving the identification of the user through the user interface.

In an embodiment of the method, the identification of the user comprises at least one of a biometric identity of the user and a unique identity.

In an embodiment of the method, the biometric identity comprises at least one of a fingerprint, an eyeblink, a retina scan, an iris scan, an eye scan, and a facial image scan.

In an embodiment of the method, the unique identity comprises at least one of an alphanumeric password, a unique identification number, an RFID tag, a password, a barcode, and a Quick response QR code.

In an embodiment of the method, the method further comprises interacting with a server to authenticate the user by matching credentials of the unique identity with a record of the user stored in a database.

In an embodiment of the method, the method further comprises locking the drug vending system for further access if the credentials of the unique identity do not match with the record of the user in the database.

In an embodiment of the method, the method further comprises interacting with a server to authenticate the user by matching credentials of the biometric identity with a record of the user stored in a database.

In an embodiment of the method, the method further comprises locking the drug vending system for further access if the credentials of the biometric identity do not match with the record of the user in the database.

In an embodiment of the method, the method comprises providing an access to the drug vending system to refill the prescription into the drug vending system.

In an embodiment of the method, the method further comprises checking and authenticating the dispensing of the drug container with an inventory of the drug container according to the prescription received; and dispensing the drug container from the drug vending system.

In an embodiment of the method, the method further comprises scanning an indicator tag by the drug vending system while dispensing the drug container through the drug vending system.

In an embodiment of the method, the indicator tag is utilized to identify the drug container.

In an embodiment of the method, the indicator tag comprises a detail of a drug comprising a batch number, an inventory count of the drug container, a name of the drug, an expiry date, and a disease it is used to treat.

In an embodiment of the method, the detail of the drug is sent to the server on each of the access to the drug container from the drug vending system in order to track the access to the drug container.

In an embodiment of the method, the method further comprises encrypting automatically, the record of access to the drug container.

In an embodiment of the method, the record of access is viewable on a dashboard.

In an embodiment of the method, the record of access is accessible to an authorized third-party official for unbiased monitoring.

In an embodiment of the method, the record of access comprises: a name of drug, a time, a date, a day, a month, a year, a quantity of the drug accessed, name of the user receiving the drug container, and a quantity of drug container remaining.

In an embodiment of the method, the method further comprises providing an isolation between the drug vending system and the server by an information security management module for cyber security.

In an embodiment of the method, the method comprises receiving data from at least one of an input interface, the drug vending system, the server, and the database; exchanging a security key at a start of a communication between the communication module and the server; receiving the security key from the server; authenticating an identity of the server by verifying the security key; analyzing the security key for potential cyber security threats; negotiating an encryption key between the communication module and the server; encrypting the data; and transmitting the encrypted data to the server in cases no cyber security threat is detected.

In an embodiment of the method, the method comprises exchanging a security key at a start of the communication between the communication module and the server; receiving the security key from the server; authenticating an identity of the server by verifying the security key; analyzing the security key for potential cyber security threats; negotiating an encryption key between the drug vending system and the server; receiving encrypted data; decrypting the encrypted data; performing an integrity check of the decrypted data; and transmitting the decrypted data to at least one of an output interface, the drug vending system, and the database through the communication module in case no cyber security threat is detected.

In an embodiment of the method, the method comprises raising an alarm if the cyber security threat is detected.

In an embodiment of the method, the method comprises raising an alarm if the cyber security threat is detected.

In an embodiment of the method, the method comprises discarding the encrypted data received if the integrity check of the encrypted data fails.

In an embodiment of the method, the method comprises checking integrity of the encrypted data by checking accuracy, consistency, and any possible data loss during the communication through the communication module.

In an embodiment of the method, the method comprises performing asynchronous authentication and validation of the communication between the communication module and the server.

In an embodiment of the method, the method comprises providing an extra layer of protection through a perimeter network.

In an embodiment of the method, the method comprises protecting the system from the cyber security threat by using a plurality of firewalls through the perimeter network.

An embodiment relates to a system comprising an automatic drug vending machine to dispense a drug container, a drug storage system comprising a drug storage to hold the drug container comprising a drug. The system further comprises a processor, a memory, wherein the processor is communicatively coupled with the memory, a communication module; and a cyber security module. The processor is operable to log a record of access to the drug container, maintain a ledger of the record of access to the drug container using a blockchain technology. The system is secured through the cyber security module.

In an embodiment, the system comprises a user interface to interact with a user.

In an embodiment of the system, the user interface comprises: an interactive display, wherein the interactive display comprises at least one of an LED display, an LCD display, and a kiosk that comprises at least one of a web application and a mobile application.

In an embodiment of the system, the system is in communication with a server through the communication module.

In an embodiment of the system, the server comprises a database.

In an embodiment of the system, the server comprises at least one of a local server, a remote server, and a cloud server.

In an embodiment of the system, the system receives a prescription through the user interface.

In an embodiment of the system, the prescription comprises a unique code comprising at least one of a barcode, a Universal Product Code indicia, a Quick Response code, a high-capacity color barcode, and a near-field communication code.

In an embodiment of the system, the unique code comprises a blockchain code.

In an embodiment of the system, the user interface comprises a scanner to scan the prescription.

In an embodiment of the system, the prescription is received from a digital medium and as a blockchain token.

In an embodiment of the system, the system receives an identification of the user through the user interface.

In an embodiment of the system, the identification of the user comprises at least one of a biometric identity of the user and a unique identity.

In an embodiment of the system, the biometric identity comprises at least one of a fingerprint, an eyeblink, a retina scan, an iris scan, an eye scan, and a facial image scan.

In an embodiment of the system, the unique identity comprises at least one of an alphanumeric password, a unique identification number, an RFID tag, a password, a barcode, and a Quick response QR code.

In an embodiment of the system, the user interface further comprises a biometric scanner to scan the biometric identity of the user.

In an embodiment of the system, the user interface further comprises a keypad; a touchpad; a scanner; and an RFID reader.

In an embodiment of the system, the scanner comprises at least one of a Universal Product Code indicia scanner, a Quick Response code scanner, a high-capacity color barcode scanner, and a near-field communication scanner.

In an embodiment of the system, the processor is operable to interact with the server to authenticate the user by matching credentials of the unique identity with a record of the user stored in the database.

In an embodiment of the system, the drug vending machine is locked for further access if the credentials of the unique identity do not match with the record of the user in the database.

In an embodiment of the system, the processor interacts with the server to authenticate the user by matching credentials of the biometric identity with a record of the user stored in the database.

In an embodiment of the system, the drug vending machine is locked for further access if the credentials of the biometric identity do not match with the record of the user in the database.

In an embodiment of the system, the system is installed outside at least one of a pharmacy and a drug store.

In an embodiment of the system, the system is installed outside a box store.

In an embodiment of the system, the system provides an access to the system to refill the prescription into the drug storage.

In an embodiment of the system, the system checks and authenticates dispensing of the drug with an inventory of the drug according to the prescription received; and dispenses the drug container from the drug vending machine.

BRIEF DESCRIPTION OF THE FIGURES

These and other aspects of the present invention will now be described in more detail, with reference to the appended drawings showing exemplary embodiments of the present invention, in which.

DETAILED DESCRIPTION

Definitions and General Techniques

Figure 1:
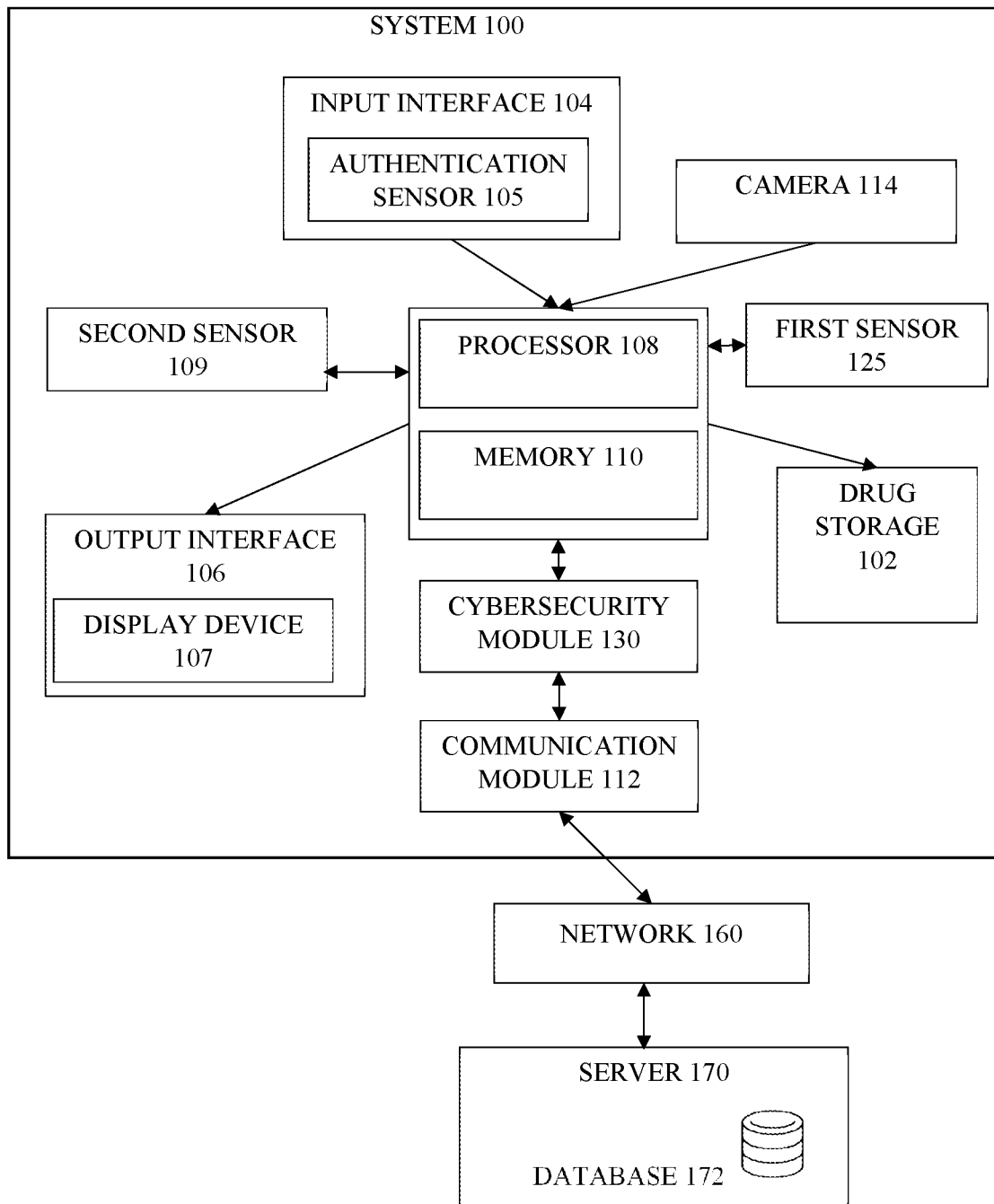
FIG. 1 shows a block level diagram of a system for smart storage.

For simplicity and clarity of illustration, the figures illustrate the general manner of construction. The description and figures may omit the descriptions and details of well-known features and techniques to avoid unnecessarily obscuring the present disclosure. The figures exaggerate the dimensions of some of the elements relative to other elements to help improve understanding of embodiments of the present disclosure. The same reference numeral in different figures denotes the same element.

Although the herein detailed description contains many specifics for the purpose of illustration, a person of ordinary skill in the art will appreciate that many variations and alterations to the details are considered to be included herein.

Accordingly, the embodiments herein are without any loss of generality to, and without imposing limitations upon, any claims set forth. The terminology used herein is for the purpose of describing particular embodiments only and is not limiting. Unless defined otherwise, all technical and scientific terms used herein have the same meaning as commonly understood by one with ordinary skill in the art to which this disclosure belongs.

As used herein, the articles "a" and "an" used herein refer to one or to more than one (i.e., to at least one) of the grammatical object of the article. By way of example, "an element" means one element or more than one element. Moreover, usage of articles "a" and "an" in the subject specification and annexed drawings construe to mean "one or more" unless specified otherwise or clear from context to mean a singular form.

As used herein, the terms "example" and/or "exemplary" mean serving as an example, instance, or illustration. For the avoidance of doubt, such examples do not limit the herein described subject matter. In addition, any aspect or design described herein as an "example" and/or "exemplary" is not necessarily preferred or advantageous over other aspects or designs, nor does it preclude equivalent exemplary structures and techniques known to those of ordinary skill in the art.

As used herein, the terms "first," "second," "third," and the like in the description and in the claims, if any, distinguish between similar elements and do not necessarily describe a particular sequence or chronological order. The terms are interchangeable under appropriate circumstances such that the embodiments herein are, for example, capable of operation in sequences other than those illustrated or otherwise described herein. Furthermore, the terms "include," "have," and any variations thereof, cover a non-exclusive inclusion such that a process, method, system, article, device, or apparatus that comprises a list of elements is not necessarily limiting to those elements, but may include other elements not expressly listed or inherent to such process, method, system, article, device, or apparatus.

As used herein, the terms "left," "right," "front," "back," "top," "bottom," "over," "under" and the like in the description and in the claims, if any, are for descriptive purposes and not necessarily for describing permanent relative positions. The terms so used are interchangeable under appropriate circumstances such that the embodiments of the apparatus, methods, and/or articles of manufacture described herein are, for example, capable of operation in other orientations than those illustrated or otherwise described herein.

No element act, or instruction used herein is critical or essential unless explicitly described as such. Furthermore, the term "set" includes items (e.g., related items, unrelated items, a combination of related items and unrelated items, etc.) and may be interchangeable with "one or more." Where only one item is intended, the term "one" or similar language is used. Also, the terms "has," "have," "having," or the like are open-ended terms. Further, the phrase "based on" means "based, at least in part, on" unless explicitly stated otherwise.

As used herein, the terms "system," "device," "unit," and/or "module" refer to a different component, component portion, or component of the various levels of the order. However, other expressions that achieve the same purpose may replace the terms.

As used herein, the terms "couple," "coupled," "couples," "coupling," and the like refer to connecting two or more elements mechanically, electrically, and/or otherwise. Two or more electrical elements may be electrically coupled together, but not mechanically or otherwise coupled together. Coupling may be for any length of time, e.g., permanent, or semi-permanent or only for an instant. "Electrical coupling" includes electrical coupling of all types. The absence of the word "removably," "removable," and the like, near the word "coupled" and the like does not mean that the coupling, etc. in question is or is not removable.

As used herein, the term "or" means an inclusive "or" rather than an exclusive "or." That is, unless specified otherwise, or clear from context, "X employs A or B" means any of the natural inclusive permutations. That is, if X employs A; X employs B; or X employs both A and B, then "X employs A or B" is satisfied under any of the foregoing instances.

As used herein, two or more elements or modules are "integral" or "integrated" if they operate functionally together. Two or more elements are "non-integral" if each element can operate functionally independently.

As used herein, the term "real-time" refers to operations conducted as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

As used herein, the term "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Other specific forms may embody the present invention without departing from its spirit or characteristics. The described embodiments are in all respects illustrative and not restrictive. Therefore, the appended claims rather than the description herein indicate the scope of the invention. All variations which come within the meaning and range of equivalency of the claims are within their scope.

As used herein, the term "component" broadly construes hardware, firmware, and/or a combination of hardware, firmware, and software.

Digital electronic circuitry, or in computer software, firmware, or hardware, including the structures disclosed in this specification and their structural equivalents, or in combinations of one or more of them may realize the implementations and all of the functional operations described in this specification. Implementations may be as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that encodes information for transmission to a suitable receiver apparatus.

The actual specialized control hardware or software code used to implement these systems and/or methods is not limiting to the implementations. Thus, any software and any hardware can implement the systems and/or methods based on the description herein without reference to specific software code.

A computer program (also known as a program, software, software application, script, or code) is written in any appropriate form of programming language, including compiled or interpreted languages. Any appropriate form, including a standalone program or a module, component, subroutine, or other unit suitable for use in a computing environment may deploy it. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may execute on one computer or on multiple computers that are located at one site or distributed across multiple sites and interconnected by a communication network.

One or more programmable processors, executing one or more computer programs to perform functions by operating on input data and generating output, perform the processes and logic flows described in this specification. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of a digital computer. A processor will receive instructions and data from a read-only memory or a random-access memory or both. Elements of a computer can include a processor for performing instructions and one or more memory devices for storing instructions and data. A computer will also include, or is operatively coupled to receive data, transfer data or both, to/from one or more mass storage devices for storing data e.g., magnetic disks, magneto optical disks, optical disks, or solid-state disks. However, a computer need not have such devices. Moreover, another device, e.g., a mobile telephone, a personal digital assistant (PDA), a mobile audio player, a Global Positioning System (GPS) receiver, etc. may embed a computer. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. Special purpose logic circuitry may supplement or incorporate the processor and the memory.

To provide for interaction with a user, a computer may have a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices provide for interaction with a user as well. For example, feedback to the user may be any appropriate form of sensory feedback, e.g., visual feedback, auditory feedback, or tactile feedback; and a computer may receive input from the user in any appropriate form, including acoustic, speech, or tactile input.

A computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components, may realize implementations described herein. Any appropriate form or medium of digital data communication, e.g., a communication network may interconnect the components of the system. Examples of communication networks include a Local Area Network (LAN) and a Wide Area Network (WAN), e.g., Intranet and Internet.

The computing system may include clients and servers. A client and server are remote from each other and typically interact through a communication network. The relationship of the client and server arises by virtue of computer programs running on the respective computers and having a client-server relationship to each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media accessible by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinct kinds of computer-readable media: physical computer-readable storage media and transmission computer-readable media.

Although the present embodiments described herein are with reference to specific example embodiments it will be evident that various modifications and changes may be made to these embodiments without departing from the broader spirit and scope of the various embodiments. For example, hardware circuitry (e.g., Complementary Metal Oxide Semiconductor (CMOS) based logic circuitry), firmware, software (e.g., embodied in a non-transitory machine-readable medium), or any combination of hardware, firmware, and software may enable and operate the various devices, units, and modules described herein. For example, transistors, logic gates, and electrical circuits (e.g., Application Specific Integrated Circuit (ASIC) and/or Digital Signal Processor (DSP) circuit) may embody the various electrical structures and methods.

In addition, a non-transitory machine-readable medium and/or a system may embody the various operations, processes, and methods disclosed herein. Accordingly, the specification and drawings are illustrative rather than restrictive.

Physical computer-readable storage media includes RAM, ROM, EEPROM, CD-ROM or other optical disk storage (such as CDs, DVDs, etc.), magnetic disk storage or other magnetic storage devices, solid-state disks or any other medium. They store desired program code in the form of computer-executable instructions or data structures which can be accessed by a general purpose or special purpose computer.

As used herein, the term "network" refers to one or more data links that enable the transport of electronic data between computer systems and/or modules and/or other electronic devices. When a network or another communications connection (either hardwired, wireless, or a combination of hardwired or wireless) transfers or provides information to a computer, the computer properly views the connection as a transmission medium. A general purpose or special purpose computer access transmission media that can include a network and/or data links which carry desired program code in the form of computer-executable instructions or data structures. The scope of computer-readable media includes combinations of the above, that enable the transport of electronic data between computer systems and/or modules and/or other electronic devices.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a Network Interface Module (NIC), and then eventually transferred to computer system RAM and/or to less volatile computer-readable physical storage media at a computer system. Thus, computer system components that also (or even primarily) utilize transmission media may include computer-readable physical storage media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter herein described is in a language specific to structural features and/or methodological acts, the described features or acts described do not limit the subject matter defined in the claims. Rather, the herein described features and acts are example forms of implementing the claims.

While this specification contains many specifics, these do not construe as limitations on the scope of the disclosure or of the claims, but as descriptions of features specific to particular implementations. A single implementation may implement certain features described in this specification in the context of separate implementations. Conversely, multiple implementations separately or in any suitable subcombination may implement various features described herein in the context of a single implementation. Moreover, although features described herein as acting in certain combinations and even initially claimed as such, one or more features from a claimed combination may in some cases be excised from the combination, and the claimed combination may be directed to a sub-combination or variation of a sub-combination.

Similarly, while operations depicted herein in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may be integrated together in a single software product or packaged into multiple software products.

Even though particular combinations of features are recited in the claims and/or disclosed in the specification, these combinations are not intended to limit the disclosure of possible implementations. Other implementations are within the scope of the claims. For example, the actions recited in the claims may be performed in a different order and still achieve desirable results. In fact, many of these features may be combined in ways not specifically recited in the claims and/or disclosed in the specification. Although each dependent claim may directly depend on only one claim, the disclosure of possible implementations includes each dependent claim in combination with every other claim in the claim set.

Further, a computer system including one or more processors and computer-readable media such as computer memory may practice the methods. In particular, one or more processors execute computer-executable instructions, stored in the computer memory, to perform various functions such as the acts recited in the embodiments.

Those skilled in the art will appreciate that the invention may be practiced in network computing environments with many types of computer system configurations including personal computers, desktop computers, laptop computers, message processors, hand-held devices, multiprocessor systems, microprocessor-based or programmable consumer electronics, network PCs, minicomputers, mainframe computers, mobile telephones, PDAs, pagers, routers, switches, etc. Distributed system environments where local and remote computer systems, which are linked (either by hardwired data links, wireless data links, or by a combination of hardwired and wireless data links) through a network, both perform tasks may also practice the invention. In a distributed system environment, program modules may be located in both local and remote memory storage devices.

As used herein, the term "API" stands for Application Programming Interface. It is an interface that defines interactions between multiple software applications or mixed hardware-software intermediaries. It defines the kinds of calls or requests that can be made, how to make them, the data formats that should be used, the conventions to follow, etc. It can also provide extension mechanisms so that users can extend existing functionality in numerous ways and to varying degrees. An API can be entirely custom, specific to a component, or designed based on an industry-standard to ensure interoperability. Through information hiding, APIs enable modularity, allowing users to use the interface independently of the implementation. Web APIs are now the most common meaning of the term API. There are also APIs for programming languages, software libraries, computer operating systems, and computer hardware.

The network may dynamically derive the APIs. In other implementations, the APIs may be derived from API records that are stored by the network. Additionally, when new APIs are derived for a particular network service, the APIs may be recorded in case a similar network service request (e.g., from another user) is received, in which case the record may be promptly used to determine the appropriate API, or set of APIs, for the requested network service.

As used herein, the term "Cryptographic protocol" is also known as security protocol or encryption protocol. It is an abstract or concrete protocol that performs a security-related function and applies cryptographic methods often as sequences of cryptographic primitives. A protocol describes usage of the algorithms. A sufficiently detailed protocol includes details about data structures and representations, to implement multiple, interoperable versions of a program.

Secure application-level data transport widely use cryptographic protocols. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation.

Networking switches use cryptographic protocols, like Secure Socket Layer (SSL) and Transport Layer Security (TLS), the successor to SSL, to secure data communications over a wireless network.

As used herein, the term "Logging" is the process of collecting and storing data over a period in order to analyze specific trends or record the data-based events/actions of a system, network, or Information Technology (IT) environment. It enables the tracking of all interactions through which data, files or applications are stored, accessed, or modified on a storage device or application.

As used herein, the term "Dashboard" is a type of interface that visualizes particular Key Performance Indicators (KPIs) for a specific goal or process. It is based on data visualization and infographics.

As used herein, a "Database" is a collection of organized information so that it can be easily accessed, managed, and updated. Computer databases typically contain aggregations of data records or files.

The embodiments described herein can be directed to one or more of a system, a method, an apparatus, and/or a computer program product at any possible technical detail level of integration. The computer program product can include a computer readable storage medium (or media) having computer readable program instructions thereon for causing a processor to carry out aspects of the one or more embodiments described herein. The computer readable storage medium can be a tangible device that can retain and store instructions for use by an instruction execution device. For example, the computer readable storage medium can be, but is not limited to, an electronic storage device, a magnetic storage device, an optical storage device, an electromagnetic storage device, a superconducting storage device, and/or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon and/or any suitable combination of the foregoing. A computer readable storage medium, as used herein, does not construe transitory signals per se, such as radio waves and/or other freely propagating electromagnetic waves, electromagnetic waves propagating through a waveguide and/or other transmission media (e.g., light pulses passing through a fiber-optic cable), and/or electrical signals transmitted through a wire.

Computer readable program instructions described herein are downloadable to respective computing/processing devices from a computer readable storage medium and/or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the one or more embodiments described herein can be assembler instructions, instruction-set-architecture (ISA) instructions, machine instructions, machine dependent instructions, microcode, firmware instructions, state-setting data, configuration data for integrated circuitry, and/or source code and/or object code written in any combination of one or more programming languages, including an object oriented programming language such as Smalltalk, C++ or the like, and/or procedural programming languages, such as the "C" programming language and/or similar programming languages. The computer readable program instructions can execute entirely on a computer, partly on a computer, as a stand-alone software package, partly on a computer and/or partly on a remote computer or entirely on the remote computer and/or server. In the latter scenario, the remote computer can be connected to a computer through any type of network, including a local area network (LAN) and/or a wide area network (WAN), and/or the connection can be made to an external computer (for example, through the Internet using an Internet Service Provider). In one or more embodiments, electronic circuitry including, for example, programmable logic circuitry, field-programmable gate arrays (FPGA), and/or programmable logic arrays (PLA) can execute the computer readable program instructions by utilizing state information of the computer readable program instructions to personalize the electronic circuitry, in order to perform aspects of the one or more embodiments described herein.

Aspects of the one or more embodiments described herein are described with reference to flowchart illustrations and/or block diagrams of methods, apparatus (systems), and computer program products according to one or more embodiments described herein. Each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer and/or other programmable data processing apparatus to produce a machine, such that the instructions, which execute via the processor of the computer or other programmable data processing apparatus, can create means for implementing the functions/acts specified in the flowchart and/or block diagram block or blocks. These computer readable program instructions can also be stored in a computer readable storage medium that can direct a computer, a programmable data processing apparatus and/or other devices to function in a particular manner, such that the computer readable storage medium having instructions stored therein can comprise an article of manufacture including instructions which can implement aspects of the function/act specified in the flowchart and/or block diagram block or blocks. The computer readable program instructions can also be loaded onto a computer, other programmable data processing apparatus and/or other device to cause a series of operational acts to be performed on the computer, other programmable apparatus and/or other device to produce a computer implemented process, such that the instructions which execute on the computer, other programmable apparatus and/or other device implement the functions/acts specified in the flowchart and/or block diagram block or blocks.

The flowcharts and block diagrams in the figures illustrate the architecture, functionality and/or operation of possible implementations of systems, computer-implementable methods and/or computer program products according to one or more embodiments described herein. In this regard, each block in the flowchart or block diagrams can represent a module, segment and/or portion of instructions, which comprises one or more executable instructions for implementing the specified logical function(s). In one or more alternative implementations, the functions noted in the blocks can occur out of the order noted in the Figures. For example, two blocks shown in succession can be executed substantially concurrently, and/or the blocks can sometimes be executed in the reverse order, depending upon the functionality involved. It will also be noted that each block of the block diagrams and/or flowchart illustration, and/or combinations of blocks in the block diagrams and/or flowchart illustration, can be implemented by special purpose hardware-based systems that can perform the specified functions and/or acts and/or carry out one or more combinations of special purpose hardware and/or computer instructions.

While the subject matter described herein is in the general context of computer-executable instructions of a computer program product that runs on a computer and/or computers, those skilled in the art will recognize that the one or more embodiments herein also can be implemented in combination with one or more other program modules. Program modules include routines, programs, components, data structures, and/or the like that perform particular tasks and/or implement particular abstract data types. Moreover, other computer system configurations, including single-processor and/or multiprocessor computer systems, mini-computing devices, mainframe computers, as well as computers, hand-held computing devices (e.g., PDA, phone), microprocessor-based or programmable consumer and/or industrial electronics and/or the like can practice the herein described computer-implemented methods. Distributed computing environments, in which remote processing devices linked through a communications network perform tasks, can also practice the illustrated aspects. However, stand-alone computers can practice one or more, if not all aspects of the one or more embodiments described herein. In a distributed computing environment, program modules can be located in both local and remote memory storage devices.

As used in this application, the terms "component," "system," "platform," "interface," and/or the like, can refer to and/or can include a computer-related entity or an entity related to an operational machine with one or more specific functionalities. The entities described herein can be either hardware, a combination of hardware and software, software, or software in execution. For example, a component can be, but is not limited to being, a process running on a processor, a processor, an object, an executable, a thread of execution, a program and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system and/or across a network such as the Internet with other systems via the signal). As another example, a component can be an apparatus with specific functionality provided by mechanical parts operated by electric or electronic circuitry, which is operated by a software and/or firmware application executed by a processor. In such a case, the processor can be internal and/or external to the apparatus and can execute at least a part of the software and/or firmware application. As yet another example, a component can be an apparatus that provides specific functionality through electronic components without mechanical parts, where the electronic components can include a processor and/or other means to execute software and/or firmware that confers at least in part the functionality of the electronic components. In an aspect, a component can emulate an electronic component via a virtual machine, e.g., within a cloud computing system.

As it is employed in the subject specification, the term "processor" can refer to any computing processing unit and/or device comprising, but not limited to, single-core processors; single-processors with software multithread execution capability; multi-core processors; multi-core processors with software multithread execution capability; multi-core processors with hardware multithread technology; parallel platforms; and/or parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, and/or any combination thereof designed to perform the functions described herein. Further, processors can exploit nano-scale architectures such as, but not limited to, molecular based transistors, switches and/or gates, in order to optimize space usage and/or to enhance performance of related equipment. A combination of computing processing units can implement a processor.

Herein, terms such as "store," "storage," "data store," data storage," "database," and any other information storage component relevant to operation and functionality of a component refer to "memory components," entities embodied in a "memory," or components comprising a memory. Memory and/or memory components described herein can be either volatile memory or nonvolatile memory or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, and/or nonvolatile random access memory (RAM) (e.g., ferroelectric RAM (FeRAM). Volatile memory can include RAM, which can function as external cache memory, for example. By way of illustration and not limitation, RAM can be available in many forms such as synchronous RAM (SRAM), dynamic RAM (DRAM), synchronous DRAM (SDRAM), double data rate SDRAM (DDR SDRAM), enhanced SDRAM (ESDRAM), Synch link DRAM (SLDRAM), direct Rambus RAM (DRRAM), direct Rambus dynamic RAM (DRDRAM) and/or Rambus dynamic RAM (RDRAM). Additionally, the described memory components of systems and/or computer-implemented methods herein include, without being limited to including, these and/or any other suitable types of memory.

The embodiments described herein include mere examples of systems and computer-implemented methods. It is, of course, not possible to describe every conceivable combination of components and/or computer-implemented methods for purposes of describing the one or more embodiments, but one of ordinary skill in the art can recognize that many further combinations and/or permutations of the one or more embodiments are possible. Furthermore, to the extent that the terms "includes," "has," "possesses," and the like are used in the detailed description, claims, appendices and/or drawings such terms are intended to be inclusive in a manner similar to the term "comprising" as "comprising" is interpreted when employed as a transitional word in a claim.

The descriptions of the one or more embodiments are for purposes of illustration but are not exhaustive or limiting to the embodiments described herein. Many modifications and variations will be apparent to those of ordinary skill in the art without departing from the scope and spirit of the described embodiments. The terminology used herein best explains the principles of the embodiments, the practical application and/or technical improvement over technologies found in the marketplace, and/or to enable others of ordinary skill in the art to understand the embodiments described herein.

The following terms and phrases, unless otherwise indicated, shall be understood to have the following meanings.

The term "drug storage" as referred to herein, is a vault or a storage box compliant to the Drug Enforcement Administration (DEA) under 12 CFR 1302.72 which pharmaceutical products and materials are kept, ensuring their stable forms are retained up to the point of use or till it reaches the consumer. The loss of potency during storage may influence the efficacy and safety of pharmaceuticals.

The term "drug" as referred to herein is a chemical which is used as a medicine.

The term "container" as referred to herein is a pharmaceutical container that holds the drug and may be in direct contact with the product. If the container is in direct contact with the drugs it is called an immediate container, or it is a device which holds the drug or the drug product either directly or in an indirect form, i.e., ampoules packed in a container.

The term "drug container" as used herein refers to a container for a pharmacopeial article that is intended to contain a drug substance.

The term "communication module" is a module that facilitates communication, that is, it enables transmission and receiving of data from the input and output interfaces to the processor. It also enables communication between the peripheral devices connected with the processor like display, camera, remote servers, and databases. A communication module may be a wired connection between the components or a wireless communication module.

The term "log record" as used herein is collecting and storing data over a period of time in order to analyze specific trends or record the data-based events/actions of a system, network, or information technology (IT) environment. It enables the tracking of all interactions through which data, files, or applications are stored, accessed, or modified on a storage device or application.

The term "access to the drug" as used herein refers to the ability to take the drug out from the drug storage by an authenticated user.

The term "ledger" as used herein refers to a collection of the transactions recorded. Here transactions mean the quantity of drugs in and out of the drug storage, the number of drugs accessed, the time of access, the quantity of drugs refilled in the drug storage and the balance quantity of the drug remaining in the drug storage.

The term "authentication sensor" as used herein refers to a sensor to perform user authentication and receives the identity of a user attempting to gain access to a network or computing resource by authorizing a human-to-machine transfer of credentials during interactions on a network to confirm a user's authenticity. Authentication sensor keeps unauthorized users from accessing sensitive information.

The term "sensor" as used herein refers to a device that detects or measures a physical property and enables the recording, presentation or response to such detection or measurement using processor and optionally memory. A sensor and processor can take one form of information and convert such information into another form, typically having more usefulness than the original form. For example, a sensor may collect raw physiological or environmental data from various sensors and process this data into a meaningful assessment, such as pulse rate, blood pressure, or air quality using a processor. A "sensor" herein can also collect or harvest acoustical data for biometric analysis (by a processor) or for digital or analog voice communications. A "sensor" can include any one or more of a physiological sensor (e.g., blood pressure, heartbeat, etc.), a biometric sensor (e.g., a heart signature, a fingerprint, etc.), an environmental sensor (e.g., temperature, particles, chemistry, etc.), a neurological sensor (e.g., brainwaves, Electroencephalogram (EEG), etc.), or an acoustic sensor (e.g., sound pressure level, voice recognition, sound recognition, etc.), among others. A variety of microprocessors or other processors may be used herein. Although a single processor or sensor may be represented in the figures, it should be understood that the various processing and sensing functions can be performed by a number of processors and sensors operating cooperatively, or by a single processor and sensor arrangement that includes transceivers and numerous other functions.

As used herein, the term "component" is intended to be broadly construed as hardware, firmware, and/or a combination of hardware and software.

As used herein, the term "API" stands for Application Programming Interface. It is an interface that defines interactions between multiple software applications or mixed hardware-software intermediaries. It defines the kinds of calls or requests that can be made, how to make them, the data formats that should be used, the conventions to follow, etc. It can also provide extension mechanisms so that users can extend existing functionality in several ways and to varying degrees. An API can be entirely custom, specific to a component, or designed based on an industry-standard to ensure interoperability. Through information hiding, APIs enable modularity, allowing users to use the interface independently of the implementation. Web APIs is now the most common meaning of the term API. There are also APIs for programming languages, software libraries, computer operating systems, and computer hardware.

The term "communicatively coupled" as used herein refers to devices connected in a way that permits communication.

The term "controller" as used herein refers to the component of a system that functions as the system controller. A controller typically sends program messages to and receives response messages from devices. A functional unit in a computer system that controls one or more units of the peripheral equipment. Synonym: peripheral control unit. See also: input-output controller; dual channel controller. In robotics, a controller takes as input desired and measured position, velocity or other pertinent variables and whose output is a drive signal to a controlling motor or activator. A device through which one can introduce commands to a control system.

The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to a suitable receiver apparatus.

The term "lock" as used herein refers to a mechanism for keeping a door, window, lid, or container fastened or secured to restrict the access to the contents inside.

The term "activate the lock" as used herein refers to keeping a door, window, lid, or container locked, fastened, or secured to restrict the access to the contents inside.

The term "deactivate the lock" as used herein refers to unlocking a door, window, lid, or container to access the contents inside.

The term "receptacle" as used herein refers to a holder holding a container containing an item. There may be a plurality of receptacles on a shelf of the drug storage. As used herein, receptacles can hold the various original medication containers. Some of the receptacles can be designated as bottle receptacles dimensioned to receive standard sizes of pill bottles, liquid dropper bottles, and the like. Other receptacles can be designated as blister pack receptacles, which are dimensioned to receive pills housed in a blister pack.

The term "cover" refers to a door, a closure, a lid, or a slider to the container holding the contents inside the container.

The term "server" as used herein refers to a computer or system that provides resources, data, services, or programs to other computers, known as clients, over a network. In theory, whenever computers share resources with client machines, they are considered servers. There may be physical servers or virtual servers. The server may be a local server or a remote server.

As used herein, a "database" is a collection of information that is organized so that it can be easily accessed, managed, and updated. Computer databases typically contain aggregations of data records or files.

The term "second level of authentication" used herein refers to the process or action of verifying the identity of a user or process, wherein the identity of the user is verified by corresponding data, in the present application a user may be a patient, a practitioner.

The term "unique identity" as used herein refers to a means of one or more features enabling that person to be distinguished from another data subject.

The term "biometric identification" or "biometric identity" as used herein refers to any means by which a person can be uniquely identified by evaluating one or more distinguishing biological traits. These biological identifiers include fingerprints, hand and earlobe geometries, retina patterns, voice prints and written signatures.

The term "patient" as used herein refers to a person receiving, or registered to receive, medical treatment.

The term "practitioner" as used herein refers to a person who is skilled in the science of medicine. For example, a general practitioner for minor illnesses, a doctor, and a surgeon.

The term "record of practitioners" or "record of user" as used herein refers to a record of the data related to the practitioners in a hospital or clinic, or the patient. The record of practitioner comprises name of practitioner, age of practitioner, gender of the patient, qualification of the practitioner, experience in years, biometric information, unique id information, name of patient to be under the practitioner's supervision.

The term "record of patient" or "record of user" as used herein refers to a record of the data related to the patient undergoing treatment. The record of patient comprises name of patient, age of patient, gender of the patient, a disease, a type of treatment going on, symptoms of the disease, other diseases, allergies, biometric information, unique id information, physiological information, biological marker of patient, drug prescription, scheduled timings to take the drug.

The term "scheduled time" as used herein refers to appointment, assignment, or designation for a fixed time.

The term "physical conditioning parameters" as used herein refers to the environmental condition which affects the contents in the drug storage. The physical conditioning parameters here refer to temperature, humidity, and pressure inside the drug storage.

The term "weight sensor" as used herein refers to a type of transducer, specifically a weight transducer. It converts an input mechanical force such as load, weight, tension, compression, or pressure into another physical variable, in this case, into an electrical output signal that can be measured, converted, and standardized.

The term "RFID tag" and "RFID tag reader" as used herein refers to Radio Frequency Identification (RFID) tags and readers that use electromagnetic fields to automatically identify and track tags attached to objects. An RFID system comprises a tiny radio transponder, a radio receiver and transmitter. When triggered by an electromagnetic interrogation pulse from a nearby RFID tag reader device, the tag transmits digital data, usually an identifying inventory number, back to the reader. This number can be used to track inventory goods. Passive tags are powered by energy from the RFID tag reader's interrogating radio waves.

The term "IR sensor" as used herein refers to sensors transmitting and receiving infrared (IR) waves. If an object moves in between, the receiving data of the IR sensor changes, and the output of the IR sensor changes its state. It is used to detect an obstacle or access to an object.

The term "photodiode" as used herein refers to a semiconductor diode which, when exposed to light, generates a potential difference, or changes its electrical resistance.

The term "prescription detail" used herein refers to a name of the drug, an amount of drug taken at any one time and the time to take the drug. A dose is a measured quantity of a medicine, nutrient, or pathogen which is delivered as a unit. The greater the quantity delivered, the larger the dose. Doses are most commonly measured for compounds in medicine. The term is usually applied to the quantity of a drug or other agent administered for therapeutic purposes but may be used to describe any case where a substance is introduced to the body.

The term "controlled substance" as used herein refers to a drug or chemical whose manufacture, possession, and use is regulated by a government, such prescription medications that are designated by law.

The term "opioid" as used herein refers to a compound resembling opium properties or effects.

The term "narcotic" as used herein refers to a drug or other substance that affects mood or behavior and is consumed for non-medical purposes.

The term "psychedelic drug" as used herein refers to a psychotomimetic drug or hallucinogen, any of the so-called mind-expanding drugs that are able to induce states of altered perception and thought, frequently with heightened awareness of sensory input, but with diminished control over what is being experienced.

The term "official" as used herein refers to a person holding public office or having official duties, especially as a representative of an organization or government department. The definition of official is someone authorized or someone who holds a position of authority.

The term "third party official" as used herein refers to a person or group besides the two primarily involved in a situation. Here the person who is not directly involved with the clinic or hospital that uses the system for smart medical storage.

The term "authorized owner" as used herein refers to a person approved or assigned by the employer to perform a specific type of duty or duties or to be at a specific location or locations at the jobsite.

The term "unbiased monitoring" used herein refers to observing, checking, or maintaining regular surveillance over something over a period of time; keeping something under systematic review. It may be referred to as keeping an eye on, or keeping track of, something.

The term "in communication with" as used herein, refers to any coupling, connection, or interaction using electrical signals to exchange information or data, using any system, hardware, software, protocol, or format, regardless of whether the exchange occurs wirelessly or over a wired connection.

The term "module" as used herein refers to a set of standardized or independent units/parts that can be used to construct a more complex structure. A module is a combination of both hardware units and software programs to control hardware units. It refers to any known or later developed hardware, software, firmware, artificial intelligence, fuzzy logic, or combination of hardware and software that is capable of performing the functionality associated with that element.

The term "quantity of drug" as used herein refers to dosage of the drug administered to a subject at a given time or over a cumulative period of time.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers— say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that an authorized user can only decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damage data, steal data, or disrupt digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attack, data breaches, Denial of Service (DoS) attacks, and other attack vectors.

The term "hash value" used herein can be thought of as fingerprints for files. The contents of a file are processed through a cryptographic algorithm, and a unique numerical value—the hash value—is produced that identifies the contents of the file. If the contents are modified in any way, the value of the hash will also change significantly. Example algorithms used to produce hash values are Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application. Data integrity refers to the accuracy and consistency (validity) of data over its lifecycle. Compromised data is of little use to enterprises, not to mention the dangers presented by sensitive data loss.

The term "alarm" as used herein refers to a trigger when a system or a component in a system fails or does not perform as expected. A system may enter an alarm state when certain events occur. An alarm indication signal is a visual signal to indicate the alarm state. For example, the heart rate is very low, a light emitting diode (LED) may glow red alerting that it is beyond the specified limits and turns green when the heart rate is within specified limits. Another example could be when a cyber security threat is detected, a network administrator may be alerted via a sound alarm, a message, a glowing LED, a pop-up window, etc. Alarm indication signals may be reported downstream from a detecting device, to prevent adverse situations or cascading effects.

The term "in communication with" as used herein refers to any coupling, connection, or interaction using electrical signals to exchange information or data, using any system hardware, software, protocol, or format, regardless of whether the exchange occurs wirelessly or over a wired connection.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

As used herein, the term "perimeter network" refers to a network closest to a router that is not under the enterprise or organization control. Usually, a perimeter network is the final step a packet takes traversing one of your networks on its way to the internet; and conversely the first network encountered by incoming traffic from the Internet. A network perimeter is a secured boundary between the private and locally managed side of a network, often a company's intranet, and the public facing side of a network, often the Internet. The boundary is defined as a perimeter network.

As used herein, the term "network" may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers. Cloud servers are located in data centers all over the world. By using cloud computing, users and companies don't have to manage physical servers themselves or run software applications on their own machines.

As used herein, the term "system hardening" is a collection of tools, techniques, and best practices to reduce vulnerability in technology applications, systems, infrastructure, firmware, and other areas. The goal of system hardening may be to reduce security risk by eliminating potential attack vectors and condensing the system's attack surface.

As used herein, the term "SHA256" stands for Secure Hash Algorithm 256-bit is a hash function and it is used for cryptographic security. Cryptographic hash algorithms produce irreversible and unique hashes. The larger the number of possible hashes, the smaller the chance that two values will create the same hash.

An embodiment may relate to a system comprising a drug storage comprising a container to hold a drug container comprising a drug, a processor, a memory, a communication module, and a cyber security module. The processor is communicatively coupled with the memory. The processor is operable to log a record of access to the drug container and to maintain a ledger of the record of access to the drug container using blockchain technology. The system is secured through a cyber security module. The system is in communication with a server through the communication module. The server comprises a database. The server comprises at least one of a local server, a remote server, and a cloud server.

In an embodiment, FIG. 1 shows a block level diagram of a system 100 for smart storage. The system comprises: a drug storage 102 comprising a container to hold a drug container that comprises a drug inside, an input interface 104 comprising an authentication sensor 105, an output interface 106 comprising a display device 107, a first sensor 125, a second sensor 109, a camera 114, a processor 108, a memory 110, wherein the processor 108 is communicatively coupled with the memory 110, a communication module 112, and a cyber security module 130. The output interface also may comprise a buzzer, speaker, and an alarm. The system is in communication with the server 170 through the communication module 112. The server 170 comprises at least one of a local server, a remote server, and a cloud server. The communication module 112 connects to the server 170 through the network 160. The server comprises a database 172.

The communication module 112 can include multiple communication protocols, such as Bluetooth, 802.11a/b/g/n, and Code Division Multiple Access (CDMA), Global System for Mobile (GSM) communications and 3G/4G/4G Long-Term Evolution (LTE) mobile phone communication protocols. Mobile phone communication protocols (such as 802.11a/b/g/n) can be utilized by the processor 208 to contact the server for retrieving medication information relating to drug interactions, administering information, etc. In one embodiment, a cable, such as a network cable with an RJ45 connector, can be used to communicate to devices external from the drug storage 202. The communication module 112 and/or the cable can allow the system 100 to contact a treating health organization through the communication module 112 to relay medication compliance information and other related information regarding the patient's health records. The processor 108 may be configured to provide encryption and decryption when sending or receiving personal health-related information in order to maintain patient privacy; in one embodiment the data will be HIPAA (Health Insurance Portability and Accountability Act) compatible. In one embodiment, the processor 108 allows sharing of data regarding compliance, errors, and device malfunction. In addition, the processor 108 performs updates and changes (to the system, to current therapies, and the like) through the server.

In an embodiment of the system, the system further comprises an input interface, an output interface, and a camera. The processor is operable to receive, through the input interface, a unique identity, and a biometric identification of a user. The input interface comprises an authentication sensor, a keypad, a touchpad, a scanner, and an RFID tag reader; and wherein the scanner comprises a Universal Product Code indicia scanner, a Quick Response code scanner, a high-capacity color barcode scanner, and a near-field communication scanner. The output interface comprises an LED display, an LCD display, a buzzer, an alarm, and a speaker.

In an embodiment of the system, drug storage further comprises a lock associated with the container; a receptacle having at least a first sensor to detect the access to the drug container. The lock and the first sensor are communicatively coupled with the processor of the system to selectively activate and deactivate the lock. The drug storage comprises a cover for the container. The cover comprises at least one of a lid, a door, a hinged cover, a magnetic cover, and a sliding door.

Figure 2A:
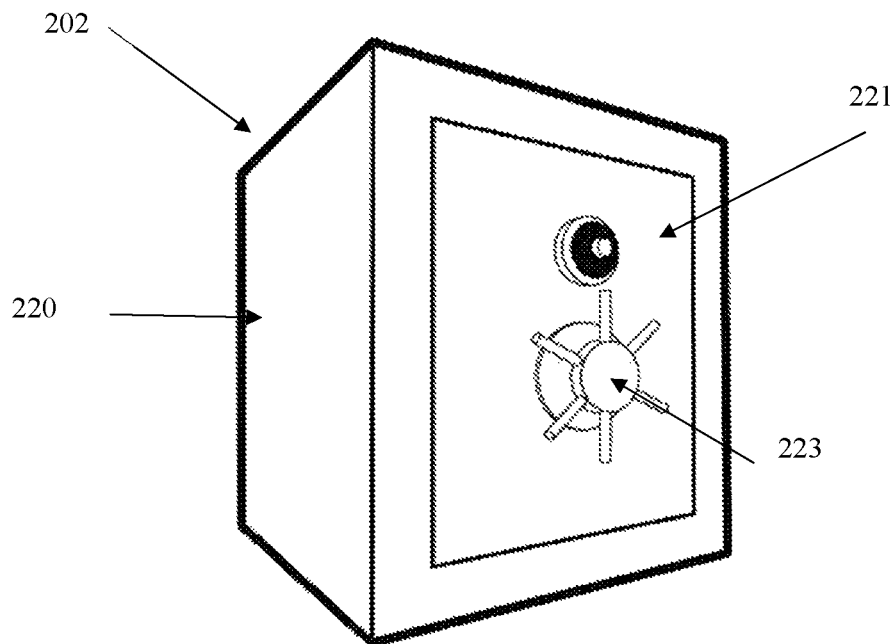
FIG. 2A shows a detailed diagram of the drug storage.

In an embodiment, as shown in FIG. 2A, the drug storage 202 comprises a cover 221 to the container 220. The cover 221 to the container 220 comprises at least one of a lid, a door, a hinged cover, a magnetic cover, and a sliding door. The drug storage further comprises a lock 223 associated with the container 220 which is communicatively coupled with the processor of the system to selectively activate and deactivate the container to allow an opening of the container.

Figure 2B:
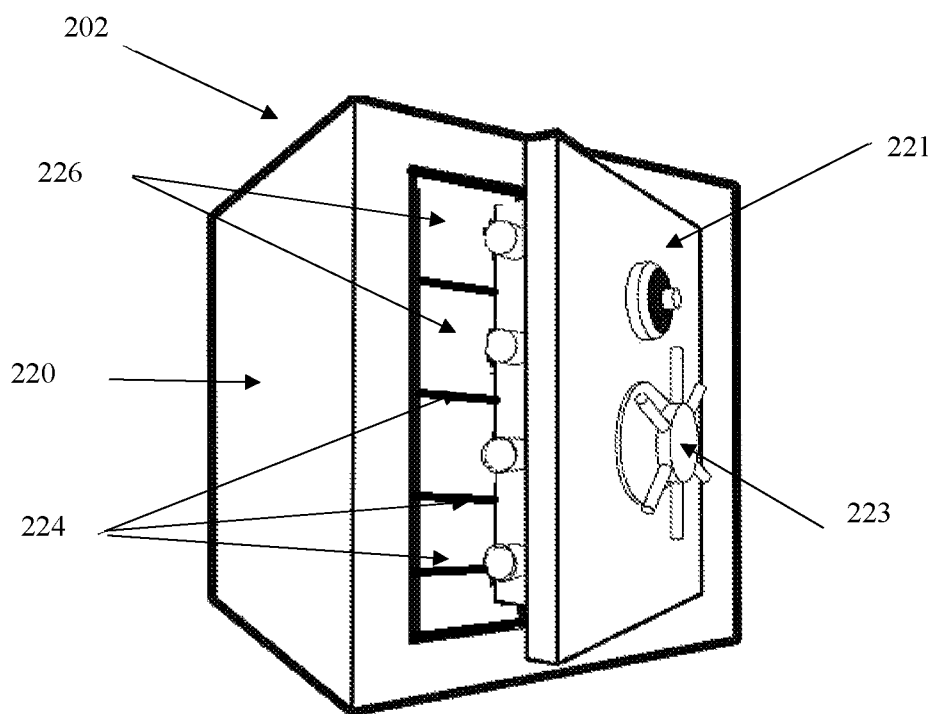
FIG. 2B shows a perspective view of an opened drug storage.

In the open configuration, the container 220 of the drug storage 202 may be filled with drug containers comprising vials, syringes, pillboxes, and the like. FIG. 2B illustrates the internal components contained within the drug storage, in at least one embodiment. In that regard, it should be noted that the particular size, shape, and dimensions of the container 220 shown in the drawings is merely exemplary and is shown for illustrative purposes. In further embodiments, the container 220 may take on any other size, shape or dimension now known or later conceived—for example, a square or rectangular box, a vault, an oval container, an oblong container, a cylindrical container, or a pen-shaped container. In an embodiment, FIG. 2B shows the detailed perspective view of the drug storage. The drug storage comprises container 220 to hold a drug. The container 220 may comprise shelves 224 with different compartments 226 to hold the drug. The drug storage 202 comprises a cover 221 to the container 220. The cover 221 to the container 220 comprises at least one of a lid, a door, a hinged cover, a magnetic cover, and a sliding door.

Figure 2C:
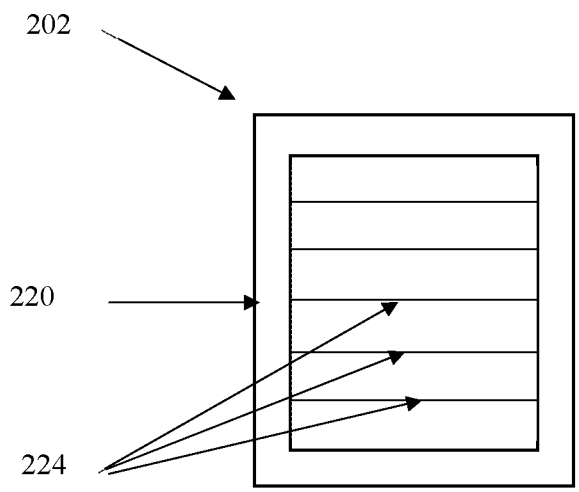
FIG. 2C shows a front view of the opened drug storage.

FIG. 2C shows a front view of the container 220 without the cover 221. As shown in FIG. 2C, the shelves 224 with different compartments 226 to hold the drugs are clearly shown. The shelves 224 may further comprise slidable shelves for easy access to a drug and may comprise trays having different slots to keep the drugs safe without any movement when the drug storage 202 is in transport.

In an embodiment of the system, the lock is activated by a second level of authentication by the user. The unique identity of the user comprises at least one of a unique identification number, an RFID tag, a password, and an unlocking pattern. The biometric identification of the user comprises at least one of a fingerprint, an eyeblink, a retina scan, an iris scan, a facial image scan and an eye scan. The user is one or more of a patient, a practitioner, a technician, and an authorized owner of the system. The second level of authentication comprises the unique identity of the user and the biometric identification of the user.

In an embodiment of the system, the processor is operable to interact with the server to authenticate the user by matching credentials of the unique identity with a record of practitioners and a record of patients stored in the database. The drug storage is locked for further access if the credentials of the unique identity do not match with the record of practitioners and the record of patients in the database.

In an embodiment of the system, the processor is operable to interact with the server to authenticate the user by matching credentials of the biometric identification with a record of practitioners and a record of patients stored in the database. The drug storage is locked for further access if the credentials of the biometric identification do not match with the record of practitioners and the record of patients in the database.

Figure 2D:
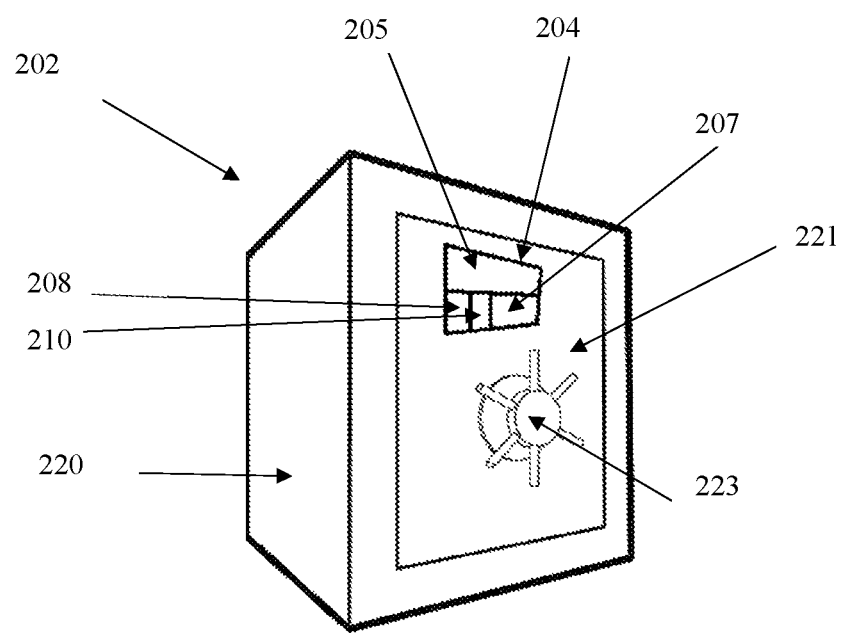
FIG. 2D shows an embodiment of the system for smart storage.

In an embodiment, FIG. 2D shows the drug storage 202 comprising the input interface 204, authentication sensor 205, the output interface 207, processor 208, memory 210, the cover 221, and the communication module embedded in the drug storage. The drug storage 202 comprises the authentication sensor 205 that is in direct communication through the communication module with the processor 208 and memory 210 to activate and deactivate the lock of the drug storage. As described herein, the drug storage includes a lock 223 to control access into the drug storage. The lock 223 is always activated by the processor to prevent access into the container of the drug storage and items stored therein. During operation, the drug storage may be unlocked/deactivated upon authentication of a user. The input interface 204, authentication sensor 205, the output interface 207, the processor 208 and the memory 210 are mounted on the cover 221 to the container 220 of the drug storage 202. The input interface comprises an authentication sensor, a keypad, a touchpad, a scanner, and an RFID tag reader. The scanner comprises a Universal Product Code indicia scanner, a Quick Response code scanner, a high-capacity color barcode scanner, and a near-field communication scanner. The output interface comprises an LED display, an LCD display, a buzzer, an alarm, and a speaker.

Figure 2E:
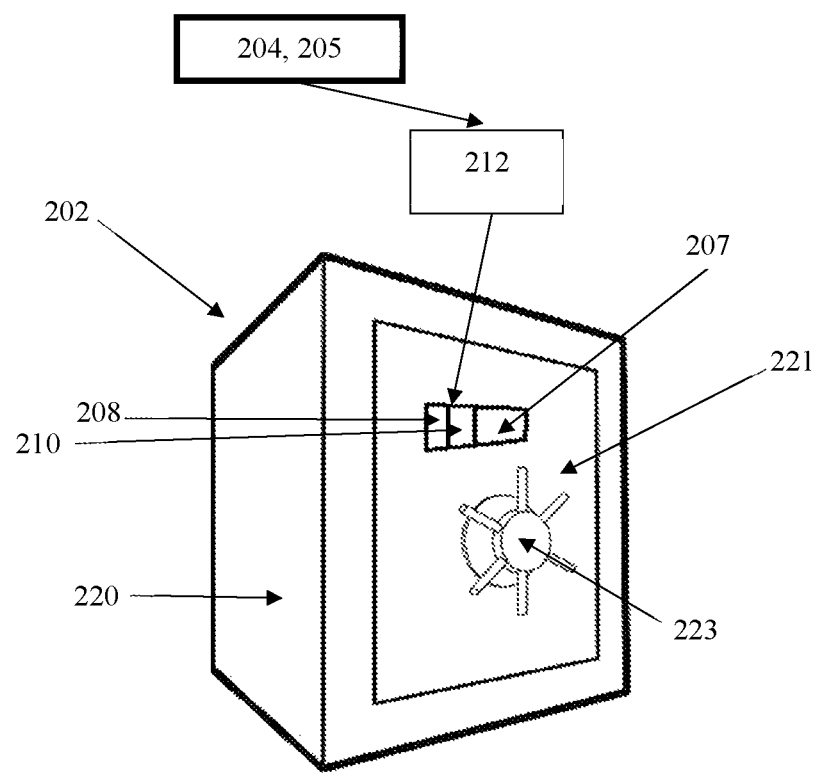
FIG. 2E shows another embodiment of the system for smart storage.

In an embodiment, FIG. 2E shows the input interface 204 remotely located. The input interface 204 is inside a remote device aiding remote access to the drug storage. The input interface 204 and the output interface 207 may also include an application programming interface and a web application connected with the authentication sensor 205 as the mobile devices and computers have biometric sensors for biometric information of the user. The application programming interface and a web application may also have a unique identity to be set for the access to the drug from the drug storage. The processor 208 is configured to be in communication with the authentication sensor 205 through the communication module 212 which facilitates communication with the server and the drug storage 202.

In an embodiment, the input interface 204, the output interface 207, the processor 108, the memory 210, and the lock 223 are added or retrofitted to an existing drug storage to add access control to the drug storage. In some applications, the drug storage 202 may include the input interface 204, the processor 208, the memory 210, and the lock 223 in the original manufacture or assembly.

In an embodiment, the authentication sensor 205 is inside a remote device aiding remote access to the drug storage 202. The authentication of the user may also include authentication through an application programming interface and a web application connected with the authentication sensor as the mobile devices and computers have a biometric sensor for a biometric information of the user. The application programming interface and a web application may also have a unique identity to be set for the access to the drug from the drug storage. The processor 208 is configured to be in communication with the authentication sensor 205 through the communication module 212 which facilitates communication with the server and the drug storage 202. The communication module 212 comprises any suitable wireless technology such as cellular which can include but is not limited to Global System for Mobile communication, Code Division Multiple Access, Wireless in Local Loop, General Packet Radio Services, or it can also utilize Low Power Wide Area Networks (LPWANs) such as Bluetooth, Bluetooth low energy, Wi-Fi, Z-Wave, Thread and Zigbee.

In an embodiment, the communication module 212 may comprise a wired connection such as LAN, WLAN and WAN.

In an embodiment, the processor 208 is configured to receive, through the input interface 204, a unique identity, and a biometric identification of a user through the authentication sensor 205. The authentication sensor 205 is at least one of a fingerprint scanner, a facial recognition system (i.e., a camera with corresponding facial recognition software), an iris scanner, and a retinal scanner. In still further embodiments, the authentication sensor may be any other type of biometric sensor now known or later developed.

In an embodiment, the input interface 204 may receive the unique identity of the user comprising at least one of a unique identification number, an RFID tag, a password, and an unlocking pattern.

In an embodiment of the system, the user has a predefined count of access to the drug container allowed in a day. The user is allowed to access the drug container at a scheduled time. The access to the drug container in the drug storage is synchronized with a scheduled time of use of the drug container by the user.

In an embodiment of the system, the access to the drug container in the drug storage gets locked for the user that exceeds the predefined count of the access to the drug container in the day. An authorized owner of the system is able to unlock the access to the drug container in the drug storage.

In an embodiment of the system, the system comprises a second sensor to sense physical conditioning parameters comprising at least one of a temperature, a pressure, a humidity inside the drug storage in order to monitor a state of preservation of the drug present in the container.

In an embodiment of the system, the camera is operable to monitor the access to the drug container by the user.

In an embodiment, the container 220 is deactivated by a second level of authentication. The second level of authentication comprises a unique identification and a biometric identification. In the case of the patient's second level of authentication, the unique identity and the biometric identification of a patient is received. In the case of the practitioner's second level of authentication, the unique identity and the biometric identification of a practitioner is received.

In an embodiment, the processor 208 is configured to interact with the server to authenticate the user by matching credentials of the unique identity against a record of practitioners and a record of patients stored in the database. The processor 208 is configured to interact with the server to authenticate the user by matching credentials of the biometric identification against a record of practitioners and a record of patients stored in the database. The record of patient comprises a name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The record of practitioner comprises name of practitioner, age of practitioner, gender of the practitioner, qualification of the practitioner, experience in years, biometric information, unique identity information, name of patient under the practitioner's supervision. The biometric identification and the unique identity of the user is pre-stored in the database for the matching of credentials. The biometric identification and the unique identity are stored in the database when the user registers himself for the first time in the system. The system may ask for registration for a first-time user, the registration of the patient comprises name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The registration of a practitioner comprises name of practitioner, age of practitioner, gender of the practitioner, qualification of the practitioner, experience in years, biometric information, unique identity information, name of patient under the practitioner's supervision. The registration of the user may only be accepted and completed by the authorized owner of the system.

The processor 208 is configured to deactivate the lock of the drug storage 202 to allow the user to access the drug container from the drug storage 202. The access to the drug container from the drug storage 202 is monitored by the camera. The camera could also be attached to the drug storage 202 and a picture of the drug container being accessed is transferred to the processor 208 and compared to the record in prescription details in the database to ensure that the drug container accessed is the correct drug that has been directed to be accessed by the user. In case of a wrong drug container accessed, or an indefinite number of drug containers accessed, the camera captures the image of the drug as well as the user, and the processor 208 is configured to raise an alarm to notify the practitioners and the authorized owners of the system of a misuse or illegal access to the drug container.

The access to the drug container in the drug storage 202 is synchronized with the scheduled time for the access to the drug for a user. After receiving the user information through the authentication sensor, the scheduled time to access the drug container for the user is also checked. The drug storage is unlocked only if the time of access to the drug container is the scheduled time for the access to the drug container for the user. The system would not allow access to the drug container to the user if the scheduled time for the access do not match with the time in real time. In case the scheduled time for the access to the drug container do not match with the time in real time, the system raises an alarm to notify the practitioners and the authorized owners of the system of a misuse or inappropriate request to access the drug.

In an embodiment, the access to the drug container in the drug storage 202 is locked for further access if the credentials of the biometric identification and the unique identity do not match with the record of practitioners and the record of patients in the database. An authorized owner of the system is able to unlock the access to the drug container in the drug storage 202. The user has a predefined number of accesses to the drug containers in a day. If the number of accesses exceeds in a day and if a request to access the drug container is received other than a scheduled time, then the access to the drug container in the drug storage 202 is locked for further access.

In an embodiment, the drug comprises at least one of a controlled substance, an opioid, a narcotic drug, and a psychedelic drug.

In an embodiment, the output interface comprises a display screen. The display screen may be a liquid crystal display (LCD), an e-paper/e-ink display, or an organic LED (OLED) display, or other displays as known to one skilled in the art. The display screen may function to provide usage instructions to the patient, as well as alerts, such as time to take a medication, expiration of a medication, warnings, etc. The display screen may also be equipped with a touch sensitive interface that enables user interaction between the drug storage cover and the patient. For example, the patient/user can input information related to a scanned medication by way of the touch interface when prompted on the display screen. In one embodiment, a second display screen may be placed on an outer surface of the drug storage 202. This second display screen can be a high-density color LCD display capable of displaying a color image of the medication, e.g., a pill that the patient is scheduled to take, so that the patient can be assured that he is taking the correct pill. For example, the patient is notified that it is time to take medication. The slot containing the medication, due to be taken, is illuminated, or otherwise indicated. The patient removes the bottle of medication and removes one of the pills, and the image of the pill is displayed on the color LCD screen. The patient is directed to compare the pill in hand with the pill on the screen to assure that it is the same pill. The direction to the patient can be given audibly and/or visually on the display screen.

Figure 2F:
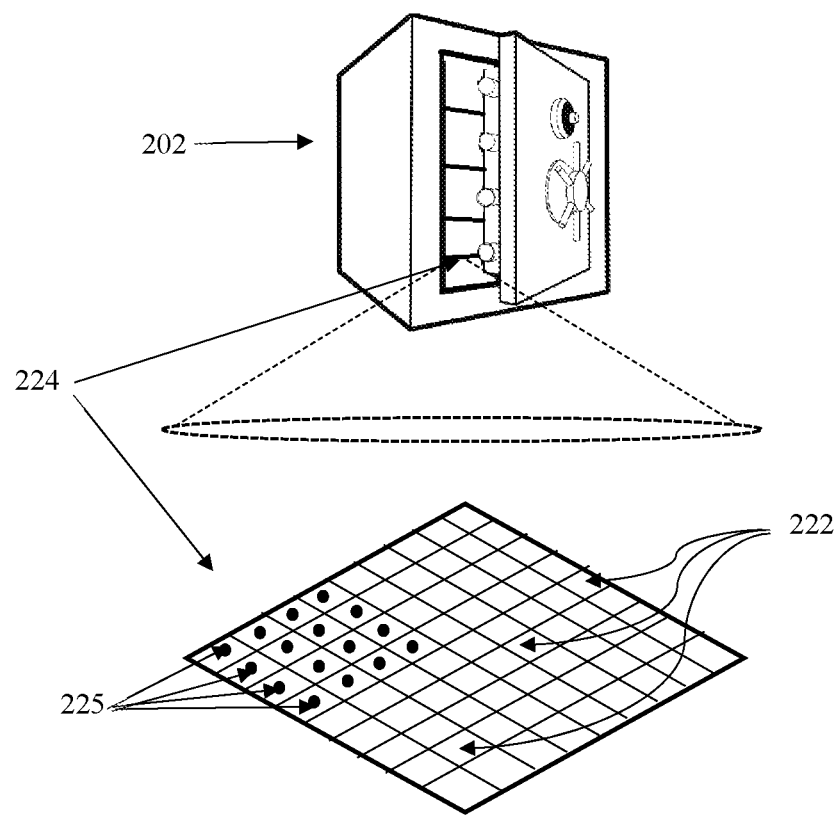
FIG. 2F shows an exploded view of the receptacles on the shelves of the system for smart storage.

In an embodiment, FIG. 2F shows an exploded view of the shelves of the container comprising a receptacle 222. The drug storage comprises a receptacle 222 comprising a first sensor 225 to detect the access to the drug. The receptacle 222 is placed on the base of every shelf or compartment of the container 220 to detect the access to the drug. The receptacles 222 may hold the various original medication containers. Some of the receptacles may be designated as bottle receptacles and dimensioned to receive standard sizes of pill bottles, liquid dropper bottles, and the like. Other receptacles can be designated as blister pack receptacles, which are dimensioned to receive pills housed in a blister pack. An individual medication bottle holder receptacle may contain a securing mechanism, such as spring-loaded sides to hold the drug. The spring-loaded sides, for example, can apply tension to the original medication container and keep it tightly fitted in the slot to hold the drug and greatly decrease the chances that the original medication container falls out of the slot during movement and/or transport of the drug storage 202. Other mechanisms for securing the original medication container in the slot can also be used.

In an embodiment of the system, to detect the access to the drug container, the first sensor comprises at least one of a weight sensor, an RFID tag reader, an IR sensor, a photodiode, and an indicator tag on the drug container to detect the access to the drug container from the container. In an embodiment of the system, the weight sensor is operable to send a weight value to the server in cases of access to the drug container. The weight value is compared with a weight of the drug container from prescription details in the database to determine if the access to the drug container is secure. The weight of the drug container in the prescription details in the database is updated after the access to the drug container.

In an embodiment, the first sensor comprises at least one of a weight sensor, an RFID tag reader, an IR sensor, and an indicator tag to detect the access to the drug from the container.

In an embodiment, the weight sensor is operable to send a weight value of the drug container accessed to the server in cases of access to the drug container. The weight value is compared with a weight of the drug container from prescription details in the database to determine if the access to the drug container is secure. The weight of the drug container in the prescription details in the database is updated after the access to the drug.

In an embodiment, the receptacle 222 of the shelf in the drug storage is equipped with a scale which measures the weight value of the drug container which can then be transferred to the processor 208 and compared to a record of the weight of the drug in the prescription details in the database and used as a quality control means to ensure that the drug accessed is the correct drug and is in the right quantity. Alternatively, the camera may also be attached to the drug storage and a picture of the accessed drug could be transferred to the processor 208 and compared to the record in the prescription details in the database to ensure that the drug accessed by the user is the correct drug and is in the right quantity as the weight of the drug in the prescription details in the database.

The processor 208 compares the weight value measured of the drug container and the weight of the drug container in the prescription details in the database to verify that the drug container accessed is the correct drug container and is in the right quantity. If the drug container accessed is not the correct drug container and the quantity of the drug container is more than the quantity in the prescription details, then the processor 208 sets an alert and sends an alarm to the practitioner through at least one of speaker, buzzer, and a display device. Alternatively, the camera may also be attached to the drug storage and a picture of the accessed drug container could be transferred to the processor 208 and compared to the record in the prescription details in the database to ensure that the drug accessed by the user is the correct drug and is in the right quantity as the weight of the drug container in the prescription details in the database. If the drug accessed is not the correct drug and the quantity of the drug, via the drug container weight, is more than the quantity in the prescription details, then the processor 208 sets an alert and sends an alarm to the practitioner through at least one of speaker, buzzer, and a display device.

In an embodiment of the system, the drug container comprises an RFID tag. An RFID tag reader detects a change in data of the RFID tag and communicates the change in data to the processor, wherein the processor reports a number of drug containers accessed to the server by the communication module in cases of changes in the data received.

In an embodiment the drug container is labeled by the RFID tag to trace. The container 220 has drugs stored with an RFID tag on the drug container. When the container is refilled, the drug container that is to be stored in the container 220 is assigned a new RFID tag and an identification number of the RFID tag is saved into the database. Each RFID tag has a separate identification number. The identification number of the RFID tag of the drug container stored in the container 220 is saved in the database. The first sensor of the receptacle comprises an RFID tag reader to read the RFID tags. When the drug containers with RFID tags are in the container 220 the processor continuously receives a value of the identification number of the RFID tags through the RFID tag reader. The processor 208 compares the received value with the saved identification numbers in the database. When there is access to the drug container, a particular identification number will then not be read by the RFID tag reader as the drug container has been accessed, removed. In such cases, the processor 208 detects a change in data of the RFID tag as an identification number of the drug container accessed is no longer received by the processor 208. The processor 208 reports a count of drug containers accessed to the server by the communication module in cases of the change in the data received. In case more than one drug container is accessed, the identification number of more than one drug container is not received by the processor 208. In case an illicit number of drug containers are accessed at a time, the system raises an alarm to alert the authorized owner of the system and a practitioner to alert the possible misuse of the drug container. The illicit number of the drug container may be the quantity of drug containers more than the prescribed quantity of drug containers that were accessed at the scheduled time. The processor checks the quantity of drug containers accessed, the scheduled time of delivering the drug, the prescription quantity of the drug containers by interacting with the database on the server and then raises an alarm if any of the quantity of the drug containers or the scheduled time to access the drug containers do not match with the database.

In an embodiment, an RFID location tracking system with real-time data on the status and movement of a drug container is used. Such technology is built on active RFID technology. Active RFID location tracking systems allow tracking the real-time movement of the drug containers throughout a monitored area. The system may track RFID tags from afar with the highest accuracy. This data is sent along with the location signal to the RFID tag reader. Active RFID location tracking uses powered tags, which contain an internal battery. This energy source allows the tag to send out a strong, continuous signal that an RFID tag reader can pick up. Most RFID tags have batteries that can provide power for weeks or months before needing to be recharged. The information picked up by an RFID tag reader is sent to a computer containing RFID location tracking system software. It interprets the data and displays it on the dashboard as a moving image on an overlay of the building map. With the map screen open, the signals from active ID tags ping off locators throughout the monitored area. These active RFID tags will be shown moving second-by-second around the monitored area.

In an embodiment of the system, the drug container comprises the indicator tag comprising at least one of a Universal Product Code indicia, a Quick Response code, a high-capacity color barcode, and a near-field communication tag on the drug container.

In an embodiment of the system, the first sensor comprises a scanner to scan at least one of the Universal Product Code indicia, the Quick Response code, the high-capacity color barcode, and the unpowered near-field communication tag.

In an embodiment of the system, the indicator tag is utilized to identify the drug container.

In an embodiment of the system, the indicator tag comprises a detail of the drug comprising a batch number, an inventory count of the drug container, a name of the drug, an expiry date, and a disease it is used to treat.

In an embodiment of the system, the detail of the drug is sent to the server on each of the access to the drug container from the drug storage in order to track the access to the drug container.

In an embodiment of the system, the system is a Drug Enforcement Administration compliant system.

In an embodiment, the drug container comprises the indicator tag comprising at least one of a Universal Product Code indicia, a Quick Response code, a high-capacity color barcode, and a near-field communication tag on a casing of the drug in order to trace the drug. The indicator tag may be placed on the covering of the drug. When the container 220 is refilled, the drug container that is to be stored in the container 220 is assigned a new indicator tag on each drug container stored in the drug storage. The indicator tag comprises a detail of the drug comprising an inventory number of the drug, a name of the drug, an expiry date, and a disease it is used to treat. The indicator tag is scanned by a scanner. The first sensor comprises a scanner to scan the Universal Product Code indicia, the Quick Response code, the high-capacity color barcode, and the unpowered near-field communication tag. The information of the drug is stored on the indicator tag. The information of the drug is stored in the database through the scanner for the first time when the indicator tag is assigned to each drug. When the drug container is accessed from the drug storage, the scanner reads the information of the drug container accessed. The information of the drug container accessed is checked with the information of the drug container stored in the database, the prescription quantity, and the scheduled time. If the quantity of the drug container accessed is more than the prescription quantity or the access to the drug containers is not on the scheduled time, then the alarm is raised to notify the authorized owner of the system and the practitioner who is supervising the patient for a potential misuse of the drug.

In an embodiment, the first sensor may also comprise at least one of an IR sensor and a photodiode that upon access to the drug container gives a change in the output of the IR sensor or the photodiode indicating the access to the drug. Each compartment of the container has the IR sensor or the photodiode. The quantity of drug containers accessed is recognized from the count of IR sensors or photodiodes showing the change in output. This change in output is compared with the prescription quantity of the drug containers in the database. If the quantity of drug containers accessed is more than the prescription quantity of the drug containers in the database at a scheduled time, or the time do not match with the scheduled time, then the alarm is raised to notify the authorized owner of the system and the practitioner who is supervising the patient for a potential misuse of the drug.

In an embodiment, the processor may also select an available receptacle 222 to receive the new or refilled drug and can indicate the selection by illuminating an LED associated with the selected receptacle 222. The first sensor, such as a photodiode and LED assembly, disposed inside each of the receptacles 222 may be triggered when the original medication container is received by the selected receptacle 222. Other sensors, as known to one skilled in the art, can also be used. The trigger of the sensor is received by the processor 208 which verifies that the original drug has been placed in the correct receptacle 222. The processor associates the receptacle assignment, e.g., location, with the drug held in the container and stored in the assigned receptacle, e.g., location, in the database.

The processor 208 may indicate a time to access the drug by referring to inputted information by the patient/user or based on known interactions with other prescribed medications under the system. For example, if medication A and medication B should not be taken together, the processor 208 adjusts the scheduled time accordingly. In one embodiment, time can be tracked by a clock circuit. Moreover, the processor may adjust the scheduled time according to the schedule of the patient so that a patient is not alerted to access the drug container during pre-set sleep hours, for example between 11 PM and 8 AM, or other time intervals set by the patient. The patient may set his own sleep hours by the input interface.

In an embodiment, if the user forgets to access the drug container at the scheduled time, the user is notified by a notification means such as a buzzer or short-range wireless communication provided by a wireless communication circuit, such as Bluetooth, in communication with a paired bracelet, e.g., wrist alert, or fob, which can be worn, for example, as a pendant. In one embodiment, the notification can occur when the bracelet or pendant lights up and/or vibrates. Other notification means can also be used. Additionally, the processor 208 may activate the LED corresponding to the receptacle 222 holding the medication to be taken. If the patient inadvertently accesses a drug container from the incorrect receptacle 222, the processor 208 detects the occurrence by way of the first sensor associated with the receptacle 222 and can display a warning message on the display screen and/or can sound an alert by way of the buzzer or the speaker.

In the case where the medication must be refrigerated, and thus not held in one of the receptacles 222, the processor 208 provides instructions on the display screen to access the drug container from the refrigerator and to scan the indicator tag of the drug container prior to administering. Scanning the indicator tag of the refrigerated drug container prior to administering allows the processor 208 to verify that the correct drug container has been accessed.

Access to the drug container from the indicated receptacle 222 can be detected by the processor 208 by way of the first sensor 225. The processor 208 records the time and date of the dosing in a database. This database may be the same as the database of the currently managed drug containers or may be a separate database. In one embodiment, the data may be stored on an external device that is on a server comprising a database.

The processor 208 may provide further instructions, such as instructing the patient to take a certain number of pills or amount of liquid medication, to take the medication with food, or refrain from eating for a period after taking the medication. The instructions can be provided via the speaker and/or the display screen.

Figure 2G:
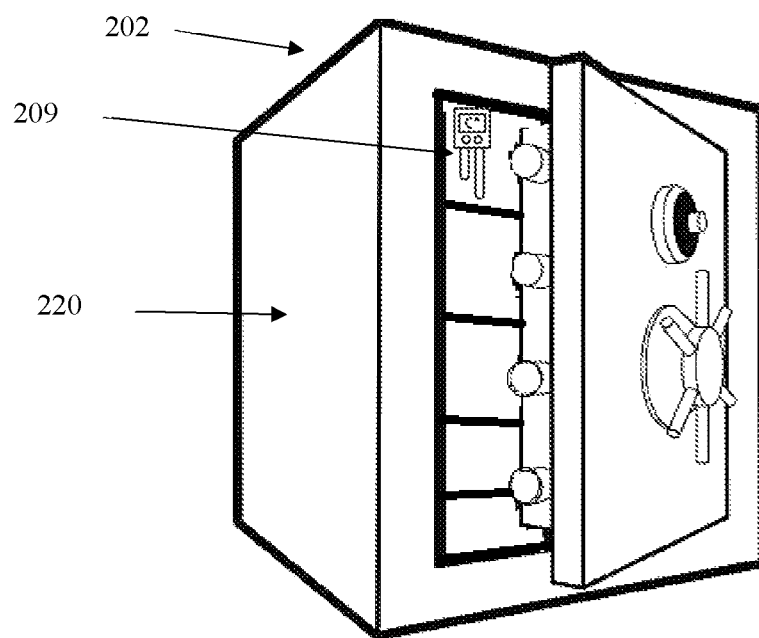
FIG. 2G shows an embodiment of the system for smart storage with a second sensor.

In an embodiment, FIG. 2G shows the drug storage comprising a second sensor 209. The system comprises a second sensor to sense physical conditioning parameters comprising at least one of a temperature, a pressure, and a humidity inside the drug storage in order to monitor a state of preservation of the drug present in the container. The second sensor 209 is fitted inside the drug storage 202 and is in communication with the processor 208 (of FIG. 2E) to send the temperature, pressure, and humidity value inside the drug storage 202 to the server.

Second sensor 209 communicates with the processor 208 to provide environmental information, physical conditioning parameters, so that the processor can display alerts on the display/output interface and the processor 208 initiates the cooling and humidity control of the system through a cooling and humidity control system. The second sensor 209 is in communication with the processor 208 which is in communication with the temperature and humidity control system and alarm. If the temperature or humidity is outside of the pre-set limits, the processor engages a cooling and humidity control system and the alarm.

Figure 3:
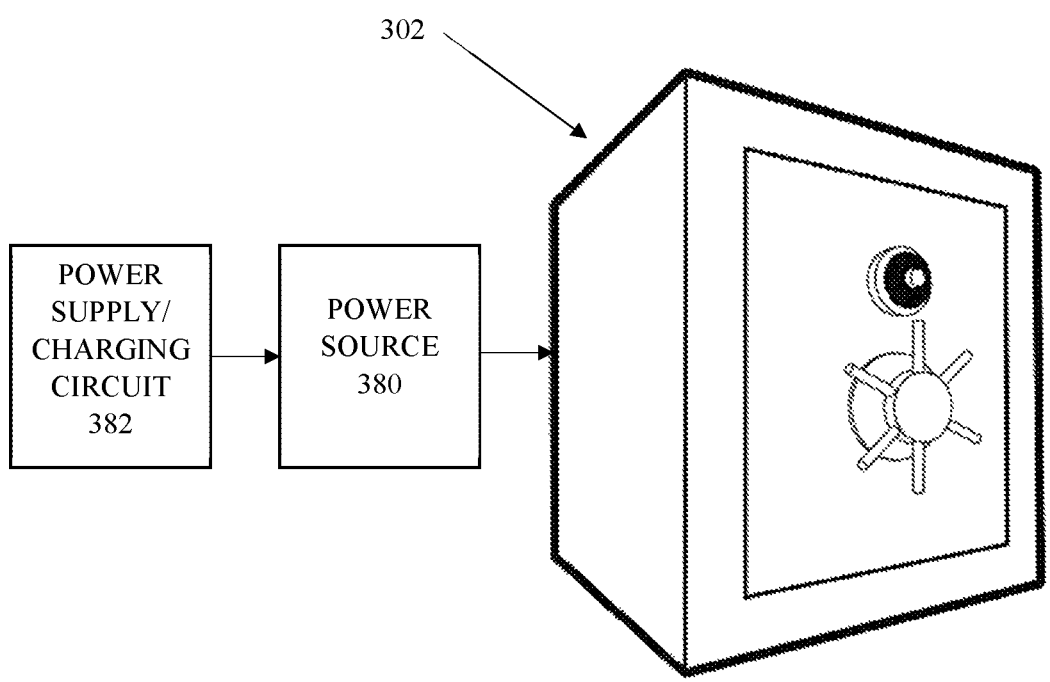
FIG. 3 shows an embodiment of the system for smart storage with a power supply.

In one embodiment, FIG. 3 shows the smart medical storage system powered by a power source 380. The power source 380 comprises an Alternating Current (AC) power source or rechargeable battery. A power supply/charging circuit 382 is coupled to the AC power source and the battery. The power supply/charging circuit 382 controls the charging of the rechargeable battery when the system for smart storage is plugged into the power source 380. Additionally, the power supply/charging circuit 382 may condition the output power from the power source 380 or rechargeable battery to provide appropriate voltages and currents to the various components of the system for smart storage 302. The system for smart storage 302 can accept 12V, 110V, 220V power input, but is not limited to this. Whenever any external power sources are available, the system for smart storage may be powered by this available external source and in addition the internal rechargeable battery, such as a Lithium-Ion battery, can charge. If external power is lost, there can be a seamless switch over to the internal battery and when external power is restored there can be a seamless switchover back to the external power and the internal battery can begin charging.

In an embodiment of the system, the record of access to the drug container comprises a hash value. The record of access is viewable on a dashboard. The record of access is accessible to a plurality of officials. The record of access is accessible to an authorized third-party official for unbiased monitoring. The record of access comprises: a name of drug, a time, a date, a day, a month, a year, a quantity of the drug accessed, name of the user receiving the drug container, and a quantity of drug container remaining. The record of access is encrypted by the system.

In an embodiment, a record of access to the drug container is stored in the database by the system through the communication module. The record of access comprises: a name of drug, a time, a date, a day, a month, a year, a quantity of the drug container accessed, name of the user receiving the drug container, and a quantity of drug containers remaining. As mentioned above, the system for smart medical storage may have one or more databases. In one embodiment, one database includes only data from current medication management, such as data obtained when scanning the drug container, name of medication, name of manufacturer of medication, image of the medication, dosage instructions, administration instructions, e.g., frequency, administration time, storage instructions, expiration date, remaining refills, interaction data, special instructions, etc., and data indicating in which receptacle the original medication container resides; and one or more additional databases comprising information regarding patient data for the user of the system, data regarding medication interactions, compliance information, etc. In one embodiment, one database comprises all of the data and information for the patient, the medications, compliance, prescribing physician/practitioner, etc. In one embodiment, the database can comprise at least a list of the drug the patient is receiving along with the frequency and dosage of that medication. Using the smart medical storage, patient compliance can be monitored to assure the patient is adhering to the proper drug frequency, and this monitoring information can be stored in the database.

In an embodiment, the log of record of the access is encrypted by the system before communicating the record of access to the database. In an embodiment, the record of access is encrypted by the system before communicating the record of access to the database.

In an embodiment, the record of access to the drug container is stored as a hash value in the database and a ledger of the record of access to the drug container is maintained using a blockchain technology by the system. In at least one embodiment, the system encrypts each of the biometric information, unique identity, prescription data and the record of access with a unique hash value (such as a random number, in at least one embodiment) to be stored in the database, thereby creating a unique link there between. In this way, only the associated user according to the biometric information, unique identity, and prescription data is capable of accessing the drug container from the drug storage, which better prevents anyone else from accessing the drug container.

In at least one such embodiment, the system utilizes blockchain to securely store the data and the record of access, so as to maintain a tamper-proof record that may be reviewed by the authorized practitioner. In at least one embodiment, if the patient attempts to access the drug container during any time other than the scheduled time, the system informs the patient that they must wait until the next scheduled time.

The ledger may be accessible to any medical professional or drug providing entity including, for example, physicians or other healthcare professionals, doctor's offices, hospitals, pharmacies, mail-order prescription companies or any other company that interfaces with the creation of a prescription or dispensation of drugs based on a prescription.

In an embodiment, the ledger may be immutable, where, for example, once an entry has been added to the shared ledger system, the entry may not be changed by any party with access to the shared ledger system. As an example, the shared ledger system may be implemented by blockchain technology.

Blockchain technology was developed as a way of providing a publicly transparent and decentralized ledger that is configured to track and store digital transactions in a publicly verifiable, secure, and hardened manner to prevent tampering or revision.

A typical blockchain includes three primary functions: read, write, and validate. For example, a user of the blockchain must have the ability to read the data that resides on the blockchain. A user of the blockchain must also have the ability to write, e.g., append data to the blockchain. Every write operation starts out as a proposed transaction that is posted on the network. The proposed transaction may not always be valid, for example, it may be malformed (syntax errors), or it may constitute an attempt to perform a task for which the submitter is not authorized. Validation refers to filtering out invalid transactions and then deciding on the exact order for the remaining, valid, transactions to be appended to the blockchain as part of a new block.

Once ordered, the transactions are packaged into a new block, and the new block is voted on by the validator nodes associated with the blockchain to determine whether to add the new block to the blockchain. If a consensus to add the new block is reached, e.g., a threshold number of "for" votes, the new block may be appended to the blockchain. Each new block that is appended to the blockchain also includes a hash of the previous block. Accordingly, as each new block is added, the security and integrity of the entire blockchain is further enhanced. It is important to note that once data is written to the blockchain, for example, once a block including a set of transactions has been appended to the blockchain, that data can no longer be altered or modified. In a typical blockchain, the anonymity of the users is protected through the use of pseudonyms and the transaction data itself is protected through the use of cryptography, e.g., via the use of hash codes.

In an embodiment, a blockchain includes a plurality of data blocks. Each data block is a data structure that includes data representing transactions, for example, a record of access to drug prescriptions, queries to the blockchain regarding a prescription, or any other transaction related to a prescription. As described above, as new transactions are submitted to the blockchain and validated by validator nodes, additional data blocks are generated by the validator nodes and appended to the blockchain. Each new data block includes a set of validated transactions and a hash of the content of the immediately previous data block. For example, data block "2" includes a hash of the content of block "1", block "n" includes a hash of the content of block "n−1", etc. Some non-limiting examples of blockchains include Bitcoin®, Ethereum®, Open Ledger™, or other similar blockchains. In an embodiment, the hashes may be generated by the validator nodes as the validator nodes generate new blocks for addition to the blockchain.

In an embodiment, blockchain is stored in a decentralized manner on a plurality of nodes, e.g., computing devices located in one or more networks. Nodes may each include a memory that stores at least a portion of a blockchain ledger. A ledger includes any data blocks that have been validated and added to the blockchain. In an embodiment, every node may store the entire ledger. In an embodiment, each node may store a portion of the ledger. In an embodiment, some, or all, of a blockchain may be stored in a centralized manner. Nodes may communicate with one another via communication modules, e.g., wired, or wireless connections, over the internet, etc., to transmit and receive data related to the ledger. For example, as new data blocks are added to the ledger, nodes may communicate or share the new data blocks via a communication module. In an embodiment, some or all of the nodes may be operated by a health configuration of a group of healthcare providers, a pharmacy, a group of pharmacies, an insurance provider, a group of insurance providers, or any other entity that may have a stake in monitoring prescription usage and the record of access to the drug container. In an embodiment, some or all of the nodes may be anonymous and unrelated to the creators or users of the prescription.

In an embodiment, any transactions submitted to the blockchain are validated by a set of validator nodes associated with blockchain. For example, transactions may be transmitted to one or more of the validator nodes and may be shared between the validator nodes for validation and consensus. Each validator node determines whether a transaction is valid and whether the transaction complies with the rules of the blockchain. The validator node adds a plurality of the validated transactions to a data block and submits the data block for consensus by all or some of the other validator nodes. The other validator nodes then vote "for" or "against" appending the data block containing the transactions to the blockchain. A consensus of the set of validator nodes, e.g., a threshold number of identical votes "for" or "against" is required to allow or deny the data block to be appended to the blockchain. In an embodiment, one or more of the nodes may be validator nodes. In an embodiment, nodes that are not validator nodes may perform processing such as, for example, receiving transaction submissions, providing member services, handling application programming interface (API) requests from users, or other similar functions. In this manner, the processing power of the validator nodes may be preserved for generating new blocks, reaching consensus, and monitoring the other validator nodes. Validator nodes may communicate with one another via the communication module, e.g., wired, or wireless connections, over the internet, etc., to transmit and receive data. For example, as new data blocks are generated by validator nodes, validator nodes may communicate or share the new data blocks and transmit and receive consensus messages via the communication module. In an embodiment, some or all validator nodes may be operated by a healthcare provider, a group of healthcare providers, a pharmacy, a group of pharmacies, an insurance provider, a group of insurance providers, or any other entity that may have a stake in monitoring prescription usage. In an embodiment, some or all validator nodes may be anonymous and unrelated to the creators or users of the prescription.

In an embodiment, the users of the ledger may be known and may provide contact information such that when new transactions or queries related to a particular prescription are received from a new user, e.g., a pharmacy, the new user may easily identify the prior users, e.g., physician or other medical personnel, and may contact the prior users when a potential case of fraud or drug abuse is detected.

In an aspect, any prescription related activities may be tracked and logged as transactions for appending to the blockchain implementing the ledger in the blockchain. For example, the creation of a new prescription by a physician or other healthcare professional, the modification of a prescription by the physician or other healthcare professional, the access to the drug container by the user, queries to the ledger about a prescription by a physician, other healthcare professional, pharmacy, or other entity, or other similar transactions or activities related to a prescription may be appended to the ledger.

In an embodiment, the validation code may be generated by a shared ledger system at a time when the prescription data is submitted by the prescription details in the database, e.g., via network interfaces, as a transaction for addition to the blockchain. For example, one or more nodes or validator nodes may generate the validation code when the prescription data is received from a prescription entry device, and may add the validation code to the prescription data prior to appending the prescription data to a block for addition to the blockchain.

Once prescription data for a prescription has been submitted to a shared ledger system and a validation code has been generated and added to the prescription data, prescription data may be added to a new block by a validator node of the shared ledger system. The validators may then reach a consensus and add the new block containing the prescription data to the blockchain. In an embodiment, only prescriptions received from verified prescribers, e.g., those using prescription entry devices, may be validated for addition to the blockchain. For example, if a prescription is received from a non-verified device, the shared ledger system may deny entry of the prescription to the blockchain. In an embodiment, all or part of the prescription data may be encrypted, by a prescription entry device or by a shared ledger system to protect patient privacy, when submitted for addition to the blockchain. In an embodiment, an image of the prescription may be stored separately from the blockchain, for example, in a separate database, and the prescription data stored on the blockchain may include a link, e.g., a Uniform Resource Locator (URL) link, pointing to the prescription image.

In an embodiment, prescription data may be checked against other prescriptions already added to the blockchain. For example, the validator node may determine whether there is already an active prescription for the listed patient for the same medication. If such a prescription exists, the shared ledger system may notify the prescribing physician, e.g., via prescription entry device, and indicate that the prescribing physician should manually verify the existence of the prior active prescription. For example, the prior active prescription that is already appended to the blockchain may include identification or contact information for a prescribing physician that may be used to verify whether the patient has already received a prescription for the same medication from another physician. This verification may be used to prevent doctor shopping where, for example, a patient may receive separate prescriptions for the same medication from more than one physician.

In an embodiment, the record of access is viewable on a dashboard. The record of access is accessible to a plurality of officials. The record of access is accessible to an authorized third-party official for unbiased monitoring.

In an embodiment, the system is a Drug Enforcement Administration compliant system. The DEA was established in 1973 as the federal organization in charge of enforcing the controlled substances laws of the United States. The mission of the Drug Enforcement Administration (DEA) is to enforce the controlled substances laws and regulations of the United States and bring to the criminal and civil justice system of the United States, or any other competent jurisdiction, those organizations and principal members of organizations, involved in the growing, manufacture, or distribution of controlled substances appearing in or destined for illicit traffic in the United States; and to recommend and support non-enforcement programs aimed at reducing the availability of illicit controlled substances on the domestic and international markets. The relevant Drug Enforcement Administration requirements for controlled substances storage are found in 21 CFR 1301.72 of the Food and Drug Administration. In summary form, they mandate: Where small quantities permit, a safe or steel cabinet. Walls of the vault and ceilings of reinforced concrete or "substantial" masonry. Vault doors and frames provide 30 "man minutes" against surreptitious entry, up to 20 "man hours" against lock manipulation. Vault doors are outfitted with day gates that are self-closing and self-locking. Alarms, and monitoring devices such as sound accumulators or ultrasonics. Cages with walls of not less than No. 10 gauge steel fabric, mounted on steel posts set in concrete or installed with pinned or brazed lab bolts; with mesh openings not more than 2.5 in. Cage ceilings with similar contraction (lighter gauge steel mesh in some situations), or cages that are secured to the ceiling of the drug storage facility. Self-closing and self-locking doors for cages; alternatively, for occasional access to the cage, a 24-hour/day monitoring service.

An embodiment relates to a method comprising steps of receiving an identification of a user through a system; authenticating the user through the system; deactivating a lock of a container of a drug storage; and allowing the user to access a drug container; communicating through a communication module; logging a record of access to the drug container; and maintaining a ledger of the record of access to the drug container using blockchain technology. The system is secured through a cyber security module.

In an embodiment of the method, the identification of the user comprises a unique identity and a biometric identification of the user.

In an embodiment of the method, authenticating the user and logging the record of access to the drug container comprises communicating with a server through the system; and wherein the server comprises a database. The authentication of the user comprises a second level of authentication. The second level of authentication comprises the unique identity of the user and the biometric identification of the user.

In an embodiment of the method, authentication of the user further comprises receiving the unique identity of the user comprising at least one of a unique identification number, an RFID tag, a password, and an unlocking pattern. The authentication of the user further comprises receiving a biometric identification of the user comprising at least one of fingerprint, eyeblink, retina scan, iris scan, facial image scan and eye scan.

The authentication comprises matching credentials of the unique identity with a record of practitioners and a record of patients stored in the database. The method further comprises locking the drug storage for the access if the credentials of the unique identity do not match with the record of practitioners and the record of patients in the database.

In an embodiment of the method, authenticating comprises matching credentials of the biometric identification with a record of practitioners and a record of patients stored in the database. The method further comprises locking the drug storage for the access if the credentials of the biometric identification do not match with the record of practitioners and the record of patients in the database.

In an embodiment of the method, the method further comprises locking the drug storage for the user that exceeds a predefined count of the access to the drug container in a day. The method further comprises synchronizing the access to the drug container in the drug storage with a scheduled time of use of the drug container by the user. The method further comprises unlocking the access to the drug container in the drug storage by an authorized owner of the system.

In an embodiment of the method, the method further comprises sensing of physical conditioning parameters by the system comprising at least one of a temperature, a pressure, a humidity inside the drug storage in order to monitor a state of preservation of the drug present in the container.

In an embodiment of the method, the method further comprises monitoring the access to the drug container through a camera.

In an embodiment of the method, the method further comprises sending a change in a weight value to the server in case of the access to the drug container. The method further comprises comparing the change in the weight value with the weight value of the drug container from prescription details in the database to determine if the access to the drug container is secure. The method further comprises updating the change in the weight value in the prescription details in the database after the access to the drug container.

In an embodiment of the method, the method further comprises detecting a change in data received by an RFID tag reader in the system from an RFID tag on the drug container; and reporting a count of drug containers accessed to the server by the system in cases of change in the data received.

In an embodiment of the method, the method further comprises scanning an indicator tag comprising at least one of a Universal Product Code (UPC) indicia, a Quick Response (QR) code, a High-Capacity Color Barcode (HCCB), and a Near-Field Communication (NFC) tag. The indicator tag is utilized to identify the drug container. The indicator tag comprises a detail of the drug comprising an inventory count of the drug container, a name of the drug, expiry date and a disease it is used to treat.

In an embodiment of the method, the method further comprises sending the record of access to the drug container to the server on each of the access to the drug container from the drug storage in order to track the access to the drug container.

In an embodiment of the method, the drug comprises a controlled substance, opioids, a narcotic, and a psychedelic drug.

In an embodiment of the method, the method further comprises viewing the record of access on a dashboard. The record of access is accessible to a plurality of officials. The record of access is accessible to an authorized third-party official for unbiased monitoring. The record of access comprises: a name of drug, a time, a date, a day, a month, a year, quantity of the drug container accessed, name of the user receiving the drug container, and a quantity of drug containers remaining. The record of access is encrypted by the system.

In an embodiment of the method, the method further comprises providing an isolation between the system and the server by an information security management module for cyber security.

In an embodiment of the method, the method comprises receiving data from at least one of an input interface, the drug storage, the server, and the database; exchanging a security key at a start of a communication between the communication module and the server; receiving the security key from the server; authenticating an identity of the server by verifying the security key; analyzing the security key for potential cyber security threats; negotiating an encryption key between the communication module and the server; encrypting the data; and transmitting the encrypted data to the server in case no cyber security threat is detected. The method comprises raising an alarm if the cyber security threat is detected.

In an embodiment of the method, the method comprises exchanging a security key at a start of the communication between the communication module and the server receiving the security key from the server; authenticating an identity of the server by verifying the security key; analyzing the security key for potential cyber security threats; negotiating an encryption key between the system and the server; receiving encrypted data; decrypting the encrypted data; performing an integrity check of the decrypted data; and transmitting the decrypted data to at least one of an output interface, the drug storage, and the database through the communication module in case no cyber security threat is detected. The method comprises raising an alarm if the cyber security threat is detected. The method comprises discarding the encrypted data received if the integrity check of the encrypted data fails.

In an embodiment of the method, the method comprises checking the integrity of the encrypted data by checking accuracy, consistency, and any possible data loss during the communication through the communication module.

In an embodiment of the method, the method comprises performing asynchronous authentication and validation of the communication between the communication module and the server.

In an embodiment of the method, the cyber security module further comprises an information security management module providing isolation between the system and the server.

Figure 4:
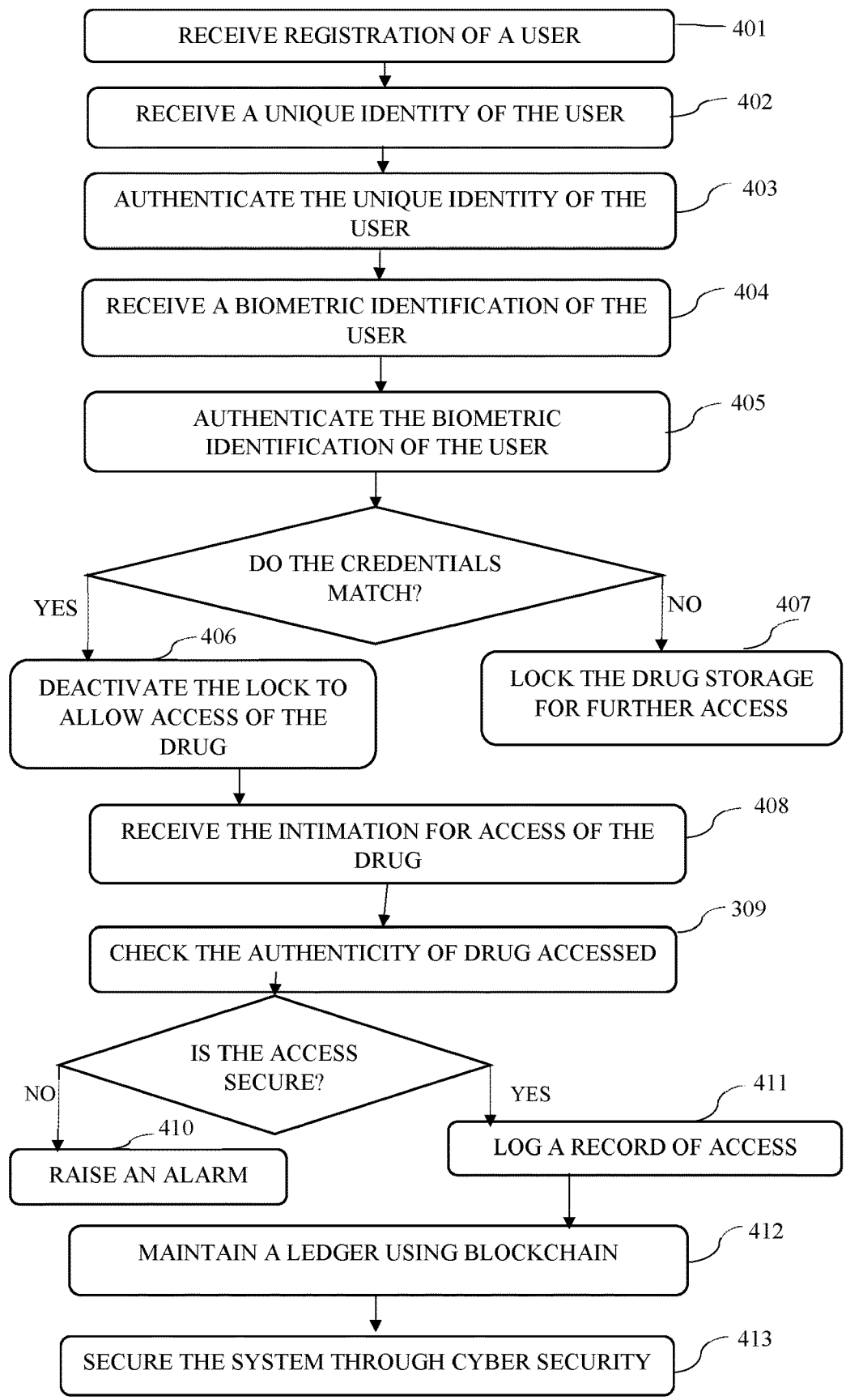
FIG. 4 shows a method to access the drug by using the system for smart storage.

FIG. 4 illustrates a method for secured access to the drug container from the smart storage.

At step 401, the user is registered into the system in order to authorize the user to access the drug container from the drug storage. The biometric identification and the unique identity of the user is pre-stored in the database for the matching of credentials. The biometric identification and the unique identity are stored in the database when the user registers himself for the first time in the system. The system may ask for registration for a first-time user, the registration of the patient comprises name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The registration of a practitioner comprises name of practitioner, age of practitioner, gender of the practitioner, qualification of the practitioner, experience in years, biometric information, unique identity information, name of patient under the practitioner's supervision. The authorized owner of the system may only do the registration of the user.

At step 402, the system is configured to receive an identification of the user when a user needs to access the drug container. The unique identity of the user comprises a unique identification number, an RFID tag, a password, and an unlocking pattern.

At step 403, the system interacts with the server to authenticate the user by matching credentials of the unique identity against a record of practitioners and a record of patients stored in the database. The record of patient comprises a name of patient, age of the patient, gender of the patient, a disease, a type of treatment going on, symptoms of the disease, other diseases, allergies, biometric information, unique identity information, physiological information, biological marker of patient, drug prescription, scheduled timings to take the drug. The record of practitioner comprises name of practitioner, age of practitioner, gender of the practitioner, qualification of the practitioner, experience in years, biometric information, unique identity information, name of patient under the practitioner's supervision.

At step 404, the system receives biometric identification of the user. The biometric identification received comprises a fingerprint, a facial recognition (i.e., a camera with corresponding facial recognition software), an iris scan, and a retinal scan. In still further embodiments, the biometric identification may be any other type of biometric sensor now known or later developed.

At step 405, the system interacts with the server to authenticate the user by matching credentials of the biometric identification against a record of practitioners and a record of patients stored in the database. The biometric identification and the unique identity of the user is pre-stored in the database for the matching of credentials. The biometric identification and the unique identity are stored in the database when the user registers himself for the first time in the system.

At step 406, the lock of the drug storage is deactivated if the credentials of the biometric identification and unique identity matches with the database. The user is allowed to access the drug container from the drug storage.

At step 407, in case any one of the credentials of the biometric identification and the unique identity do not match with the record of practitioners and the record of patients in the database, the drug storage is locked for further access. The user has a predefined number of accesses to the drug container in a day. If the number of accesses exceeds in a day and if a request to access the drug container is received other than a scheduled time, then the drug storage is locked for further access.

At step 408, the system receives an intimation of the access to the drug container from the drug storage from the receptacle of the drug storage.

At step 409, the system checks if the drug container accessed is the correct drug container and if the quantity of the drug containers accessed is the prescribed quantity of the drug containers. The system checks the quantity of drug containers, the scheduled time of delivering the drug containers, and the prescription quantity of the drug containers by interacting with the database on the server.

At step 410, raise an alarm if any of the quantity or the scheduled time to access the drug container do not match with the database.

In an embodiment of the method, the physical conditioning parameters comprising temperature, pressure, and humidity inside the drug storage are checked in order to monitor a state of preservation of the drug present in the container.

At step 411, a record of access to the drug container is stored in the database by the system through the communication module. The record of access comprises: a name of drug, a time, a date, a day, a month, a year, a quantity of the drug container accessed, name of the user receiving the drug container, and a quantity of drug container remaining.

At step 412, a record of access to the drug container is stored as a hash value in the database and a ledger of the record of access to the drug container is maintained using a blockchain technology.

At step 413, a record of access to the drug container is secured by cyber security. The data to be communicated between the system and the server is analyzed for potential cyber security threats. The data is encrypted in cases when no cyber security threat is detected. The encrypted data is transmitted to the server or to the system. The data received is checked for a cyber security threat. The data is decrypted in case no cyber security threat is detected; else the data is discarded.

Cyber Security Module

According to an embodiment, it is a system comprising a device; a communication module communicating with a server; a user interface; a bio-feedback monitoring device; a drug dispenser; a database; and a cyber security module.

In an embodiment, the cyber security module further comprises an information security management module providing isolation between the system and the server.

In an embodiment, the information security management module is operable to, receive data from at least one of the user interface, the bio-feedback monitoring device, the drug dispenser, and the database, exchange a security key at a start of the communication between the communication module and the server, receive the security key from the server, authenticate an identity of the server by verifying the security key, analyze the security key for a potential cyber security threat, negotiate an encryption key between the communication module and the server, encrypt the data; and transmit the encrypted data to the server when no cyber security threat is detected.

In an embodiment, the information security management module is operable to exchange a security key at a start of the communication between the communication module and the server, receive the security key from the server, authenticate an identity of the server by verifying the security key, analyze the security key for a potential cyber security threat, negotiate an encryption key between the system and the server, receive encrypted data from the server, decrypt the encrypted data, perform an integrity check of the decrypted data and transmit the decrypted data to at least one of the user interface, the bio-feedback monitoring device, the drug dispenser, and the database through the communication module when no cyber security threat is detected.

In an embodiment, the information security management module is configured to raise an alarm when the cyber security threat is detected.

In an embodiment, the information security management module is configured to raise an alarm when a cyber security threat is detected.

In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the information security management module is configured to perform asynchronous authentication and validation of the communication between the communication module and the server.

In an embodiment, a perimeter network provides an extra layer of protection.

In an embodiment, the perimeter network protects the system from a cyber security threat by using a plurality of firewalls.

In an embodiment, the system may comprise a cyber security module, a communication module, a server, and a database.

In one aspect, the cyber security module comprises a secure communication management (SCM) computer device for providing secure data connections in the healthcare environment is provided. The SCM computer device includes a processor in communication with memory. The processor is programmed to receive from an input interface. The first data message is in a standardized data format. The processor is also programmed to analyze the first data message for potential cyber security threats. If the determination is that the first data message does not contain a cyber security threat, the processor is further programmed to convert the first data message into a first data format associated with the healthcare environment and transmit the converted first data message through the communication module to the healthcare system using a first communication protocol associated with the healthcare system.

According to an embodiment, secure authentication for data transmissions comprises, provisioning a hardware-based security engine (HSE) located in communications system, said HSE having been manufactured in a secure environment and certified in said secure environment as part of an approved network; performing asynchronous authentication, validation and encryption of data using said HSE, storing user permissions data and connection status data in an access control list used to define allowable data communications paths of said approved network, enabling communications of the communications system with other computing system subjects to said access control list, performing asynchronous validation and encryption of data using a security engine including identifying a user device (UD) that incorporates credentials embodied in hardware using a hardware-based module provisioned with one or more security aspects for securing the system, wherein security aspects comprising said hardware-based module communicate with a user of said user device and said HSE.

In an embodiment, there is a cyber security module embedded in each of the layers namely Human Layer, Perimeter Layer, Network Layer, Endpoint Layer, Application Layer, Data Layer, and Mission Critical Layer. Each layer represents a different stage in network communication, from a human typing on a keyboard to the data system used for applications.

Figure 5A:
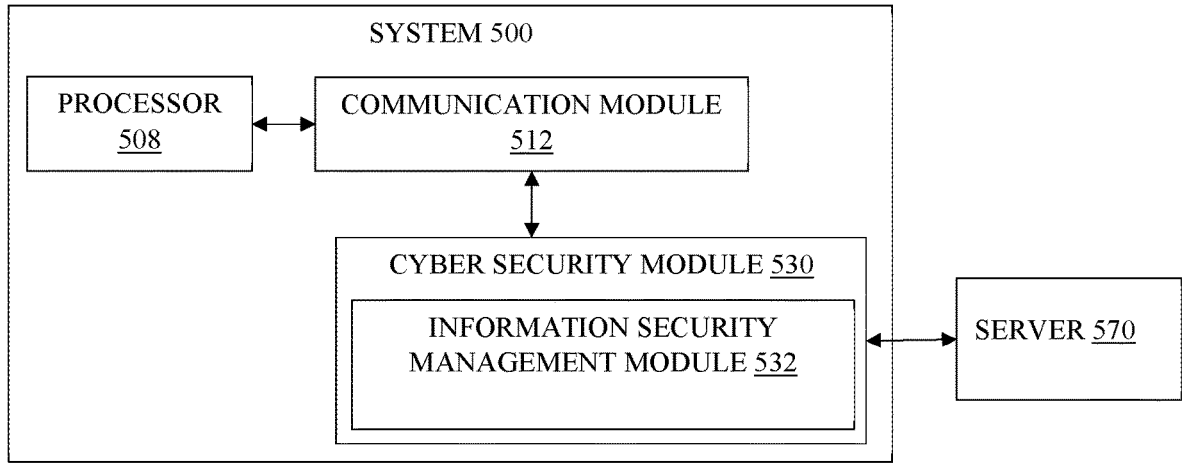
FIG. 5A shows a block diagram of the cyber security module in view of the system and server.

In an embodiment, FIG. 5A shows the block diagram of the cyber security module. The communication of data between the system 500 and the server 570 through the communication module 512 is first verified by the information security management module 532 before being transmitted from the system to the server or from the server to the system. The information security management module is operable to analyze the data for potential cyber security threats, encrypt the data when no cyber security threat is detected, and transmit the data encrypted to the system or the server.

Figure 5B:
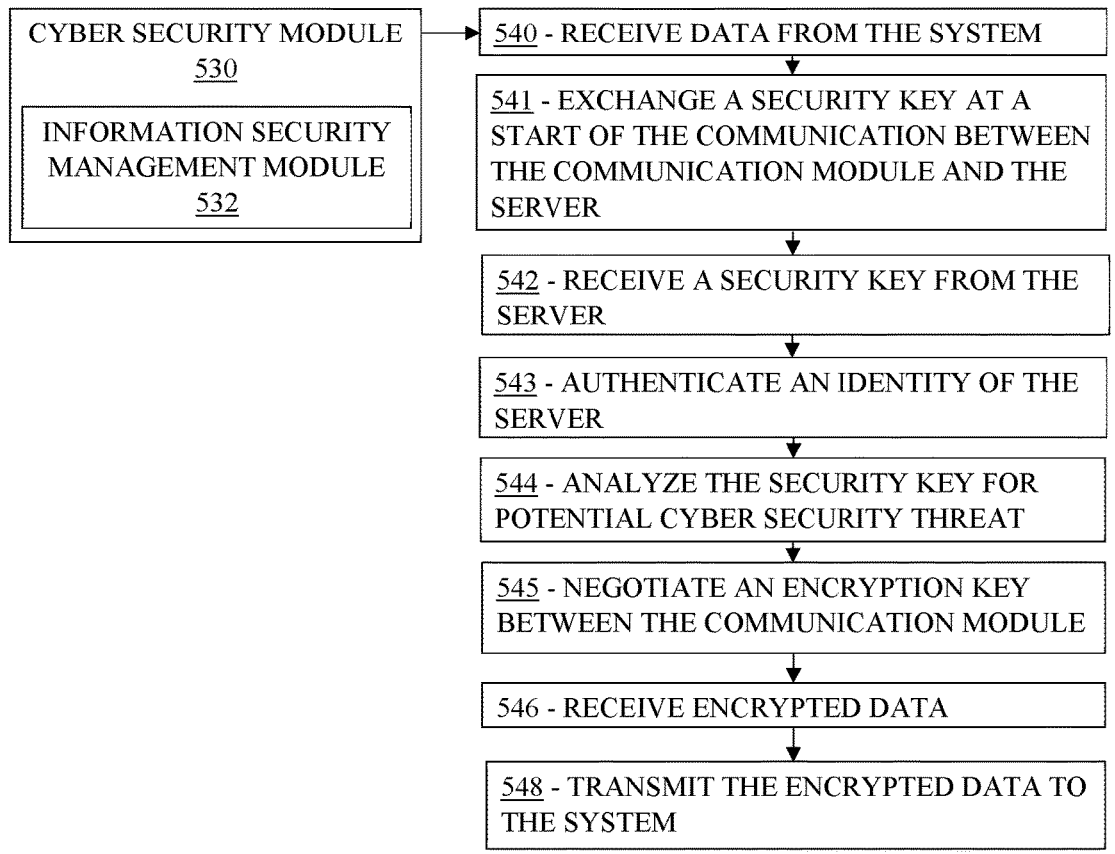
FIG. 5B shows an embodiment of the cyber security module.

In an embodiment, the cyber security module further comprises an information security management module providing isolation between the system and the server. FIG. 5B shows the flowchart of securing the data through the cyber security module 530. At step 540, the information security management module is operable to receive data from the system, for example, at least one of an input interface, the drug storage, and the database. At step 541, the information security management module exchanges a security key at a start of the communication between the communication module and the server. At step 542, the information security management module receives a security key from the server. At step 543, the information security management module authenticates an identity of the server by verifying the security key. At step 544, the information security management module analyzes the security key for potential cyber security threats. At step 545, the information security management module negotiates an encryption key between the communication module and the server. At step 546, the information security management module encrypts the data. At step 547, the information security management module transmits the encrypted data to the server when no cyber security threat is detected.

Figure 5C:
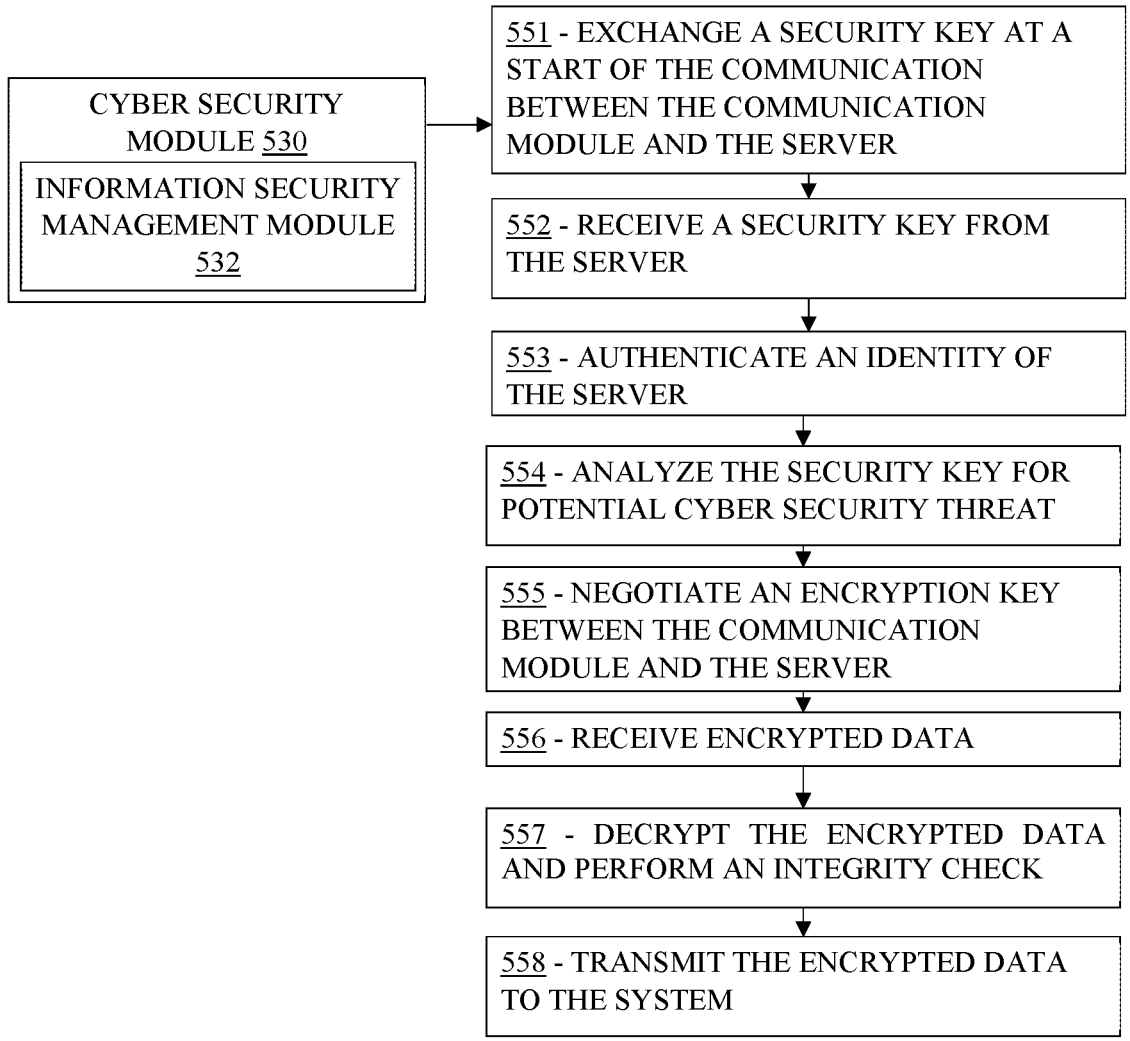
FIG. 5C shows another embodiment of the cyber security module.

In an embodiment, FIG. 5C shows the flowchart of securing the data through the cyber security module 530. At step 551, the information security management module is operable to: exchange a security key at a start of the communication between the communication module and the server. At step 552, the information security management module receives a security key from the server. At step 553, the information security management module authenticates an identity of the server by verifying the security key. At step 554, the information security management module analyzes the security key for potential cyber security threats. At step 555, the information security management module negotiates an encryption key between the system and the server. At step 556, the information security management module receives encrypted data. At step 557, the information security management module decrypts the encrypted data, performs an integrity check of the decrypted data. At step 558, the information security management module transmits the decrypted data to the system through the communication module when no cyber security threat is detected.

In an embodiment, the integrity check is a hash-signature verification using a Secure Hash Algorithm 256 (SHA256) or a similar method. A cryptographic hash (sometimes called 'digest') is a kind of 'signature' for a text or a data file. SHA256 generates an almost-unique 256-bit (32-byte) signature for a text.

In an embodiment, the information security management module is configured to perform asynchronous authentication and validation of the communication between the communication module and the server.

In an embodiment, a perimeter network provides an extra layer of protection. In an embodiment, the perimeter network protects the system from a cyber security threat by using a plurality of firewalls. Usually, a perimeter network is the final step a packet takes traversing one of the system's networks on its way to the internet; and conversely the first network encountered by incoming traffic from the Internet to the system.

In an embodiment, a demilitarized zone (DMZ) network functions as a subnetwork containing an organization's exposed, outward-facing services. It acts as the exposed point to an untrusted network, commonly the Internet. A DMZ network will add an extra layer of security to an organization's local area network. It is a protected and monitored network node that faces outside the internal network and can access what is exposed in the DMZ, while the rest of the organization's network is safe behind a firewall. A DMZ Network gives organizations extra protection in detecting and mitigating security breaches before they reach the internal network, where valuable assets are stored. All services accessible to users communicating from an external network can and should be placed in the DMZ, if one is used. The most common services include, but are not limited to, web servers, mail servers, file transfer protocol (FTP) servers.

In an embodiment, the information security management module is configured to raise an alarm if a cyber security threat is detected. In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the server is physically isolated from the system through the information security management module. When the system communicates with the server as shown in FIG. 5A, identity authentication is first carried out on the system and the server. The system is responsible for communicating/exchanging a public key of the system and a signature of the public key with the server. The public key of the system and the signature of the public key are sent to the information security management module. The information security management module decrypts the signature and verifies whether the decrypted public key is consistent with the received original public key or not. If the decrypted public key is verified, the identity authentication is passed. Similarly, the system and the server carry out identity authentication on the information security management module. After the identity authentication is passed on to the information security management module, the two communication parties, the system, and the server, negotiate an encryption key and an integrity check key for data communication of the two communication parties through the authenticated asymmetric key. A session ID number is transmitted in the identity authentication process, so that the key are bound with the session ID number; when the system sends data to the outside, the information security gateway receives the data through the communication module, performs integrity authentication on the data, then encrypts the data through a negotiated secret key, and finally transmits the data to the server through the communication module. When the information security management module receives data through the communication module, the data is decrypted first, integrity verification is carried out on the data after decryption, and if verification is passed, the data is sent out through the communication module; otherwise, the data is discarded.

In an embodiment, the identity authentication is realized by adapting an asymmetric key with a signature.

In an embodiment, the signature is realized by a pair of asymmetric keys which are trusted by the information security management module and the system, wherein the private key is used for signing the identities of the two communication parties, and the public key is used for verifying that the identities of the two communication parties are signed.

In an embodiment, the identity authentication is that both communication parties need to authenticate their own identities through a pair of asymmetric keys, and a task in charge of communication with the information security management module of the system is identified by a unique pair of asymmetric keys.

In an embodiment, the dynamic negotiation key is encrypted by adopting an Rivest-Shamir-Adleman (RSA) encryption algorithm. RSA is a public-key cryptosystem that is widely used for secure data transmission. The negotiated keys include a data encryption key and a data integrity check key.

In an embodiment, the data encryption method is a Triple Data Encryption Algorithm (3DES) encryption algorithm. The integrity check algorithm is a Hash-based Message Authentication Code (HMAC-MD5-128) algorithm. When data is output, integrity check calculation is carried out on the data, the calculated Message Authentication Code (MAC) value is added with the head of the value data message, then the data (including the MAC of the head) is encrypted by using a 3DES algorithm, the head information of a security layer is added after the data is encrypted, and then the data is sent to the next layer for processing.

In an embodiment the next layer refers to a transport layer in the Transmission Control Protocol/Internet Protocol (TCP/IP) model.

In an embodiment, when the receiving side finds an authentication error or a MAC decryption error, it is necessary to send a fatal error message to the transmitting side and close the connection.

The information security management module ensures the safety, reliability, and confidentiality of the communication between the system and the server through the identity authentication when the communication between the two communication parties starts the data encryption and the data integrity authentication in the communication process. The method is particularly suitable for an embedded platform which has less resources and is not connected with a Public Key Infrastructure (PKI) system and can ensure that the safety of the data on the server of the drug storage cannot be compromised by hacker attacks under the condition of the Internet by ensuring the safety and reliability of the communication between the system and the server in the system for smart storage.

In an embodiment, a system hardening strategy is implemented to prevent at least one attack. An attack graph analysis may be used to help analyze network vulnerability. Once an attack graph of conditions and/or exploits (e.g., at least one goal condition, at least one initial condition, at least one exploit) is obtained, allowable actions that may harden the conditions may be obtained. Costs associated with the allowable actions may also be obtained. Recommended actions to harden the network with respect to one or more goal conditions may be determined.

Figure 6:
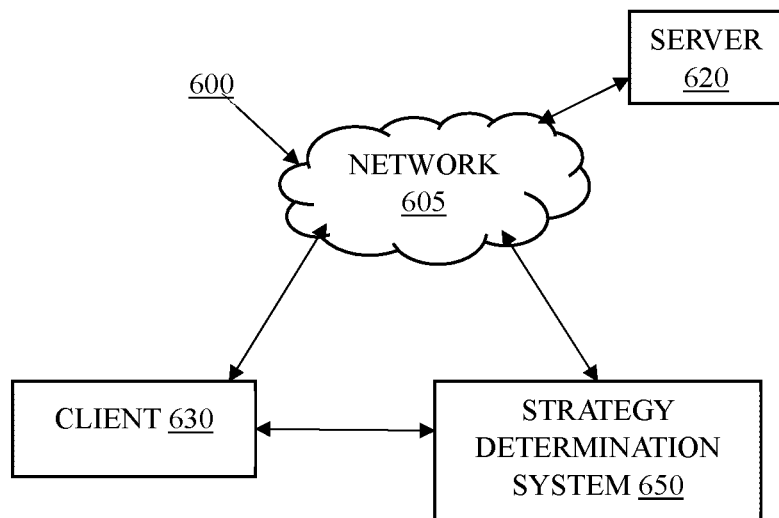
FIG. 6 is an example system where a system hardening strategy may be implemented according to an embodiment of the invention.

FIG. 6 is a system 600 according to an embodiment of the invention. In this example, the system 600 may comprise a network 605 (e.g., the Internet, an intranet) wherein one or more computers 620 (e.g., server, client) may communicate with one another. A strategy determination system 650 may communicate with the client and/or the server. The strategy determination system 650 may obtain an attack graph of conditions and/or exploits (e.g., using known techniques), obtain allowable actions that may remove one or more initial conditions to harden the network with respect to one or more goal conditions; obtain costs associated with the allowable actions, and determine recommended system hardening strategies to efficiently harden the network with respect to the goal condition(s), each system hardening strategy consisting of one or multiple allowable actions. As attackers may leverage complex interdependencies of network configurations and vulnerabilities to penetrate seemingly well-guarded networks, in an embodiment, the recommended actions may consider attacker exploits in isolation and/or in combination. Attack graphs may reveal such threats by enumerating potential paths that attackers can take to penetrate networks. This may help determine whether a given set of system hardening measures provides safety for given critical resources.

System hardening goal conditions may have a corresponding impact on removing paths in the attack graph. In addition, system hardening solutions that are optimal with respect to some notion of cost and/or time may be determined. Such system hardening solutions prevent the attack from succeeding, while minimizing the associated costs.

The strategy determination system 650 may comprise: a determine allowable actions module; an associate costs module; a determine recommended actions module; or an approximation module; or any combination thereof. In the strategy determination method, an attack graph comprising conditions and/or exploits may be obtained, allowable actions that remove one or more initial conditions may be obtained, costs associated with the allowable actions may be obtained, and recommended strategies comprising allowable actions may be determined based upon costs and/or time constraints.

Spyware is a type of malware that may be installed on computers and collects bits of information at a time about users without their knowledge. The presence of spyware is typically hidden from the user and may be difficult to detect. Spyware programs may collect various types of personal information, such as Internet surfing habits and sites that have been visited but may also interfere with user control of the computer in other ways, such as installing additional software and redirecting Web browser activity.

Figure 7:
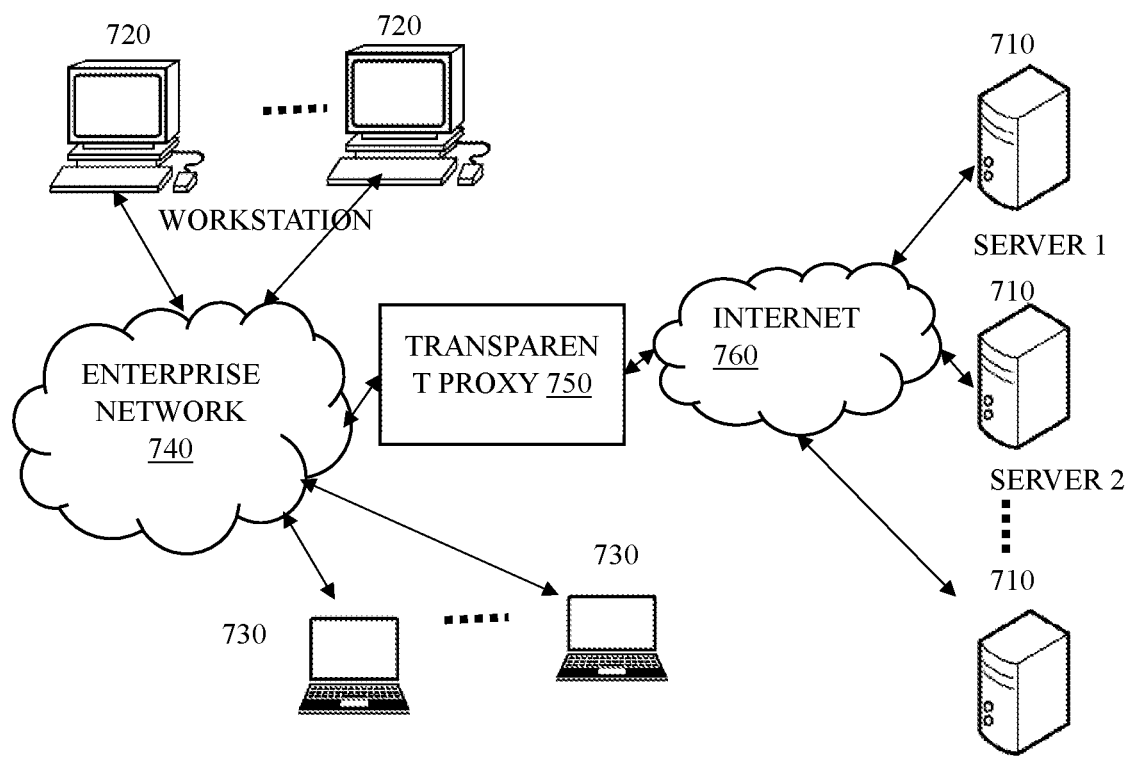
FIG. 7 shows an architecture of a network using a transparent proxy in an Enterprise network as per an aspect of an embodiment of the present invention for active malware detection.

Passive detection may identify a fraction of the malware that is collected in an enterprise network but may not identify all of them. Embodiments of the present invention utilize active detection mechanism(s). The active detection mechanism(s) may also be called Active Content Challenges and may be implemented using a transparent proxy. FIG. 7 shows the architecture of a network using an embodiment of the transparent proxy 750 in an Enterprise network 740 including workstations 720 and laptops 730. The architecture may be fully transparent and may not require any application or network modifications both for client applications and servers and may accommodate various protocols including HTTP, encrypted HTTP (HTTPS) and Voice over IP (VOIP) protocols. The transparent proxy 750 may mediate all traffic both encrypted and unencrypted when an application initiates a communication with a server 710 connected to Internet 760 outside the enterprise. Communication may pass through the firewall while being examined and analyzed by the transparent proxy 750. According to an embodiment, a transparent proxy may be in a laptop or workstation. The transparent proxy may mediate all traffic both encrypted and unencrypted when an application initiates a communication with a remote server connected to the internet.

The transparent proxy 750 may intercept outbound requests and issue Active Content Challenges to the requesting application. The principle is similar to Turing puzzles and Captchas, however, rather than trying to distinguish a human from software, the objective is to distinguish legitimate software from malware. Thus, unlike existing mechanisms that demand end-users to be involved in the identification process by solving a puzzle, the approach in this embodiment requires no user involvement or application modification. The transparent proxy for malware detection may include a monitor module, a protocol determination module, a challenge generation module, a response determination module, and a data control module. The transparent proxy may include interfaces for receiving and transmitting applications traffic and remote server traffic. The transparent proxy may be located on a network edge or on a laptop or workstation and may examine outgoing traffic. In general, the approach frustrates the communication of the malware by injecting traffic that the malware is incapable of parsing and generating a valid response contrary to the legitimate application.

In an embodiment, a secure virtual browsing environment is provided which includes creating a virtual browsing environment with a virtualized operating system sharing an operating system kernel of a supporting operating system and executing the browser application within the virtual browsing environment. Another embodiment includes receiving a website selection within a browser application, determining if the website selection corresponds to a secure bookmark, and creating a second virtual browsing environment and executing the browser application within the second virtual browsing environment to access the website selection when the website selection corresponds to a website specified as a secure bookmark. Another embodiment includes monitoring operation of the operating system within the at least one virtual browsing environment, determining when the operation of the operating system includes potential malicious activity, and terminating the virtual browsing environment when the operation includes potential malicious activity.

Figure 8A:
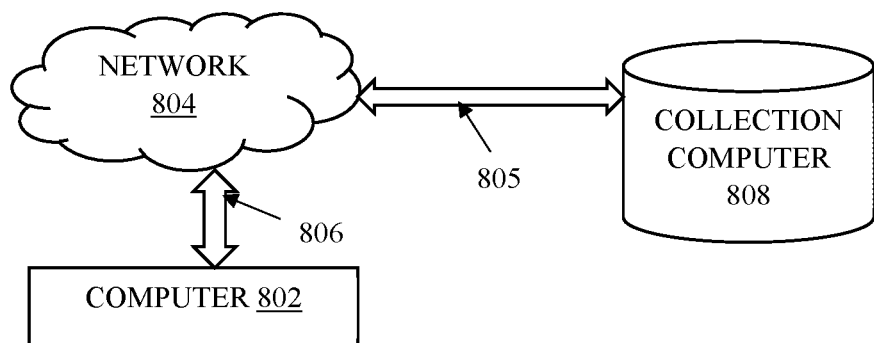
FIG. 8A illustrates a system for providing a virtual browsing environment according to an aspect of an embodiment of the invention.

FIG. 8A illustrates a system 800 for providing a virtual browsing environment according to one embodiment of the invention. As described below, embodiments of the system 800 may provide a virtual browsing environment for executing a browser application on a computer. By executing the browser application within a separate virtual browsing environment, other applications, data, and modules of the computer may be protected from any malicious activity associated with the execution of the browser application. In addition, because in some embodiments only the browser application may be executed within the virtual browsing environment, malicious activity associated with the execution of the browser application may be easily detected. The system 800 may include at least one computer 802, at least one network 804, and at least one collection computer ("CC") 808 and other components. The computer 802 and the network 804 may be connected by a connection 806, and the network 804 and the collection computer 808 may be connected by a connection 805. The collection computer 808 may receive data from the network 804 over the connection 805. In some embodiments, the collection computer 808 may also send data to the network 804 or one or more computers or networks. The collection computer 808 may also include hardware, such as one or more memory modules, one or more processors, and one or more input/output modules. In addition, the collection computer 808 may include an operating system to manage the hardware. In some embodiments, the collection computer 808 may also include a database that stores data received from the network 804. The data included in the database may be stored in the collection computer's 808 one or more memory modules, and the data may be managed by a database management application.

Figure 8B:
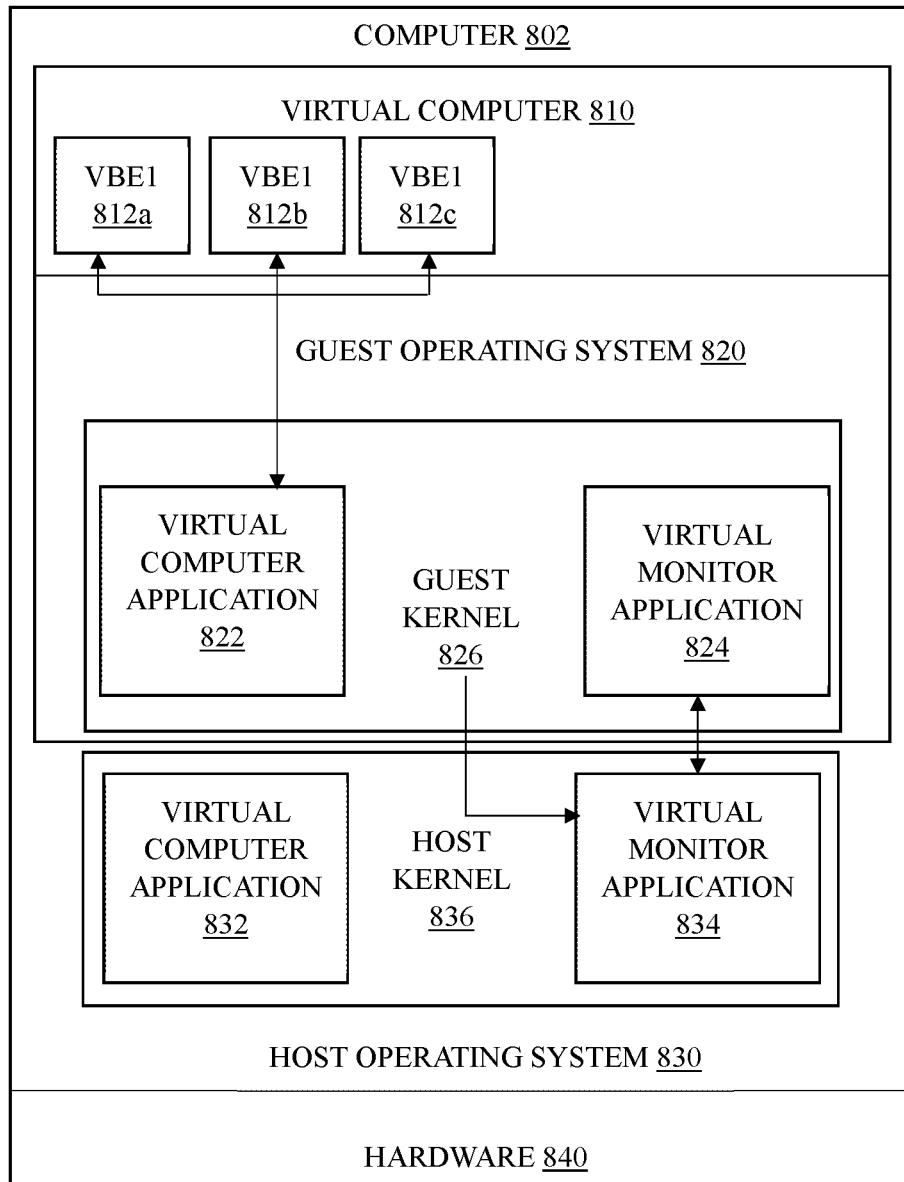
FIG. 8B illustrates a computer included in the system of FIG. 13A, according to an embodiment of the invention.

FIG. 8B illustrates the computer 802 of FIG. 8A which includes a host operating system 830 that provides an interface between the hardware 840 and a user operating the computer 802. The host operating system 830 may be stored in the one or more memory modules and may be executed on the one or more processors included in the hardware 840. The host operating system 830 may include at least one host kernel 836. The host kernel 836 may manage the communication between the hardware 840 and applications executed by the hardware 840. The host kernel 836 may use the virtual control application (VCA) 834 to create and manage a virtual computer. Accordingly, the VCA 834 may provide virtualization functionality. The host kernel 836 may also include a shared preference directory 832, which may store preferences for an application, such as a browser application. It should be understood that the one or more memory modules included in the hardware 840 may store other applications besides those explicitly shown in FIG. 8B. In addition, the functionality provided by the applications stored in the one or more memory modules may be combined and distributed in various configurations.

In operation, as shown in FIG. 8B, the host kernel 836 may execute the VCA 834 to create a virtual computer 810. The virtual computer 810 may include its own guest host operating system 820 with a guest kernel 826. The guest operating system 820 and guest kernel 826 may operate similar to the host operating system 830 and host kernel 836. This type of virtualization, where a generally complete copy of an operating system is provided within a virtual computer is generally referred to as "full virtualization." Outside of the virtual computer 810, the host operating system 830 may continue to interact and manage the hardware 840, while the guest operating system 820 also may interact and manage the hardware 840. Therefore, the virtual computer 810 may create a second, isolated computing environment within the computer 802. Each computing environment may execute different applications, access data from different locations in a memory module or from different memory modules, provide different operating systems, or combinations thereof. Creating the virtual computer 810 may provide isolation between computing performed within the virtual computer 810 and computing performed outside the virtual computer 810 through the host operating system 830. For example, the virtual computer 810 may be unaware of any computing performed outside of the virtual computer 810. Accordingly, an application executed within the virtual computer 810 generally cannot access an application executed outside the virtual computer 810.

As shown in FIG. 8B, the guest kernel 826 may include a virtual computer control application ("VCCA") 822 and a virtual computer monitor application ("VCMA") 824. The VCCA 822 may manage the operation of the virtual computer 1310. For example, as shown in FIG. 8B, the VCCA 822 may create one or more virtual browsing environments ("VBE") 812 (e.g., VBE 1 812 a, VBE 2 812 b, and VBE 3 812 c). Once created, the VCMA 824 may monitor the operation of each VBE 812 and may report each VBE's operation to the VCA 834. To create a VBE 812, the VCCA 822 may use one or more virtualization modules or applications, such as OpenVZ, UnionFS patches, Solaris Zones, BSD Jail, or combinations thereof.

It is known that internet-enabled applications run side-by-side with all other desktop and system software with the privileges of the user. As a result, when a compromise occurs through the Internet, the entire system can be compromised by a single vulnerability in an Internet-enabled software such as a Web browser or an email client. By simply browsing to a Web page, a user can compromise their system, sometimes irreversibly.

In an embodiment, the system works by launching a virtual machine for each Internet-enabled or untrusted application that is started. The virtual machine provides a pristine guest operating system (OS) for the Internet-enabled or untrusted application that is launched. This operating system may be an operating system unmodified from the original version delivered by the manufacturer or another version suitably configured for the task of running intended applications. The virtual machine and its guest operating system may be temporally limited to exist only for the duration of the session of the application. When the user exits the application, the virtual machine can be destroyed. For the duration of the session, the virtual machine provides an isolated environment from the host machine from which it is launched. The virtual machine provides a level of isolation from the host machine that is the equivalent to running a physically separate machine from the host machine. Any attacks that occur on the machine via an Internet connection can compromise only the virtual machine that is started up for that session. When the session is terminated, so is the virtual machine and the compromise. With each new session, a pristine new virtual machine is started up, meaning that any malicious software that was downloaded or planted during a prior session is no longer present. The underlying host operating system does not need to maintain an Internet connection. As a result, Internet-based attacks have a very limited ability to compromise the host operating system.

Figure 9:
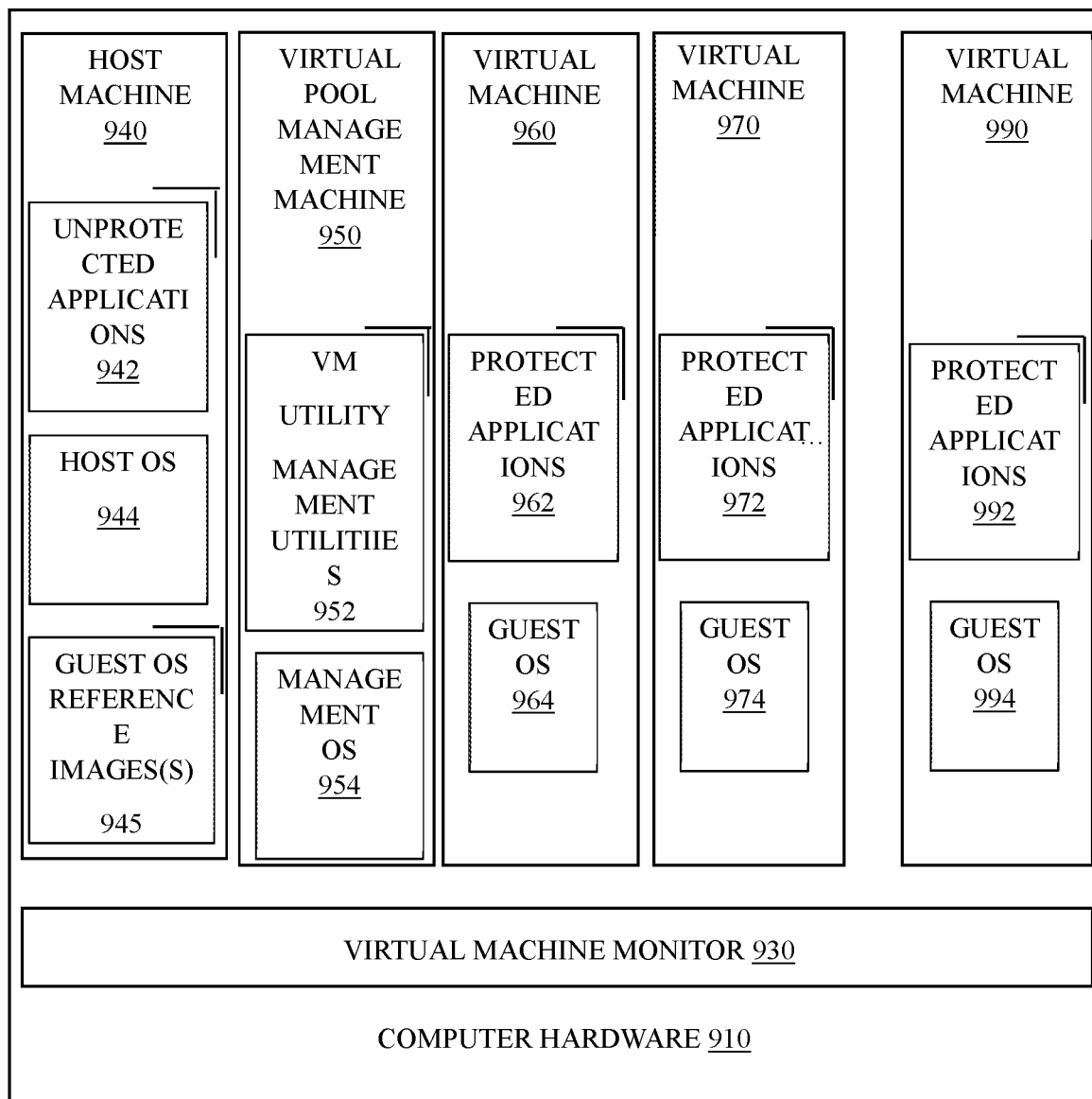
FIG. 9 is a block diagram of a virtual machine architecture of an aspect of an embodiment of the present invention to prevent malicious software attack.

According to an embodiment, an architecture shown in FIG. 9 uses the standard virtual machine architecture with the Virtual Machine Monitor (VMM) 930 running on the computer hardware 910, and host operating systems (944, 964, 974, and 994) running on top of the VMM 930. A host operating system (OS) 944 is defined as the default machine the user normally uses and is the machine whose desktop is presented to the user. Guest operating system (964, 974 and 994) are created by request when a protected application (962, 972 and 992) is launched, or created in advance to enable higher performance when launching protected applications (962, 972 and 992) into pre-instantiated guest operating system (964, 974 and 994). A Virtual pool management machine 950 may be bootstrapped along with the Host operating system OS 944 and a reference guest operating system image 945 that is used for clones of the reference guest operating system image 945. The Virtual pool management machine 950 is used for command, control, and lifecycle maintenance of the guest OSs (964, 974 and 994) based on the instructions from the host operating system OS 944. The number of guest OSs instantiated may be dependent on the number of protected applications launched and the performance limits of the underlying hardware. The VMM 930 and VIRTUAL POOL MANAGEMENT MACHINE 950 should support live capture of the full system state in a file for subsequent replay. This file is called a "snapshot" of system state.

The host operating system 944 may be configured for higher security so that it is unable to make Internet connections itself. The guest operating systems (964, 974 and 994) may be free to make direct Internet connections; however, they should be restricted from freely accessing the host operating system 944 by the virtual machine monitor (VMM) 930 that runs in its own hardware protection domain which provides hardware-equivalent strong isolation between the virtual machine and its host operating system. The guest operating systems (964, 974 and 994), which are pristine builds of the OS, should also be "root secure", which means that even if one of the guest operating systems (964, 974 and 994) is compromised to a root user level or the kernel itself is compromised, the host operating system 944 itself should not be compromised by the compromised guest operating system. Once a guest operating system is destroyed (upon closure of the protected application that started the guest OS), the compromise is now removed from the system.

As mentioned earlier, a reference guest operating system image 945 may be booted along with the host operating system OS 944. A snapshot of the reference guest operating system image 945 may be taken, then used to derive subsequent VM images by cloning it, i.e., creating a replica image of the reference guest OS. When a new untrusted application is to be started, a dispatch instruction is sent from the Host operating system OS to the Virtual Pool Management Machine 950, which then creates a VM for the application using the reference guest operating system image, if the VM has not already been created. By cloning and pre-booting reference images, the response time for instantiating the application should be on par or even faster than the usual response time for starting a new application for users.

As described, FIG. 9 shows an embodiment of the present invention where virtual machine monitor (VMM) 930 runs directly on computer hardware 910. In this embodiment, every host machine (940, 950, 960, 970 and 990) is essentially a guest machine to the computer hardware. In this setup, the unprotected host applications 942 run on the host machine 940 natively and the host operating system 944 runs these unprotected host applications 942. In contrast, the guest virtual machines 960, 970 and 990 run protected applications (962, 972, and 992 respectively) that may talk to a network under guest operating systems (964, 974 and 994 respectively).

The guest operating systems 964, 974, and 994 are each cloned from one of the guest operating system images(s) 945, and the images 945 should be pristine snapshots of a running operating system. To increase speed, the snapshots may also include running applications. For example, an image 945 of an operating system for an email virtual machine can include a copy of an email application running under the operating system.

The virtual pool management machine 950 runs a series of virtual machine management utilities 952 under a management operating system 954. These utilities 952 include functions that: create, destroy, put to sleep, and wake up virtual machines. The utilities also maintain a list that matches applications to virtual machines. In other embodiments, these same functions may be performed by pool management utilities running on a host machine.

Figure 10:
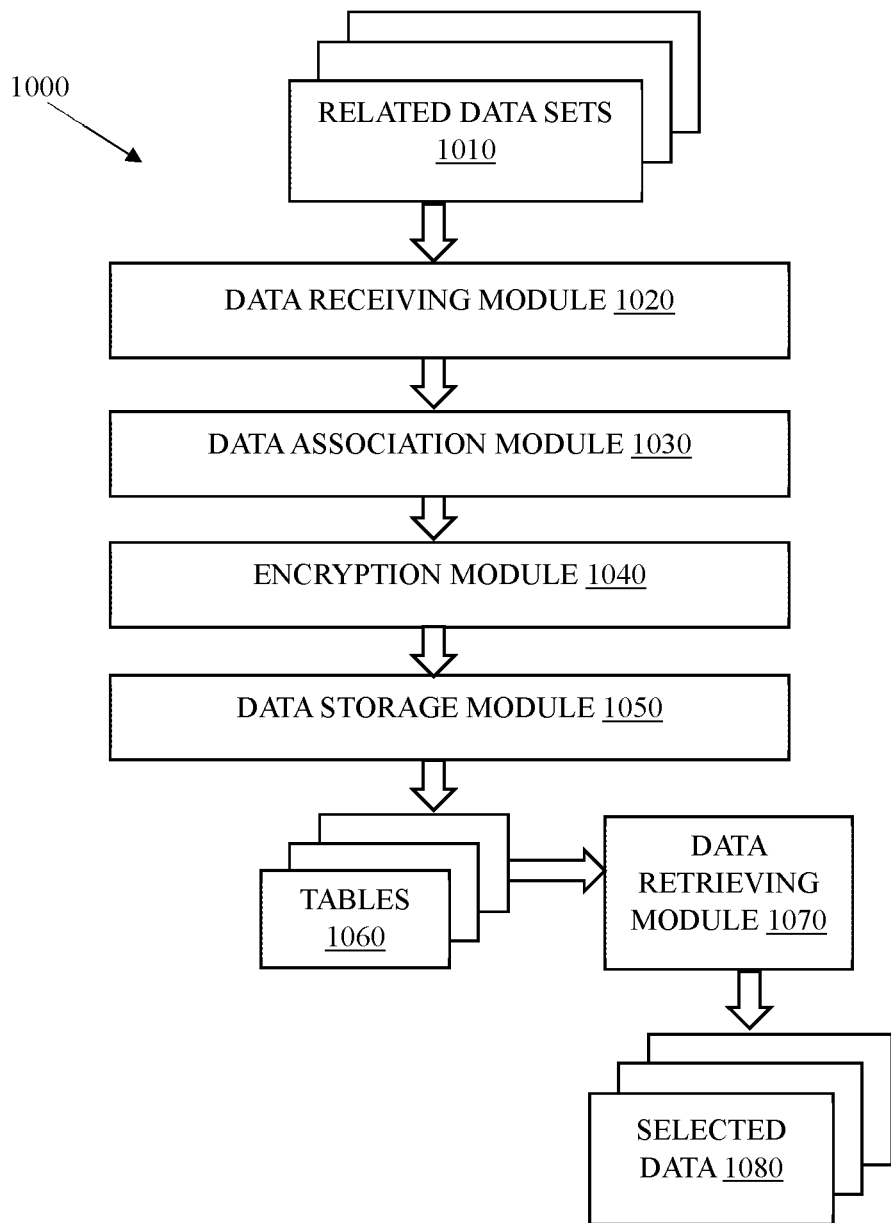
FIG. 10 is a block diagram for securing sensitive data associations for related data values of an aspect of an embodiment of the present invention.

In an embodiment, sensitive data associations for related data values are protected. FIG. 10 is a block diagram of a system 1000 for protecting sensitive data associations according to an aspect of an embodiment of the present invention. The block diagram shows a multitude of modules. As shown, the system includes a data receiving module 1020 configured to receive a set(s) of related data values 1010.

The set(s) of related data values 1010 preferably include at least a first data value and a second data value. The system normally operates against rule(s) that indicate which data value associations need to be kept secret. In the absence of such a rule, a default rule may be used such as the association of the first data value and the second data value needs to be kept secret.

A data association module 1030 may be configured to associate the first data value to a first data field; and the second data value to a second data field. An encryption module 1040 may then create first encrypted data by encrypting the first data value using a first encryption key; and create second encrypted data by encrypting the second data value using a second encryption key. A data storage module 1050 is configured to store: the first data value in a first data table 1060; the second data value in a second data table 1060; the first encrypted data in the second table 1060; and the second encrypted data in the first table 1060.

A data retrieving module(s) 1070 may be used to retrieve: the first data value by decrypting the first encrypted data using a first decryption key and/or the second data value by decrypting the second encrypted data using a second decryption key. As with the method embodiments, there are many possibilities for the encryption and decryption of keys. The encryption key and the decryption key may be the same symmetric key. The encryption keys may be different or the same. Similarly, the decryption keys may be the same or different. The choice of keys should be made carefully to ensure that the data relationships in the rule(s) be kept secret. In some embodiments, the rule may be received from an external source. In the absence of an external rule, an internal rule or a default rule may be used.

In an embodiment, there is a tool for storing data records in a data store that is scalable and that allows a user to define their encryption and relieves a user from the task of managing keys used for data security. In an embodiment, application data and associated encryption key(s) are stored on at least k+1 remote servers using Linear Hashing (LH*) addressing. At least k+1 buckets are created on separate remote servers. At least k+1 key shares are generated for each of at least one encryption key. Each encryption key has a unique key number. Each key share is stored in a different key share record. Each of the key share records is stored in a different bucket using LH* addressing. Encrypted application data is generated by encrypting the application data with the encryption key(s). The encrypted application data is stored in encrypted data record(s). Each of the encrypted data records is stored in a different bucket among the buckets using LH* addressing.

Figure 11:
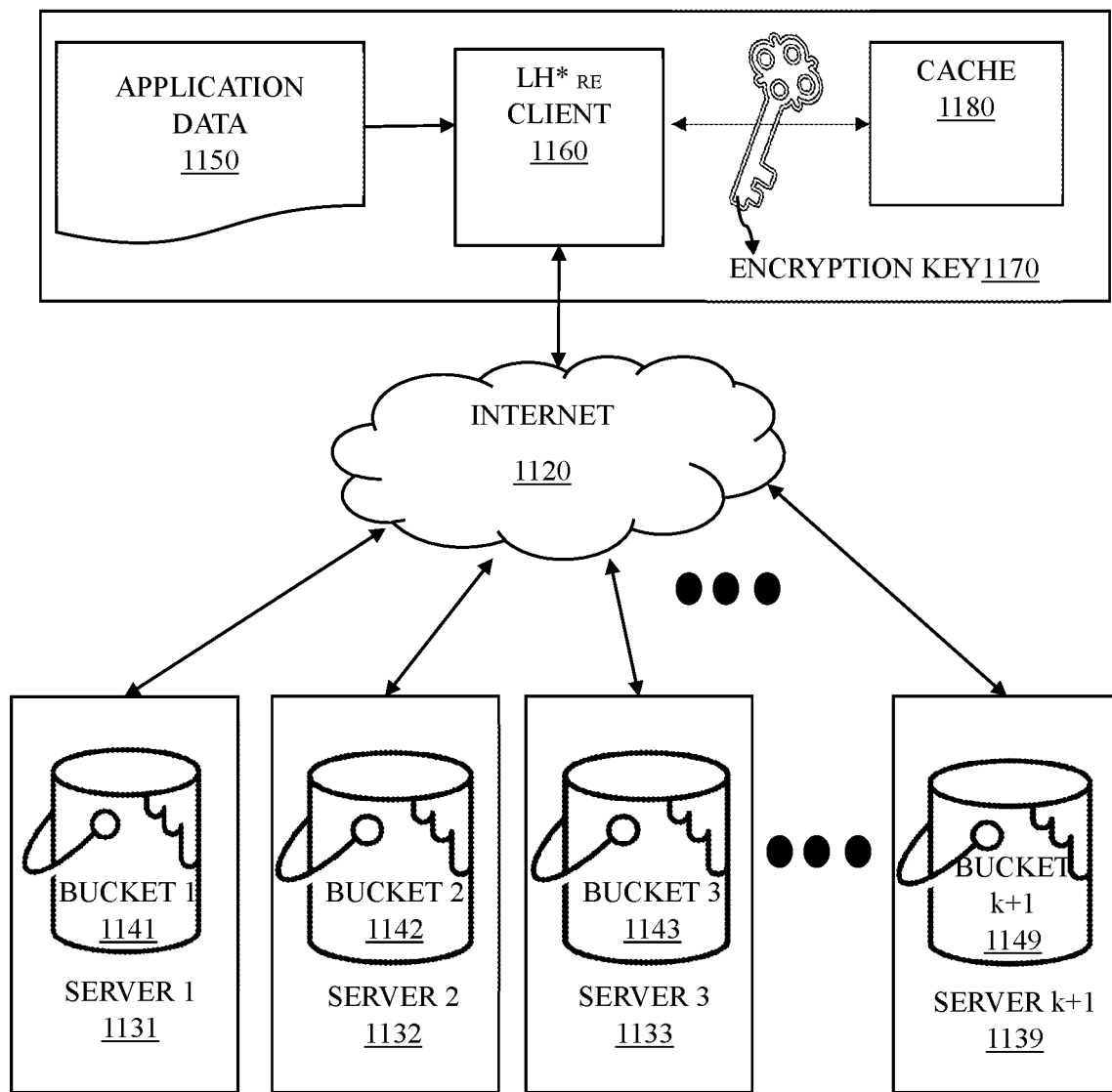
FIG. 11 is a system block diagram showing an example client interacting with k+1 servers that allows a user to define their encryption and relieves a user from the task of managing keys used for data security, as per an aspect of an embodiment of the present invention.

FIG. 11 is a system block diagram showing an example client 1110 interacting with k+1 remote servers (1131, 1132, 1133, . . . 1139) as per an aspect of an embodiment of the present invention. In these embodiments, one or more of clients (1110, 1111, . . . 1119) may have an LH*RE client 1110 configured to store a version of application data 1150 encrypted with an encryption key 1170 on remote servers (1131, 1132, 1133, . . . 1139). The remote servers (1131, 1132, 1133, . . . 1139) will likely be specialized servers configured to communicate with many client systems (1110, 1111 . . . 1119) and manage data buckets (1141, 1142, 1143, . . . 1149). The remote servers (1131, 1132, 1133, . . . 1139) may be geographically diverse. Some of the remote servers (1131, 1132, 1133, . . . 1139) may also be under the control of various organizations. In this way, the stored data may become harder for a third party to locate and retrieve all of the stored application data 1150 and key(s) 1170 from the data. Embodiments of the LH*RE client 1160 may be implemented as a computer readable storage medium containing a series of instructions that when executed by one or more processors on clients (1110, 1111, . . . 1119), causes the one or more processors to store application data 1150 on at least k+1 remote servers (1131, 1132, 1133, . . . 1139). In these embodiments, k is a freely set parameter of the system.

Figure 12:
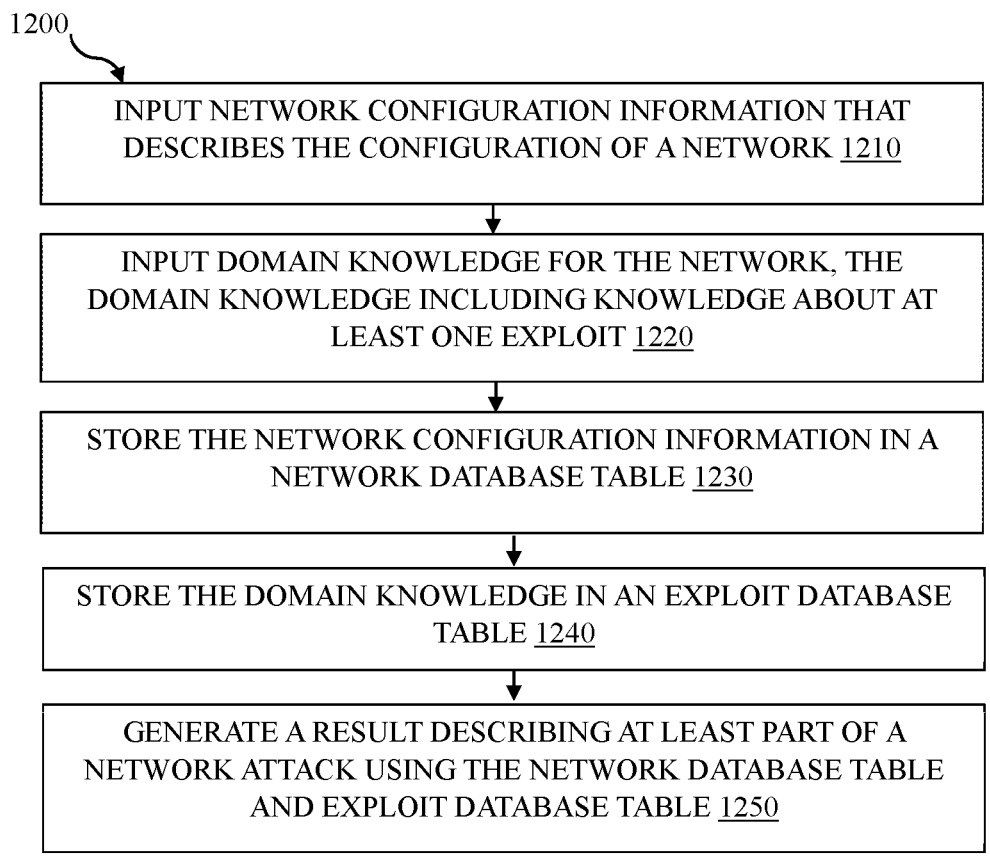
FIG. 12 is a flow diagram describing a method for determining at least part of a network attack according to an embodiment of the present invention.

Attack graphs depict ways in which an adversary exploits system vulnerabilities in a network such as a computer network. Attack graphs may be important in defending against well-orchestrated network intrusions. FIG. 12 is a flow diagram of an aspect of an embodiment where the network configuration information input module is preferably configured to input network configuration information that describes the configuration of a network in 1210. The domain knowledge input module is preferably configured to input domain knowledge for the network in 1220. Domain knowledge may include knowledge about various exploits in the network. The network configuration information storage module is preferably configured to store network configuration information in at least one network database table in 1230. Similarly, the domain knowledge storage module is preferably configured to store the domain knowledge in at least one exploit database table 1240. The result generation module is preferably configured to generate a result using the network database table and exploit database table in 1250. The result may be generated in many ways.

In an embodiment, an Intrusion Detection System (IDS) is deployed on the system. An IDS is software and/or hardware designed to detect unwanted attempts at accessing, manipulating, and/or disabling computer systems, mainly through a network, such as the Internet. An intrusion detection system is used to detect malicious behaviors that can compromise the security of networked computer systems. An IDS may include Sensor(s) that are deployed at strategic locations in the network, which monitor traffic at the sensor location and generate security events upon detection of malicious behaviors; A central engine that records events (e.g., in a database) logged by the sensors; and Console(s) to monitor events and control the sensors. In some IDS implementations, all three components are combined in a single device or appliance. In a true distributed system, numerous sensors are deployed at various points in the network, which communicate over secure channels to the central engine. Multiple consoles may then interact with the central engine. In network-based intrusion detection systems (NIDS), sensors are located at monitoring points in a network. Traditionally, sensors may be placed at network borders or in a network demilitarized zone (DMZ), with the assumption that attacks are launched from outside the network to be defended. The sensor monitors network traffic at its point of deployment and analyzes the traffic content for patterns of malicious behavior.

Embodiments of the present invention locate the placement of intrusion detection system (IDS) sensors and prioritize IDS alerts using attack graph analysis. One embodiment predicts multiple ways of penetrating a network to reach critical assets. The set of such paths through the network constitutes an attack graph, which may be aggregated according to underlying network regularities, reducing the complexity of analysis. By knowing the paths of vulnerability through our networks, one may reduce the impact of attacks. IDS sensors may be placed to cover the attack graph, using a minimal number of sensors. This should minimize the cost of sensors, including effort of deploying, configuring, and maintaining them, while maintaining complete coverage of potential attack paths. An embodiment addresses the sensor placement as an instance of the nondeterministic polynomial-time (NP) hard minimal set cover problem using an efficient greedy algorithm. Once sensors are deployed and alerts are raised, a predictive attack graph may be used to prioritize alerts based on attack graph distance to critical assets.

Figure 13:
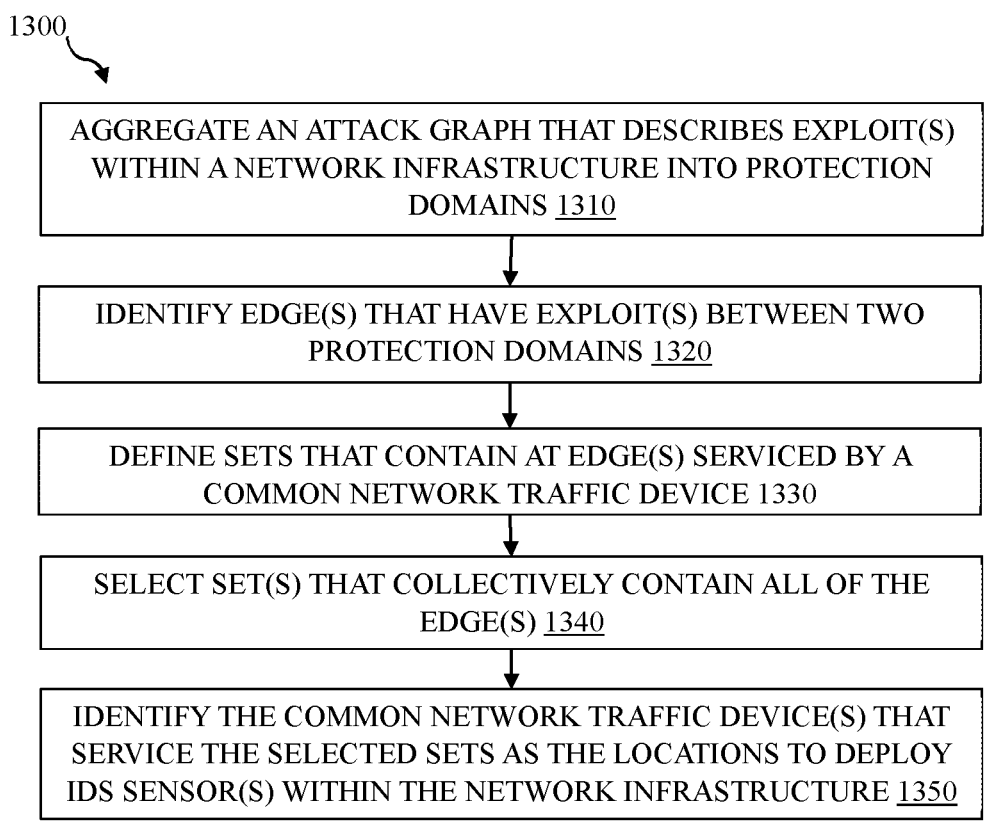
FIG. 13 depicts a flow diagram for a computer readable storage medium demonstrating instructions that cause the processor to perform a method for identifying locations to deploy intrusion detection system (IDS) Sensors within a network infrastructure, as per an aspect of an embodiment of the present invention.

An embodiment of the present invention, as exemplified in FIG. 13, is a computer readable storage medium that contains instructions that when executed by at least one processor, causes the processor(s) to perform a method 1300 for identifying locations to deploy IDS sensor(s) within a network infrastructure. The method 1300 for identifying locations to deploy IDS sensor(s) within a network may comprise aggregating an attack graph that describes exploit(s) within a network infrastructure into protection domains. The attack graph may be configured to describe exploit(s) in at least a part of the network infrastructure. Further, the embodiment may include identifying edge(s) that have exploit(s) between two protection domains 1320, defining sets that contain edge(s) serviced by a common network traffic device 1330, selecting set(s) that collectively contain all of the edge(s) 1340, and identifying the common network traffic device(s) that service the selected sets as the locations to deploy IDS sensor(s) within the network infrastructure 1350.

In an embodiment of the present invention, the selecting set(s) that collectively contain all of the edge(s) 1340 may further include selecting set(s) that cover critical path(s) through the network infrastructure that lead to a critical asset. The set selection method may further include selecting set(s) that cover critical path(s) through the network infrastructure that starts at an assumed threat source. Further variations of this embodiment may allow the set selection method to include selecting a minimal number of sensors necessary to cover critical path(s) through the network infrastructure. The set selection method may also further include utilizing a greedy algorithm. The greedy algorithm favors large sets that contain edge(s) that are infrequently used. Frequency is the number of times an edge appears across all sets.

In an embodiment of the present invention, the method 1300 for identifying locations to deploy on IDS sensor(s) within a network may further include prioritizing alerts from IDS sensors deployed within the network infrastructure using at least one attack graph distance to at least one critical asset. Attack graph distance may be measured in multiple ways such as: 1) the number of edges that are traversed to reach critical assets; 2) the number of protection domains crossed; and 3) the number of network traffic devices.

The term "drug vending system" refers to an automatic medicine vending machine with a self-contained on-site pill dispensing mechanism and a storage facility for the plurality of pills that can be dispensed based on the user requirement. Drug vending machines are the automated machines used to dispense prescription drugs, medical devices, and miscellaneous medical products by paying through an interface. The medical vending machines can be installed at a suitable place depending on the utility of the machine.

The term "scanner" or "prescription scanner" refers to an electronic device which can capture images from physical items and convert them into digital formats, which in turn can be stored in a computer, and viewed or modified using software applications.

The term "password" as referred herein is sometimes called a passcode, is secret data, typically a string of characters, usually used to confirm a user's identity.

The term "Proxy user" as used herein refers to a user that acts as a substitute for another user to complete tasks.

Figure 14A:
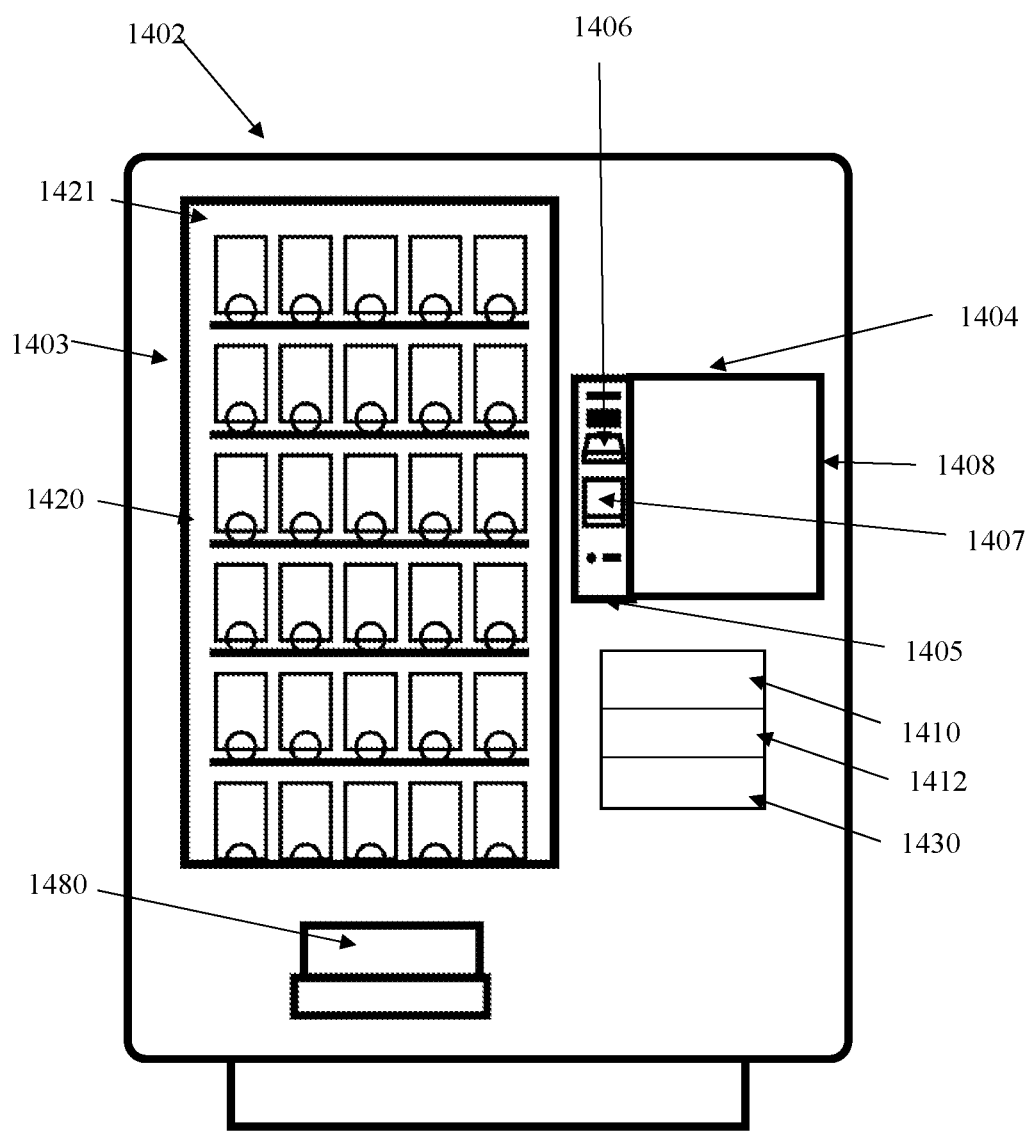
FIG. 14A shows a perspective view of a drug vending system according to one embodiment.

In an embodiment, as shown in FIG. 14A, the system comprises a drug vending system. The system 1402 comprises the drug storage system, the user interface 1404, input interface 1405, the output interface 1408, processor 1410, memory 1412, and the communication module 1430 embedded on to the drug vending system 1402. The drug vending system 1402 comprises a biometric scanner 1406 and a prescription scanner 1407 that is in direct communication through the communication module 1430 with the processor 1410 and memory 1412 to allow the dispensing of the drug from the drug vending system 1402. The drug vending system 1402 dispenses the drug after receiving the prescription, verifying the prescription, verifying the authentication, by turning on the actuating mechanism to open the outlet to dispense. If the user interface 1404 by the processor 1410 concludes a failure to authenticate, drug vending system 1402 prevents unauthorized dispensing of the drug containers and items stored therein. During operation, the drug vending system 1402 may be activated, upon authentication of a user. The input interface 1405, the output interface 1408, the processor 1410 and the memory 1412, are mounted on the drug vending system 1402. The input interface 1405 comprises an authentication sensor; a keypad; a touchpad; a scanner; and a RFID reader. The scanner comprises a Universal Product Code indicia scanner, a Quick Response code scanner, a high-capacity color barcode scanner, and a near-field communication scanner. The output interface comprises an LED display, an LCD display, a buzzer, an alarm, and a speaker.

In an embodiment, the drug vending system 1402 comprises a cover 1421 to the container 1420. The cover 1421 to the container 1420 comprises at least one of a lid, a door, a hinged cover, a magnetic cover, and a sliding door. The drug storage further comprises a lock 1423 associated with the container 1420 to selectively activate and deactivate the container to allow an opening of the container, communicatively coupled with the processor of the system to selectively activate and deactivate the container to allow an opening of the container. In an embodiment, the cover 1421 may be a transparent or a translucent material that a user can see through the cover. The cover is made of a tamper proof material that does not break in case of a robbery or break in attempt. In case of tampering with the cover, an alarm shall be raised immediately to notify that the drug vending system is being tampered with. In an embodiment, the drug vending system is a vault system which is tamperproof. The cover or the door of the drug vending system is a door to a vault. The door may not be a see through door like conventional vending machines.

In the open configuration, the container 1420 of the drug storage and vending system 1402 may be filled with drug containers comprising vials, syringes, pillboxes, and the like.

According to one embodiment, drug storage and vending system 1402 can also support multi-drug capabilities for support of dynamic, complex, and multi-provider medication regimens. The use of unit dose packaging in the cartridges accommodates complex drug regimens. Such packaging equipment permits several different drugs to be placed in a single packet, and the automated pharmacy equipment permits the packaging of sequential packets with different regimens in a given cartridge should it be necessary to include additional drugs in two or more packets. In this case the drug vending system 1402 can dispense the additional packets in sequence. Also, a multi-cartridge design of the drug dispenser in the drug vending system 1402 can permit prescription modifications from the same, or other, providers without having to change the initial cartridge. For example, if a second, short-term prescription for an antibiotic is ordered by a practitioner it can be added to the patient's drug regimen by dispensing it from a second (third or fourth) cartridge. Long term changes can be handled in the same way, except that once the primary cartridge's contents are exhausted it can be refilled with the new drug added to the single packet regimen. Also, multiple cartridges permit prescription refills prior to the primary cartridge becoming empty. The refill cartridge can be placed in drug vending system 1402 but not used until the primary is empty. The refill can then become the primary and the empty can be returned to the pharmacy for refills. This dispensing management can be handled automatically by the drug vending system 1402 by matching the contents of the individual cartridge(s) with the patient's prescription and dispensing what is appropriate, avoiding duplicate dispensing, reordering cartridges as they approach empty, and dispensing from multiple cartridges when appropriate to fill the ordered prescription(s).

According to one embodiment, drug vending system 1402 can additionally or alternatively manage prescription and Over the Counter (OTC) drug compatibility. The addition of this capability can be facilitated by the multiple cartridge design of the drug vending system 1402, if implemented as such. That is, multiple cartridges can be loaded with prescription and Over the Counter (OTC) drugs but dispensed only in an order, combination, or on a schedule that does not create compatibility or interaction problems. Information for identifying and managing these compatibility or interaction problems can also be encoded into the on-board memory of the individual cartridges by the pharmacy or caregiver before being dispensed.

According to one embodiment, the drug vending system 1402 may additionally or alternatively support delivery validation functions to provide point-to-point safe and secure medication delivery, refills, and returns. In such implementations, the drug vending system 1402 can notify the pharmacy and/or provider or caregiver when a new cartridge is delivered, when it has been loaded in the drug vending system 1402, when the user dispenses medication and when the contents of a cartridge is about to be exhausted, and thereby providing an automated refill request. The refill of the cartridge can be safely and effectively accomplished using the secure cartridges as described herein. These allow the drug provider to ship a self-addressed envelope with the cartridge. When empty, or at the end of use (and unused drugs are still contained in the cartridge), the patient can place the cartridge into the envelope and drop it in a mailbox. The pharmacy can then refill the cartridge (or the unused drugs are safely disposed op, and the data stored in the memory of the cartridge can be updated at the pharmacy and the cartridge can be returned to the patient by the same method.

According to one embodiment, drug vending system 1402 may additionally or alternatively provide automated loading and dispensing that allow pharmacy-level expertise to properly provision the system. In such implementations, the drug vending system 1402 uses the preloaded cartridges that have been filled by professional pharmacy personnel using automated packaging systems. This not only prevents mistakes in the drug provisioning process but also prevents drug diversion and abuse that is a natural byproduct of an open, unsecured container and manual drug handling and loading in the home.

The drug vending system 1402 may also include a user interface 1404 operating dispensing and/or loading functions of the drug vending system 1402. In some cases, the user interface 1404 may comprise or include, a biometric scanner, such as a fingerprint scanner, a fingerprint, an eyeblink scanner, a retina scanner, an iris scanner, an eye scanner, and a facial image scanner to read biometric information of a user of drug vending system 1402 to be used to authenticate the user before dispensing or loading of medication from or into the drug vending system 1402. For example, the user can touch the button which may also take a biometric sample to be verified and, assuming the user is authenticated, a medication packet containing the prescribed medication to be taken and this scheduled time can be dispensed from one of the medication cartridges of the drug vending system 1402.

The drug vending system 1402 can also include an interactive display such as an LCD and a touchscreen display for displaying information related to the medication and/or functions of the drug vending system 1402. For example, the display may show a schedule for dispensing medication, types of medications in the cartridges currently loaded in the drug vending system 1402, an amount of medication remaining in the medication cartridges etc. In some cases, the display may comprise a touch screen providing access to other functions and features of the drug dispenser including, but not limited to, setting and silencing alarms, initiating and/or canceling dispensing, user authentication, scanning through applications installed in the interactive display and/or loading operations, requesting refills, etc.

In an embodiment, drug vending system 1402 comprises one or more actuating mechanisms 1450. The processor 1410 may be configured to control the actuating mechanism 1450 based on inputs received from the user from the user interface 1404, or another device. For example, the patient may authenticate their identity and enter a prescription through the user interface 1404 on drug vending system 1402 to dispense a medication, the processor 1410 in turn controls the actuating mechanism 1450 to dispense the appropriate medication from one or more vials or medication cartridges from the one or more pill magazines (e.g., collection of vials) from an outlet 1480. The processor 1410 may be also configured to control the actuating mechanism 1450 at a predetermined schedule to automatically dispense the medication at appropriate times from the outlet 1480, or in response to an external trigger received as input data.

In an embodiment the drug vending system 1402 may be an Internet of Things device, or a "thing" embedded with electronics, software, sensors, and connectivity to enable objects to exchange data with different devices, authorities, and components (authorities for e.g., doctor, pharmacy, health care providers).

In an embodiment, the user interface 1404 is remotely located. The user interface 1404 is a remote device aiding remote access to drug vending system 1402. The user interface 1404 may also include an application programming interface and a web application connected with the input interface 1405 as the mobile devices and computers have a biometric sensor for biometric information of the user. The application programming interface and a web application may also have a unique identity to be set for allowing to dispense the drug from the drug dispenser. The processor 1410 is configured to be in communication with the input interface 1405 through the communication module 1430 which facilitates communication with the server and the drug vending system 1402.

In an embodiment, the input interface 1405, the output interface 1408, the processor 1410, and the memory 1412 are added or retrofitted to an existing drug vending system 1402 to add access control to drug vending system 1402. In some applications, drug vending system 1402 may include the user interface 1404, the processor 1410, and the memory 1412 are in the original manufacture or assembly.

In an embodiment, the input interface 1405 is inside a remote device aiding remote access to the drug vending system 1402. The authentication of the user may also include authentication through an application programming interface and a web application connected with the authentication sensor, as the mobile devices and computers have a biometric sensor for a biometric information of the user. The application programming interface and a web application may also have a unique identity to be set for the dispensing of the drug from the drug dispenser. The processor 1410 is configured to be in communication with the input interface 1405 through the communication module 1430 which facilitates communication with the server and the drug vending system 1402. The communication module 1430 comprises any suitable wireless technology such as cellular which can include, but is not limited to, Global System for Mobile communication, Code Division Multiple Access, Wireless in Local Loop, General Packet Radio Services, or it can also utilize Low Power Wide Area Networks (LPWANs) such as Bluetooth, Bluetooth low energy, Wi-Fi, Z-Wave, Thread and Zigbee. Z-Wave is a wireless communication protocol used primarily in smart home networks, allowing smart devices to connect and exchange control commands and data with each other.

In an embodiment, the communication module 230 may comprise a wired connection such as LAN, WLAN and WAN.

In an embodiment, the prescription is received from a digital medium and as a blockchain token. The digital medium comprises a message, and an email. The processor interacts with the server to check a drug name, a last dispensing time, a dosage time, a quantity of the drug delivered to the user in a day, quantity of the drug accessed by the user in the day before dispensing the drug to the user.

In at least one such embodiment, the user is able to register the prescription by scanning or inputting a unique prescription code into the user interface 1404 through a scanner 1407, with the prescription code containing the necessary information related to the prescription distribution, including a dosage interval (i.e., the amount of time between distributing the drug containers) and a dosage quantity (i.e., the quantity of drug to be distributed at each dosage interval). In at least one such embodiment, the patient is able to register the prescription by scanning a visual barcode (such as a Quick Response (QR) code, for example) using a scanner 1407 of the user interface 1404.

In at least one embodiment, the processor 1410 encrypts each of the biometric information, unique identity, and prescription code with a unique hash value (such as a random number, in at least one embodiment) to be stored in the corresponding database of the user, thereby creating a unique link. In this way, based on the user's unique identity, biometric information and prescription code prevents anyone else from accessing the drug container from drug vending system 1402.

In an embodiment, the drug vending system is a pull up or a walk up system. A user can pull up or walk up to the nearby drug vending system to receive the prescribed drug containers. The drug vending systems may be installed at least one of a pharmacy and a drug store. In an embodiment, the drug vending systems may be installed at a box store. Users may receive their prescription 24/7 in a contactless and contact-free transaction through a kiosk. Users pull up or walk up to a kiosk with their encrypted block chain authentication code. Once a prescription is generated the user might receive a message through the system 1400 to collect the prescription from the drug vending system. The drug vending system may be installed at the pharmacies, drug stores, grocery stores, supermarkets, hypermarkets and box stores with collaboration with companies like CVS Health Corporation having subsidiary: CVS Pharmacy, CVS, Longs Drugs, Navarro Discount Pharmacy, Drogaria Onofre, Target, HealthHub; Walgreens Boots Alliance having subsidiary: Walgreens, Duane Reade, Boots, Farmacias Benavides; Ahold Delhaize; MedPlus Health Services Pvt. Ltd. (India); Rite Aid Corp.; Albertsons Companies Inc.; Osco Pharmacy and Say-on Pharmacy; Walmart Inc.; Kroger Company; Costco Wholesale Corp; Amazon; CostPlus Drug Company—Mark Cuban; Chongqing Tongjunge Drugstores Co. Ltd (China); PHOENIX Group (Europe).

Figure 14B:
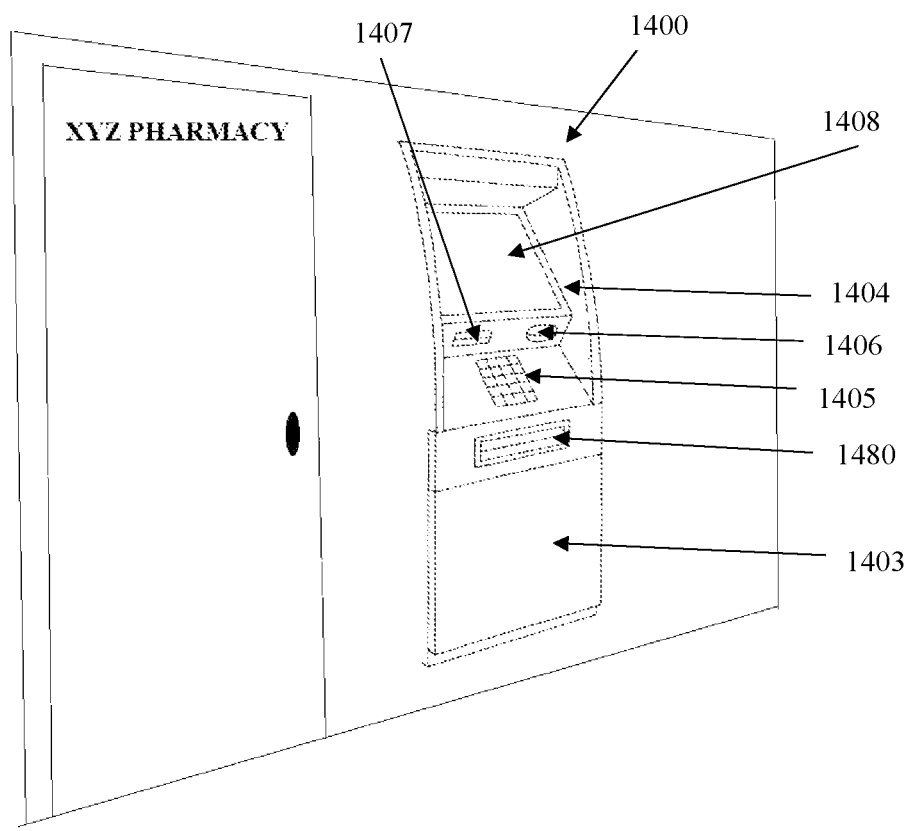
FIG. 14B shows a perspective view of the drug vending system according to another embodiment.

In an embodiment, as shown in FIG. 14B, the system comprises an automatic drug vending machine to dispense prescribed drugs. The system comprises the drug storage system 1403, the user interface 1404, input interface 1405, the output interface 1408, processor, memory, and the communication module embedded into the automatic drug vending machine 1400. The processor, memory, and the communication module are inside the automatic drug vending machine and are not shown in FIG. 14B. The automatic drug vending machine 1400 comprises a biometric scanner 1406 and a prescription scanner 1407 that are in direct communication through the communication module with the processor and memory to allow the dispensing of the drug from the automatic drug vending machine 1400. The automatic drug vending machine 1400 dispenses the drug after receiving the prescription, by verifying the prescription, verifying the authentication of the user, and turning on the actuating mechanism to open the outlet to dispense. If the user interface 1404 by the processor concludes a failure to authenticate, automatic drug vending machine 1400 prevents unauthorized dispensing of the drug containers and items stored therein. During operation, the automatic drug vending machine 1400 may be activated, upon authentication of a user. The input interface 1405, the output interface 1408, the processor and the memory are mounted in and/or on the automatic drug vending machine 1400. The input interface 1405 comprises an authentication sensor; a keypad; a touchpad; a scanner; and an RFID reader. The scanner comprises a Universal Product Code indicia scanner, a Quick Response code scanner, a high-capacity color barcode scanner, and a near-field communication scanner. The output interface comprises an LED display, an LCD display, a buzzer, an alarm, and a speaker.

In an embodiment, the automatic drug vending machine is wall mounted on a road-side. The roadside system may enable 24×7 access to the system to access the drug containers. If the pharmacy or the box store is closed, the automatic drug vending machine can still be operative as the machines are situated outside the store as shown in FIG. 14B.

In an embodiment, there is a provision in the system to destroy the drug container if the drug container is not collected from the dispenser in a given period of time. The time period may be set by a pharmacy. The system may comprise an image sensor to detect whether a person is there to collect the drug container or not. If the image sensor detects an absence of the person to collect the drug, the system may destroy the drug container. The system actuates the actuator to destroy the drug container. In an embodiment, the system actuates the actuator of the outlet 1480 to take back the drug container into the system.

In an embodiment, there is provision for a proxy user to collect the drug container. The proxy user may be a close relative or friend to the patient to which the drug is prescribed. The proxy user may collect the drug container when a user is not able to reach out to the system due to unavoidable circumstances. The unavoidable circumstances may be bad health conditions due to which the user may not be able to move or come to the pharmacy or the store. The proxy user may be registered with the system by providing the user identification details into the system. The proxy user also goes through the same authentication process to access the drug container as the other users. The proxy user needs to provide a unique identification and a biometric identification first. Once the unique identification and the biometric identification is authenticated the system receives a prescription from the proxy user. The prescription is verified by the system and the drug container comprising the drug is dispensed through the system to the proxy user.

Figure 15:
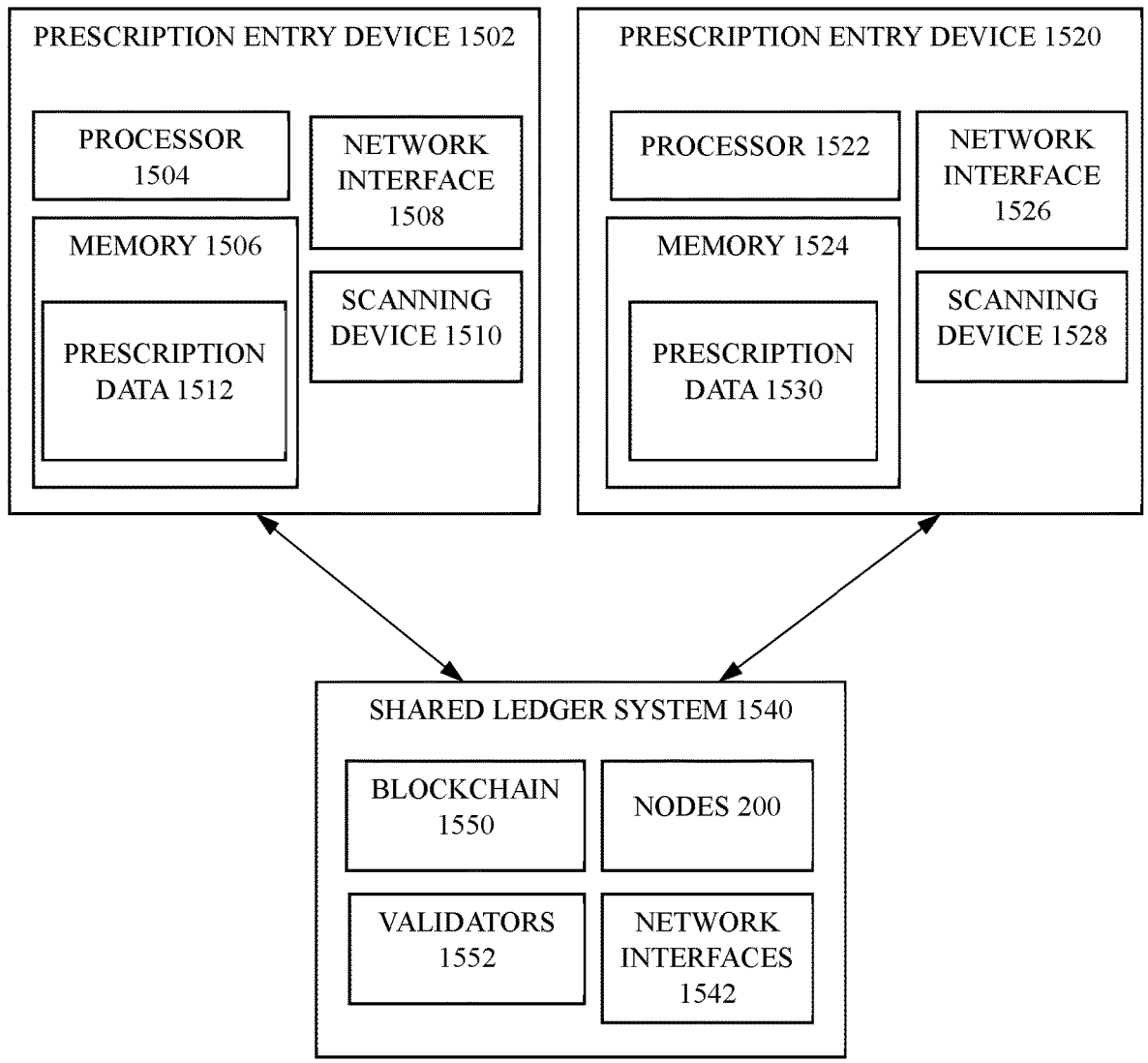
FIG. 15 shows a block diagram of prescription receiving and verification system.

With reference now to FIG. 15, a system 1500 is illustrated. System 1500 includes a prescription entry device 1502, a prescription verification device 1520, and shared ledger system 1540. Shared ledger system 1540 includes blockchain 1550, nodes 200, validators 300, and network interface 1542 associated with each of blockchain 1550, nodes 200 and validators 300 and configured to allow communication with and between blockchain 1550, nodes 200 and validators 300 and any other computing device via wired or wireless connections, the internet, or any other method of communication.

Prescription entry device 1502 includes at least one processor 1504, memory 1506, and a network interface 1508. In some aspects, prescription entry device 1502 may be provided to physicians, other healthcare professionals, hospitals, or other entities that create prescriptions. For example, prescription entry device 1502 may be a computing device associated with or owned by the physician, other healthcare professional, hospital, or other entity. In some aspects, prescription entry device 1502 also includes a scanning device 1510 that is configured to digitally scan prescriptions and generate prescription data 1512 based on the scanned prescriptions for storage in memory 1506. In some aspects, prescription data 1512 for each prescription may include an image of the prescription. In some aspects, scanning device 1510 and prescription entry device 1502 may be separate devices that are in communication via network interface 1508.

Memory 1506 may include instructions, software, and/or programs that may be executed by processor 1504. Memory 1506 may also store prescription data 1512 generated by scanning device 1510.

Network interface 1508 may be configured to communicate with other computing devices, the internet, the cloud, or any other device, via wired or wireless technology. For example, network interface 1508 may be configured to communicate with shared ledger system 1540 via one or more network interfaces 1542 of shared ledger system 1540.

Scanning device 1510 may be any device that is capable of generating a digital image based on a hardcopy or a digital copy of the prescription. Example scanning devices 1510 may include multi-function printers, standalone scanning devices, digital cameras, smart phones, other smart devices, or any other scanning device that is capable of capturing a digital image and/or perform optical character recognition (OCR) of a prescription and generating prescription data from the digital image.

Prescription entry device 1502 may be used by a physician, other healthcare professional, hospital, or other entity that is authorized to issue prescriptions for patients. For example, a physician may "write" a prescription for a patient. Prescription may include prescriber information, e.g., a prescribing entity such as a doctor's office, hospital, or other entity, a list of physicians or other healthcare professionals, or other similar prescriber information. Prescription may include a patient name, a prescription issue date, drug information e.g., drug type, dosage and instructions, a quantity to be dispensed per refill, a number of refills, and a physician's signature. In some aspects, where the drug is a controlled substance, the prescription may also include additional information required by the government, for example, the physician's DEA number (not shown).

In some aspects, a prescription may be a hardcopy, for example, a piece of paper, card stock, or other material, and the physician may physically fill in the fields of the prescription as necessary to complete the prescription by hand. For example, the physician may physically write the patient's name, prescription issue date, drug information, quantity per refill, number of refill, on the prescription and may sign the prescription with a signature. The hardcopy of prescription may then be scanned by scanning device 1510 to generate prescription data 1512 which may be stored in memory 1506. In some aspects, scanning of the hardcopy of prescription by the scanning device 1510 may include generating a digital image of the prescription hardcopy.

In some aspects, the physician may generate a prescription using prescription entry device 1502 without generating a hardcopy of the prescription. For example, the physician may fill in each field of prescription digitally and the prescription data 1512 for the digital prescription may be stored directly in memory 1506 during scanning the prescription with scanning device 1510. The filled in version of the prescription may also be stored as part of the prescription data 1512 as a digital image. In some aspects, once the prescription has been completed digitally, the physician may print the prescription to a hardcopy, e.g., by a printing device (not shown) associated with prescription entry device 1502 and may provide the prescription to the patient.

In some aspects, a validation code, e.g., a hash, of prescription or prescription data 1512 may be generated. In some aspects, the validation code may, for example, be generated based on the information entered into the prescription by the physician or other medical personnel. For example, image processing may be performed on the prescription data 1512 to identify any text in the prescription and the validation code may be based on the identified text. In some aspects, the validation code may be generated based on, for example, the digital data that represents the prescription. In some aspects, the validation code may be generated based on the pixel values that form the image of prescription stored in the prescription data 1512. In some aspects, the validation code may be a hash of a file stored on prescription entry device 1502 that contains the prescription data 1512. For example, the validation code may be a hash of the prescription image file. An example of a validation code for prescription 502 may include "98770778965214190371 Timestamp: 2016-02-29 13:50:17 UST".

Once a prescription is generated a validation code is generated by scanning of the prescription. When a user goes to a drug vending system and scans a prescription on the drug vending system, the scanned prescription is compared with the validation code existing in the memory and with the shared ledger.

In some aspects, the validation code may be printed on the hardcopy of the prescription, for example, by a printing device (not shown) associated with prescription entry device 1502. In some aspects, for example, where the physician has handwritten the patient and drug information into the fields of the prescription, the physician may be provided with the validation code by prescription entry device 1502 and may manually write the validation code on the prescription for later use by a pharmacy or other entity that will dispense the prescription.

In some aspects, the validation code may be generated by shared ledger system 1540 at a time when the prescription data 1512 is submitted by prescription entry device 1502, e.g., via network interfaces 1508 and 1542, as a transaction for addition to blockchain 1550. For example, one or more nodes 200 or validator nodes 1552 may generate the validation code when the prescription data 1512 is received from prescription entry device and may add the validation code to the prescription data 1512 prior to appending the prescription data 1512 to a block for addition to the blockchain 1550.

Once prescription data 1512 for a prescription has been submitted to shared ledger system 1540 and a validation code has been generated and added to the prescription data 1512, prescription data 1512 may validated and added to a new block by a validator node 1552 of shared ledger system 1540. The validators may then reach a consensus and add the new block containing the prescription data 1512 to the blockchain 1550. In some aspects, only prescriptions received from verified prescribers, those using prescription entry devices 1502, may be validated for addition to the blockchain 1550. For example, if a prescription is received from a non-verified device, shared ledger system 1540 may deny entry of the prescription to the blockchain 1550. In some aspects, all or part of the prescription data 1512 may be encrypted when submitted for addition to the blockchain 1550 to protect patient privacy, for example, the prescription data 1512 may be encrypted by prescription entry device 1502 or the prescription data 1512 may be encrypted by shared ledger system 1540. In some aspects, an image of the prescription may be stored separately from the blockchain, for example, in a separate database, and the prescription data 1512 stored on the blockchain may include a link, e.g., a URL link, pointing to the prescription image.

In some aspects, prescription data 1512 may be checked against other prescriptions already added to blockchain 1550. For example, the validator node may determine whether there is already an active prescription for the listed patient for the same medication. If such a prescription exists, the shared ledger system 1540 may notify the prescribing physician, e.g., via prescription entry device 1502 and indicate that the prescribing physician should manually verify the existence of the prior active prescription. For example, the prior active prescription that is already appended to blockchain 1550 may include identification or contact information for a prescribing physician that may be used to verify whether the patient has already received a prescription for the same medication from another physician. This verification may be used to prevent doctor shopping where, for example, a patient may receive separate prescriptions for the same medication from more than one physician.

In some aspects, a physician or other medical personnel may wish to update or modify a prescription after the prescription data 1512 has been added to the blockchain 1550. In this case, for example, the physician may make the modification on the hardcopy of the prescription and may re-scan the hardcopy using scanning device 1510 to generate and store new prescription data 1512 in memory 1506. In some aspects, the physician may make the modification directly in the prescription data 1512 stored in memory 1506. Once the modification has been made, a new validation code may be generated based on the modified prescription data and the modified prescription may be submitted to shared ledger system 1540 for entry into the blockchain 1550 as a modification transaction. In some aspects, the modified prescription data may also include the validation code of the original transaction including prescription data 1512 as a reference. In some aspects, once a modification of a prescription has been received by shared ledger system 1540, the original prescription may be deactivated where, for example, any attempted use of an unmodified version of the prescription may result in an indication or warning that the unmodified version is no longer available for dispensation. For example, the prescription may be deactivated by submitting a deactivation transaction to shared ledger system 1540 for addition to blockchain 1550. The deactivation transaction may specify that the prescription is deactivated and may prevent any future use of the prescription unless the prescription is reactivated, e.g., by the submission of a re-activation transaction by prescription entry device 1502 to shared ledger system 1540.

In some aspects, shared ledger system 1540 may verify that the modified prescription data 1512 is received from the same physician or source as the original prescription data 1512. If the source is the same, the modification may be accepted and added to blockchain 1550. If the source is not the same, shared ledger system 1540 may deny entry of the modification to blockchain 1550. This may prevent a non-prescribing entity, or the wrong prescribing entity from submitting a modification to a prescription that was not originally issued by that entity. For example, in some aspects, each prescription entry device 1502 may be pre-verified by shared ledger system 1540 and may include or append a pre-verified source identifier to the prescription data 1512 submitted to shared ledger system 1540. This source identifier may then be used later by shared ledger system 1540 to verify the source of the modification to the prescription as the source of the originally submitted prescription.

A prescription verification device 1520 may include features similar to those found in prescription entry device 1502. For example, prescription verification device 1520 includes a processor 1522, memory 1524, network interface 1526 similar to those found in prescription entry device 1502. In some aspects, prescription verification device 1520 may be provided to pharmacies, hospitals, or other similar entities that receive and dispense prescriptions. For example, prescription verification device 1520 may be a computing device associated with or owned by a pharmacy, hospital, or other similar entity. In some aspects, prescription verification device 1520 may also include a scanning device 1528 that is configured to digitally scan prescriptions 502 and generate prescription data 1530 based on the scanned prescriptions for storage in memory 1524 in a similar manner to that described above with reference to scanning device 1510. In some aspects, prescription data 1530 for each prescription may include an image of the prescription. In some aspects, scanning device 1528 and prescription verification device 1520 may be separate devices that are in communication via network interface 1526.

In some aspects, for example, a pharmacist and drug vending system may use prescription verification device 1520 to verify the authenticity of a prescription received from a customer. For example, the drug vending system may use prescription verification device 1520 to query shared ledger system 1540 to determine if the prescription received from the customer is present on the shared ledger and may verify the authenticity of the prescription based on the prescription data 1512 that has been appended to blockchain 1550. For example, the drug vending system may compare the validation code printed on the prescription to the validation code found in the prescription data 1512 appended to blockchain 1550. In some aspects, the prescription received from the customer may be scanned in by scanning device 1528 in a similar manner to that described above with reference to scanning device 1510, a new validation code may be generated for the scanned prescription and the new validation code may be compared to the validation code found in the prescription data 1512 appended to blockchain 1550.

In some aspects, for example, a digital image of the prescription generated by the prescription verification device 1520 may be compared to a digital image of the prescription generated by prescription entry device 1502. For example, the digital image of the prescription generated by the prescription entry device 1502 may be stored with prescription data 1512 on blockchain 1550 or in a separate database associated with blockchain 1550 and may be downloaded by prescription verification device 1520 for comparison to the digital image of the prescription generated by prescription verification device 1520. In some aspects, for example, the prescription verification device 1520 may compare the digital images using pixel comparison techniques and may set a maximum difference threshold for the pixel comparison. For example, a non-limiting maximum difference threshold between the digital images of the prescription may be set at 3%, e.g., the pixels of the digital images of the prescription may differ by no more than 3%. In some aspects, a maximum difference threshold may also or alternatively be defined separately for each key region of the prescription, e.g., 3% for a first key region, 1% for a second key region, 2% for a third key region, 30% for a fourth key region, etc.

In some aspects, the pixel comparison results for each of the key regions may be combined and compared to a total maximum difference threshold to determine whether the prescription has been modified. For example, if the total maximum difference threshold for the prescription is 5%, a first key region has a pixel difference of 2% and a second key region has a pixel difference of 3%, the prescription may be determined to have been modified. In another example, if the individual regions each had a 1% difference but cumulatively added up to a 5% difference, a modification may be determined even though the maximum difference threshold for each key region may not have been triggered. In some aspects, the key regions may have weightings where, for example, key regions related to pill count, number of refills, etc. may have a higher weight than key regions related to the doctor's name or office.

The maximum difference thresholds for the comparison may be pre-determined in advance, may be set by a user of the prescription verification device 1520, may be set by a user of the prescription entry device 1502, or by any other user of the system. For example, the maximum difference thresholds may be set by a government entity, medical personnel, or other entity based on data that indicates which key regions of the prescription or how much of the prescription is typically changed in the case of a fraudulent prescription.

In some aspects, whenever a pharmacy receives a prescription from a customer, a query or check-in may be submitted to the shared ledger system 1540 for the prescription to determine whether the prescription is valid. The query may be submitted as a query transaction that may be added to blockchain 1550. For example, every time a query is submitted for a particular prescription, the query may be added to blockchain 1550 as a transaction such that all future queries will receive a notification that the prescription has been previously queried. In some aspects, the query transaction may include, for example, an identification of the querying entity, a timestamp of the query, a location of the query, or any other information that may be relevant to determining whether a fraudulent use of a prescription occurred. For example, if a query for a particular prescription has been submitted from three different pharmacies in the same area on the same day, this may be a red flag that a customer is attempting fraud since it appears that the customer may have tried to fill the same prescription in each of the three different pharmacies. In some aspects, once a predefined threshold number of queries have been received by shared ledger system 1540 for a particular prescription, shared ledger system 1540 may indicate to a pharmacist or other entity via prescription verification device 1520 that manual validation of the prescription is required, e.g., by contacting the prescribing physician directly.

Upon validation of the prescription, the drug vending system activates the actuator to dispense the prescribed drug to the user.

INCORPORATION BY REFERENCE

All references, including granted patents and patent application publications, referred to herein are incorporated herein by reference in their entirety.

U.S. Publication Number US20210249112A1 titled "Integrated device and system for drug dispensing"

U.S. Publication Number US20210398635A1 titled "Medication compliance device"

U.S. Publication U.S. Pat. No. 11,100,741B2 titled "Secure inventory access and control mechanism"

U.S. Publication Number US20210343404A1 titled "Health management system"

U.S. Publication Number US20160022542A1 titled "Home medication manager"

U.S. Publication U.S. Pat. No. 10,709,643B2 titled "Tamper-proof pill dispensing system and methods of use"

U.S. Pat. No. 9,203,861 titled "Methods and systems for determining hardening strategies"

U.S. Pat. No. 9,436,822 titled "Virtual browsing environment"

U.S. Pat. No. 10,956,184 titled "Malware detector"

U.S. Pat. No. 9,846,588 titled "on demand disposable virtual work system"

U.S. Pat. No. 8,082,452 titled "Protecting sensitive data associations"

U.S. Publication 20100054481 titled "Scalable distributed data structure with recoverable encryption"

U.S. Pat. No. 8,566,269 titled "Interactive analysis of attack graphs using relational queries"

U.S. Publication 20100058456 titled "IDS sensor placement using attack graphs"

U.S. Pat. No. 11,393,568B2 titled "Blockchain prescription management system"

U.S. Pat. No. 10,942,956B2 titled "Detecting medical fraud and medical misuse using a shared virtual ledger"
U.S. Pat. No. 6,981,637B2 titled "Automatic teller machine"

What is claimed is:

1. A system comprising:
a drug vending system,
wherein the drug vending system comprises:
   a drug storage system comprising a drug storage to hold a drug container comprising a drug;
   a processor;
   a memory; wherein the processor is communicatively coupled with the memory;
   a communication module; and
   a cyber security module;
   and wherein the processor is operable to:
      log a record of access to the drug container, and maintain a ledger of the record of access to the drug container using a blockchain technology; and
      wherein the drug vending system is secured through the cyber security module.

2. The system of claim 1, wherein the system comprises a user interface to interact with a user.

3. The system of claim 1, wherein the system is in communication with a server through the communication module; and wherein the server comprises a database.

4. The system of claim 2, wherein the system receives a prescription through the user interface wherein the user interface comprises a scanner to scan the prescription.

5. The system of claim 4, wherein the prescription comprises a unique code comprising at least one of a barcode, a Universal Product Code indicia, a Quick Response code, a high-capacity color barcode, and a near-field communication code.

6. The system of claim 4, wherein the prescription is received from a digital medium and as a blockchain token.

7. The system of claim 4, wherein the system receives at least one of a biometric identity of the user and a unique identity of the user through the user interface and interact with a server to authenticate the user by matching credentials of the unique identity and biometric identity with a record of the user stored in a database.

8. The system of claim 7, wherein the user interface further comprises a biometric scanner to scan the biometric identity of the user; and a keypad; a touchpad; a scanner; and a RFID reader to receive a unique identity of the user.

9. The system of claim 8, wherein the drug vending system is locked for further access if the credentials of the unique identity does not match with the record of the user in the database.

10. The system of claim 7, wherein the biometric identity comprises at least one of a fingerprint, an eyeblink, a retina scan, an iris scan, an eye scan, and a facial image scan.

11. The system of claim 7, wherein the unique identity comprises at least one of an alphanumeric password, a unique identification number, an RFID tag, a password, a barcode, and a Quick response QR code.

12. The system of claim 1, wherein the system is installed at least one of a pharmacy, a drug store, and a box store.

13. The system of claim 4, wherein the system provides an access to the drug vending system to refill the prescription into the drug storage.

14. The system of claim 7, wherein the system checks and authenticates dispensing of the drug with an inventory of the drug according to the prescription received; and dispenses the drug container from the drug vending system; and wherein a detail of the drug is sent to the server on each of the access to the drug container from the drug storage in order to track the access to the drug container; and wherein the detail of the drug comprises a batch number, an inventory count of the drug container, a name of the drug, an expiry date, and a disease it is used to treat.

15. The system of claim 1, wherein the system is a Drug Enforcement Administration compliant system.

16. The system of claim 7, wherein the cyber security module further comprises an information security management module providing isolation between the system and the server.

17. The system of claim 16, wherein the information security management module is operable to:
   receive data from at least one of an input interface, the drug storage, and the database;
   exchange a security key at a start of the communication between the communication module and the server;
   receive the security key from the server;
   authenticate an identity of the server by verifying the security key;
   analyze the security key for potential cyber security threats;
   negotiate an encryption key between the communication module and the server;
   encrypt the data; and
   transmit the encrypted data to the server in case no cyber security threat is detected.

18. The system of claim 16, wherein the information security management module is operable to:
   exchange a security key at a start of the communication between the communication module and the server
   receive the security key from the server;
   authenticate an identity of the server by verifying the security key;
   analyze the security key for potential cyber security threats;
   negotiate an encryption key between the system and the server;
   receive encrypted data;
   decrypt the encrypted data;
   perform an integrity check of the decrypted data; and
   transmit the decrypted data to at least one of an output interface, the drug storage, and the database through the communication module in case no cyber security threat is detected.

19. A method comprising steps of:
   receiving an identification of a user through a drug vending system;
   authenticating the user through the drug vending system;
   receiving a prescription through the drug vending system;
   dispensing a drug container through the drug vending system to the user;
   communicating through a communication module;
   logging a record of access to the drug container;
   maintaining a ledger of the record of access to the drug container using blockchain technology; and
   wherein the drug vending system is secured through a cyber security module.

20. A system comprising:
   an automatic drug vending machine to dispense a drug container;
   a drug storage system comprising a drug storage to hold the drug container comprising a drug;

a processor;
a memory; wherein the processor is communicatively coupled with the memory;
a communication module; and
a cyber security module;
and wherein the processor is operable to:
  log a record of access to the drug container, and
  maintain a ledger of the record of access to the drug container using a blockchain technology; and
wherein the system is secured through the cyber security module.

* * * * *